(12) United States Patent
Srinivasan et al.

(10) Patent No.: US 7,884,945 B2
(45) Date of Patent: Feb. 8, 2011

(54) METHODS AND APPARATUS FOR OPTICAL COHERENCE TOMOGRAPHY SCANNING

(75) Inventors: Vivek Srinivasan, Cambridge, MA (US); James Fujimoto, Medford, MA (US); Tony Ko, San Jose, CA (US); Maciej Wojtkowski, Cambridge, MA (US); Robert Huber, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 88 days.

(21) Appl. No.: 11/336,427

(22) Filed: Jan. 20, 2006

(65) Prior Publication Data

US 2006/0187462 A1 Aug. 24, 2006

Related U.S. Application Data

(60) Provisional application No. 60/645,665, filed on Jan. 21, 2005.

(51) Int. Cl.
*G01B 11/02* (2006.01)
(52) U.S. Cl. .................................. 356/497; 356/479
(58) Field of Classification Search ................ 356/479, 356/497
See application file for complete search history.

(56) References Cited

U.S. PATENT DOCUMENTS

| | | | |
|---|---|---|---|
| 5,493,109 A | 2/1996 | Wei et al. | |
| 5,501,226 A | 3/1996 | Peterson et al. | |
| 5,644,642 A * | 7/1997 | Kirschbaum | 382/103 |
| 5,956,355 A | 9/1999 | Swanson et al. | |
| 6,004,314 A | 12/1999 | Wei et al. | |
| 6,053,613 A | 4/2000 | Wei et al. | |
| 6,191,862 B1 | 2/2001 | Swanson et al. | |
| 6,293,674 B1 | 9/2001 | Huang et al. | |
| 6,385,358 B1 * | 5/2002 | Everett et al. | 385/12 |
| 6,722,767 B2 | 4/2004 | Dick et al. | |

(Continued)

FOREIGN PATENT DOCUMENTS

DE 103 23 217 A1 12/2004

OTHER PUBLICATIONS

Koozekanani et al (Tracking the Optic Nervehead in OCT Video Using Dual Eigenspaces and an Adaptive Vascular Distribution Model, IEEE Transactions on Medical Imaging, vol. 22, No. 12, Dec. 2003).*

(Continued)

*Primary Examiner*—Tarifur Chowdhury
*Assistant Examiner*—Jonathon D Cook
(74) *Attorney, Agent, or Firm*—Hamilton, Brook, Smith & Reynolds, P.C.

(57) ABSTRACT

In one aspect, the invention relates to a method of acquiring optical coherence tomographic data from a sample. The method includes the steps of scanning a first location on the sample to obtain a first set of optical coherence tomographic data, scanning a second location on the sample to obtain a second set of optical coherence tomographic data, and defining a fiducial position relative to a location on the sample using one of the two sets of optical coherence tomographic data. In one embodiment, the first set of optical coherence tomographic data is survey data. However, in another embodiment the first set of optical coherence tomographic data is sample measurement data.

63 Claims, 41 Drawing Sheets

U.S. PATENT DOCUMENTS

| | | | |
|---|---|---|---|
| 6,741,359 | B2 | 5/2004 | Wei et al. |
| 6,741,948 | B2 | 5/2004 | Hauger et al. |
| 6,779,891 | B1 | 8/2004 | Barth et al. |
| 6,788,421 | B2 | 9/2004 | Fercher et al. |
| 6,922,250 | B2 | 7/2005 | Fercher |
| 6,997,555 | B2 | 2/2006 | Dick et al. |
| 7,084,986 | B2 | 8/2006 | Hellmuth et al. |
| 7,126,693 | B2 | 10/2006 | Everett et al. |
| 7,128,737 | B1 | 10/2006 | Goder et al. |
| 7,145,661 | B2 | 12/2006 | Hitzenberger |
| 7,301,644 | B2 | 11/2007 | Knighton et al. |
| 7,401,921 | B2 | 7/2008 | Baker et al. |
| 7,477,764 | B2 | 1/2009 | Haisch |
| 2004/0233457 | A1 | 11/2004 | Podoleanu et al. |
| 2005/0140984 | A1* | 6/2005 | Hitzenberger ............... 356/497 |

OTHER PUBLICATIONS

Hee, M.R., et al., "Topography of Diabetic Macular Edema with Optical Coherence Tomography," Ophth. 105 (2):360-370 (1998).

Anger, E.M., et al., "Ultrahigh Resolution Optical Coherence Tomography of the Monkey fovea. Identification of Retinal Sublayers by Correlation with Semithin Histology Sections," Exp. Eye. Res., 78(6):1117-25 (2004).

Bajraszewski, T., et al., "Three-Dimensional In Vivo Imaging by Spectral OCT," SPIE-Int. Soc. Opt. Eng, 5316: 226-32 (2004).

Iftimia, N. V., et al., "Adaptive Ranging for Optical Coherence Tomography," Optics Express, 12(17): 4025-4034 (2004).

Nassif, N. A., et al., "In Vivo High-Resolution Video-Rate Spectral-Domain Optical Coherence Tomography of the Human Retina and Optic Nerve," Optics Express, 12 (3):367-376 (2004).

Wojtkowski, M., et al., "Ophthalmic Imaging by Spectral Optical Coherence Tomography," Am. J. Ophthalmol. 138 (3):412-9 (2004).

Wojtkowski, M., et al., "Real-Time and Static In Vivo Ophthalmic Imaging by Spectral Optical Coherence Tomography," SPIE-Int. Soc. Opt. Eng. 5314: 126-31 (2004).

Wojtkowski, M., et al., "Ultrahigh-Resolution, High-Speed, Fourier Domain Optical Coherence Tomography and Methods for Dispersion Compensation," Optics Express, 12 (11):2404-2422 (2004).

Hee, et al., "Interpretation of the Optical Coherence Tomography Image," *Chapter 2 of Optical Coherence Tomography of Ocular Diseases, Second Edition*, pp. 21-53, (2004).

Stein, et al., "Imaging in Glaucoma," *Ophthalmology Clinics of North America*, vol. 17, pp. 33-52 (2004).

\* cited by examiner

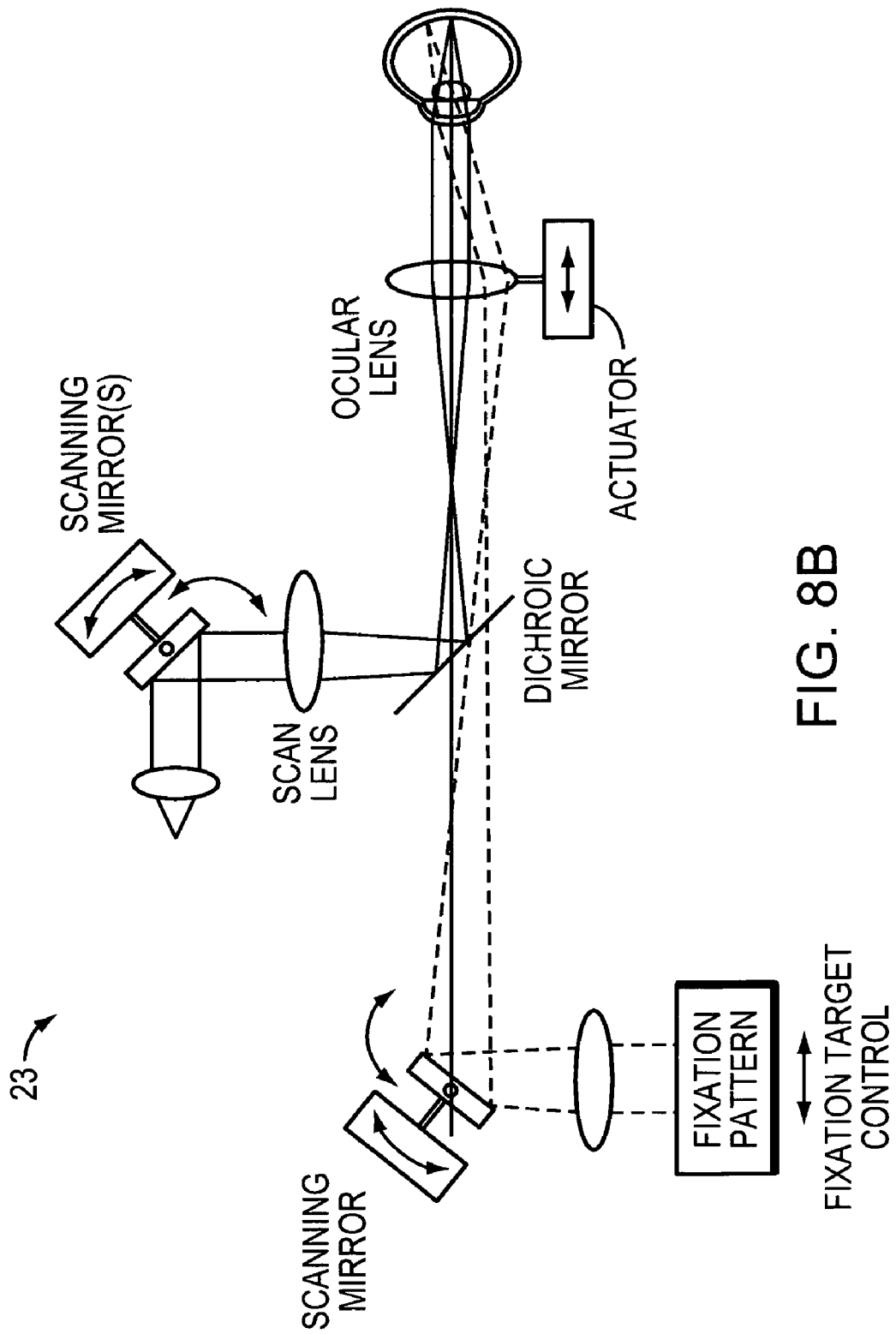

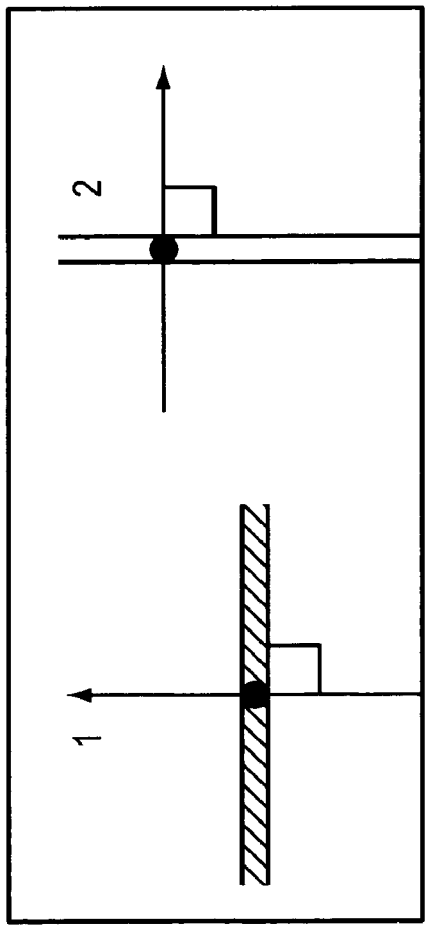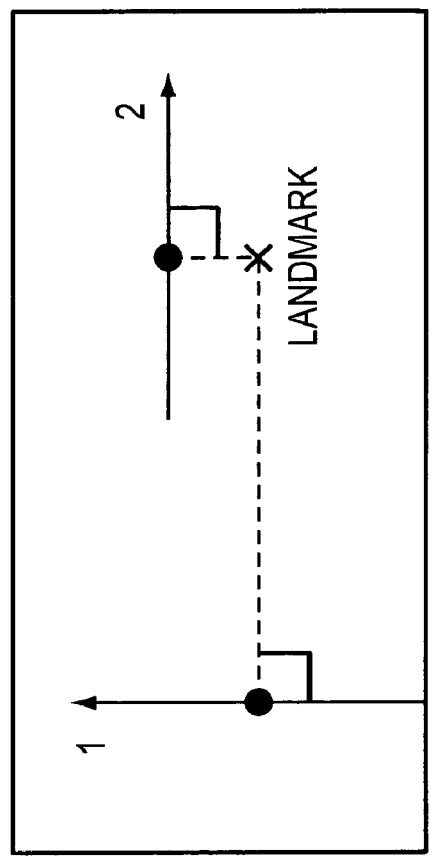
FIG. 14A

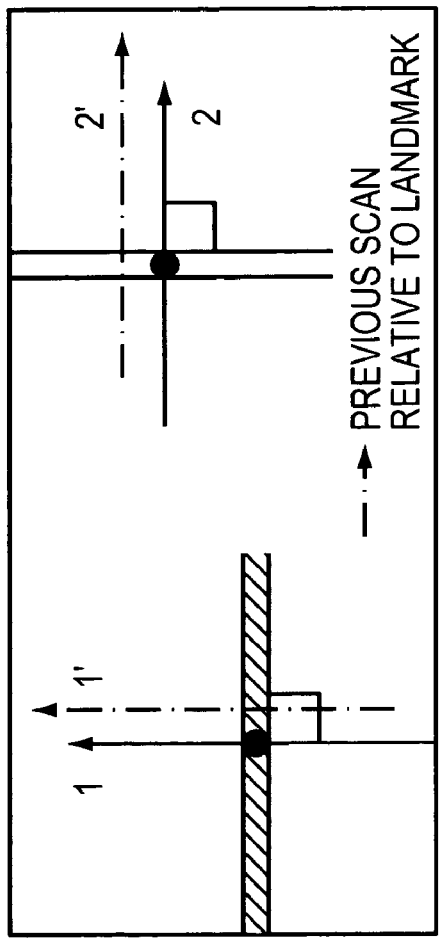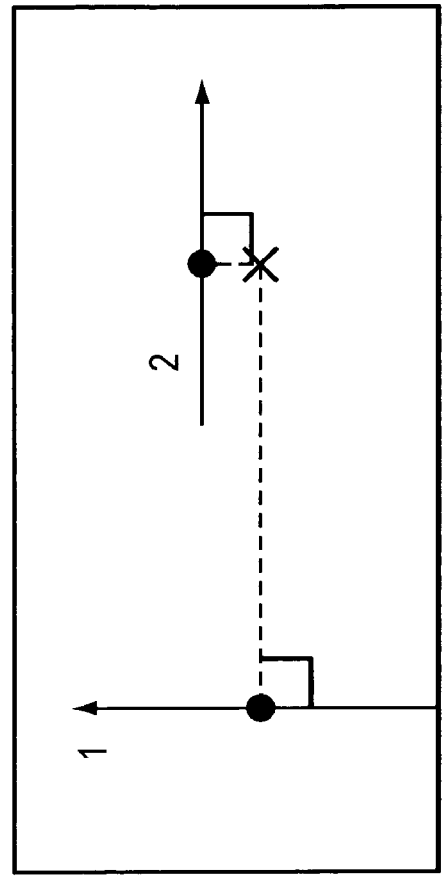
FIG. 14B

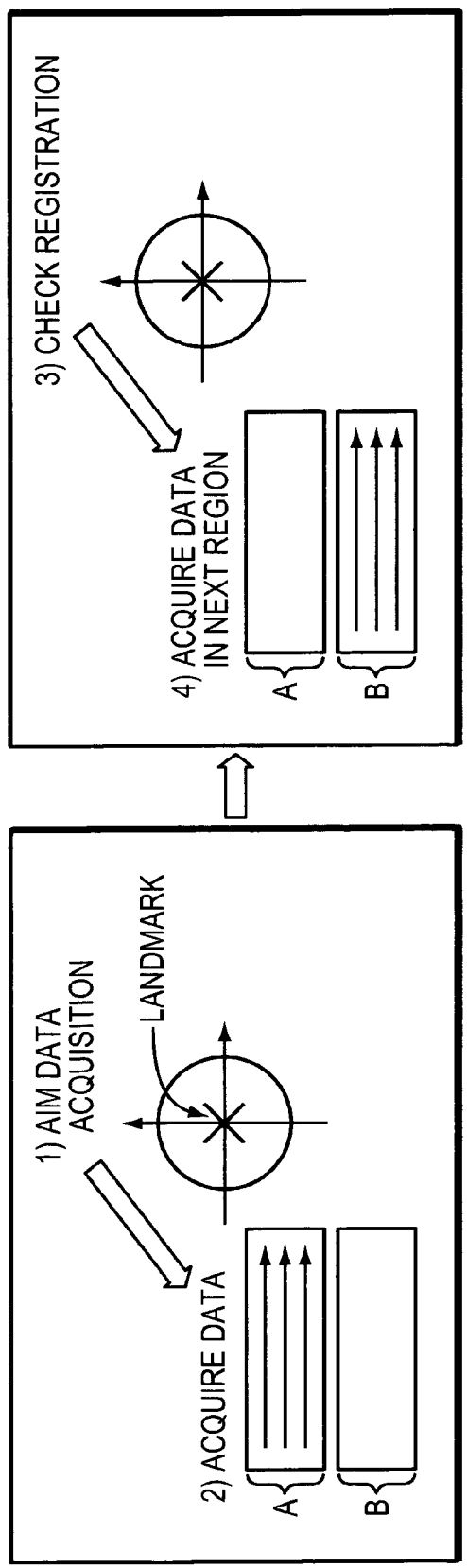

EPITHELIUM

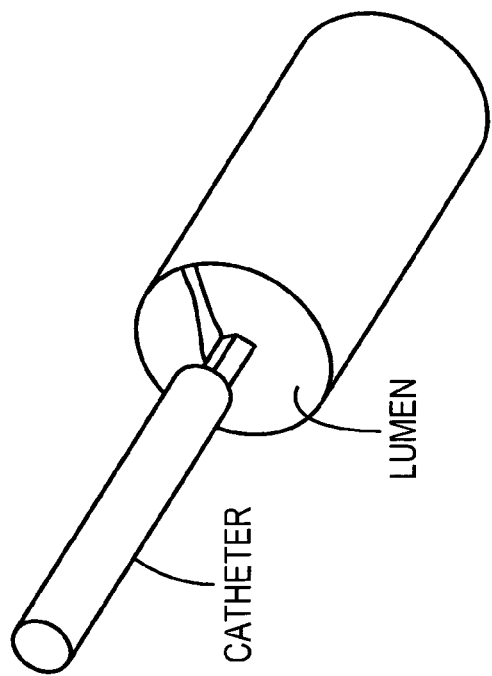
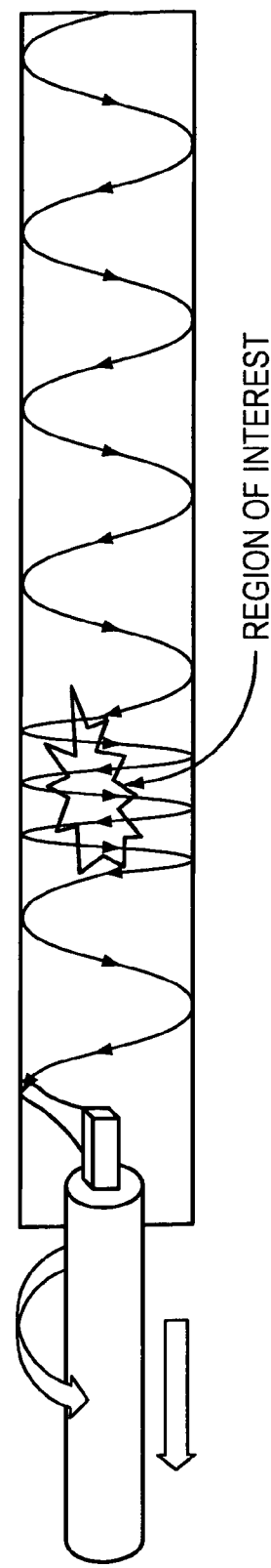

METHODS AND APPARATUS FOR OPTICAL COHERENCE TOMOGRAPHY SCANNING

RELATED APPLICATIONS

This application claims priority to U.S. Provisional Patent Application 60/645,665 filed on Jan. 21, 2005 the disclosure of which is herein incorporated by reference in its entirety.

GOVERNMENT SUPPORT

This invention was made with government support under Grant Numbers CA075289 and EY011289, awarded by NIH, and Grant Number FA9550-04-1-0046, awarded by the Air Force. The government has certain rights in the invention.

FIELD OF THE INVENTION

The invention relates generally to the field of optical coherence tomography and applications thereof. Specifically, the invention relates to devices and methods for enhanced scanning and data acquisition.

BACKGROUND OF THE INVENTION

Optical coherence tomography performs cross-sectional imaging, three-dimensional imaging, or data acquisition in materials or biological tissue by measuring the magnitude and time delay of backscattered or backreflected light from inside the sample. OCT performs imaging or measurement by directing a light beam at the sample, measuring the backscattering or backreflected signal from the sample as a function of the optical delay (known as an axial scan or A-scan), and scanning the OCT beam incident on the tissue or material to generate a two or three dimensional dataset which represents cross-sectional or volumetric information about the internal structure of the sample. In the case where the dataset includes a set of axial scans at sequential transverse positions, it is usually displayed as false color or grey scale images which represent cross-sections through the sample.

Directing and aiming of OCT beam scanning by a human operator is subject to speed and accuracy limitations and may not be feasible in many OCT applications. Prior systems for improving the registration of OCT images or data to landmarks or features on the sample have used an active tracking system, which required a separate optical tracking beam to actively control the position of the OCT beam with respect to the sample. However, the requirement of a second tracking beam in active tracking systems adds significantly to the complexity of the OCT apparatus and is also impractical for many OCT applications, such as for endoscopy.

Accordingly, a need therefore exists for techniques and devices that improve the efficiency by which OCT data is collected. Methods that enable accurate data collection from specific regions of a sample within short time periods are also desirable.

SUMMARY OF THE INVENTION

The aspects and embodiments of the invention disclosed herein relate to methods, systems and devices for enhancing the performance and accuracy of optical coherence tomography (OCT). As a result, new OCT applications and devices are enabled that were not previously possible. In part, the aspects disclosed herein relate to intelligent scanning with respect to particular landmarks or fiducial positions in a sample.

The aspects of the invention disclosed herein offer many advantages over the prior art. One of the advantages is that image generation is not necessary to register OCT scans and that secondary aiming systems are no longer required. These advantages arise from the intelligent scanning techniques disclosed herein.

Intelligent scanning operates by directing OCT data acquisition, survey scans and/or data processing using computer control or other automated means. The data acquisition is directed based on an analysis of survey/registration OCT data. Thus, aspects of the invention enable more accurate and reproducible registration of OCT images or data with respect to the location of features or landmarks in the sample. In addition, various aspects enable the acquisition of larger data sets without motion artifacts than was previously possible. In one aspect, the invention relates to OCT instruments which can acquire accurate images or data with minimal operator control or in situations where operator control is not feasible.

The OCT scanning techniques described herein can be performed using different systems and device configurations. Exemplary OCT system suitable for use with the disclosed scanning techniques include, but are not limited to: an interferometer with a broadband light source and scanning optical reference delay line; an interferometer with a broadband light source and a spectrometer for signal detection (known as Fourier domain OCT, spectral domain OCT, spectral radar, and other designations); and/or an interferometer with a frequency swept light source (known as Fourier domain OCT, swept source OCT, optical frequency domain imaging or other designations).

In many OCT applications, there is a need to direct or aim the OCT beam scanning to acquire data or images from a particular region of the sample. There may also be a need to direct or aim the OCT beam scanning to acquire data or images that are precisely registered to a particular feature or landmark on or in the sample. Registering a feature or element refers to identifying its location relative to a position in the sample, a data set, or other fixed location. One exemplary application of intelligent scanning occurs in the field of ophthalmic OCT. Specifically, directing or aiming the OCT beam to scan around the optic nerve head or macula to achieve precise registration with features or landmarks of the nerve head or retina is one aspect of the invention. This enables precise position registration of the OCT images or data with respect to landmarks and facilitates comparison of the OCT images or data between clinical subjects. In the aforementioned example, the OCT images or data obtained for an area around the optic nerve head are analyzed to measure the thickness of the nerve fiber layer and to compare this thickness to a database of nerve fiber layer thickness to diagnose disease. Thus, this enables more accurate diagnosis of disease.

In many biomedical imaging applications, such as in longitudinal tracking of pathologic changes over a period of time, OCT data or images are acquired at precise and reproducible positions with respect to features or landmarks in the tissue. Therefore, reproducibly performing OCT data or image acquisition over multiple imaging sessions for the same sample is a desirable feature of the invention. The reproducible scanning is especially important in applications where OCT images or data are quantitatively analyzed and changes in parameters are assessed over time. As a result, more accurate and reproducible registration is possible than compared with operator control of OCT beam scanning. Since reproducible OCT imaging and measurement of the retinal nerve fiber layer and other sample areas are possible, monitoring disease progression and response to therapy is significantly improved. Thus, tracking disease progression using periodic OCT scans is one aspect of the invention.

The method and apparatus of intelligent OCT scanning, which directs and aims OCT beam scanning for image and data acquisition, enables the use of OCT in new instruments and applications. Intelligent OCT scanning allows for usable scan results without the need for a trained operator to perform the initial aiming. Also, when motion of the subject would otherwise prevent accurate results, the techniques disclosed herein can compensate for operator or patient motion. As a result, hand-held OCT scanners and low-cost OCT retinal screening devices are also possible using the techniques disclosed herein.

Intelligent scanning also enables the evaluation of an OCT data set to assess whether motion has occurred during the data acquisition. This can be used to assess the accuracy of the registration of the OCT data with respect to features or landmarks in the sample. OCT data that is not registered with sufficient accuracy or that has motion error can be discarded and re-acquired such that it accurately registered.

In another embodiment, intelligent OCT scanning can be used for tracking motion or correcting for motion errors, thereby allowing the acquisition of large, substantially motion error free OCT data sets. In this application, intelligent scanning is used to periodically re-direct or re-aim the OCT data acquisition to maintain registration of a series of OCT data sets. These OCT data sets can be acquired in different locations in the sample and are precisely registered to features or landmarks in the sample. Therefore, since these data sets are precisely registered with respect to each other, they can be combined to create a larger OCT data set.

Intelligent scanning may also be used to direct the analysis of an existing OCT data set to improve the processing of the OCT data or remove errors from motion. Examples include, but are not limited to, registering the location of images or data with respect to features or landmarks on or in the sample, superposing multiple images or data sets to generate a larger image or data set which is registered to features or landmarks, and correcting for motion error in images or data sets. It is also possible to direct processing or analysis to a particular subset of a larger data set such that the subset is registered to a location on the sample. For example, intelligent scanning can determine a registered and reproducible location of a virtual, two dimensional OCT circumpapillary image using a three dimensional OCT data set.

Intelligent scanning can be used to direct or aim OCT beam scanning as well as to control the mode of operation of the OCT instrument. These features are useful for identifying regions of interest in a sample. This is especially applicable in so-called "enhanced performance" OCT applications wherein a desired region of interest is scanned with enhanced performance. In many of these applications, data or images can only be acquired from a limited region within a given time because acquisition speeds for enhanced performance are limited. Intelligent scanning can be used in these cases where it would otherwise be impractical or too slow to acquire images or data over a large region in the "enhanced performance" mode of operation.

Although the description of some of the aspects of the invention uses examples from ophthalmology, it is recognized that the invention applies to many other OCT imaging and measurement applications. These applications include, but are not limited to: surgical microscopy, surgical guidance, laparoscopy, cystoscopy, laryngoscopy, colposcopy, endoscopy, bronchoscopy, intravascular imaging, microscopy, non-destructive evaluation of materials, and process monitoring.

In one aspect, the invention relates to a method of acquiring optical coherence tomographic data from a sample. The method includes the steps of scanning a first location on the sample to obtain a first set of optical coherence tomographic data, scanning a second location on the sample to obtain a second set of optical coherence tomographic data, and defining a fiducial position relative to a location on the sample using one of the two sets of optical coherence tomographic data. In one embodiment, the first set of optical coherence tomographic data is survey data. However, in another embodiment the first set of optical coherence tomographic data is sample measurement data. The first set of optical coherence tomographic data can contain data from three axial scans having locations in the transverse plane that are non-collinear. In one embodiment, the method further includes the step of transforming three dimensional data to two dimensional data to identify a landmark on the sample. The sample can be a mammalian eye such as a human eye. The fiducial position can include a portion of at least one of an optic nerve head or an optic disk. The first scan can be a survey scan. The first scan can also be a measurement scan. In one embodiment, the method further includes the step of tracking changes in the fiducial position using the first scan or the second scan. The first location and the second location can be substantially the same.

In another aspect, the invention relates to a method of acquiring optical coherence tomographic data from a sample. The method includes the steps of collecting optical coherence tomographic survey data from a first location on the sample, defining a first position relative to the first location using the optical coherence tomographic survey data, and performing an optical coherence tomographic scan to obtain optical coherence tomographic measurement data from the sample in response to the first position. In one embodiment, at least one of the first position, the first location on the sample and the second location on the sample are the same. The optical coherence tomographic data can be obtained using a hand-held scanner. The optical coherence tomographic survey data can be used to obtain OCT data which is registered with respect to features in a human eye.

In yet another aspect, the invention relates to a method of evaluating optical coherence -tomography (OCT) data obtained from a sample having a landmark. The method includes the steps of performing a first OCT scan of a region on the sample to generate a first data set, the first data set comprising positional information about the landmark, and performing a second OCT scan using the positional information from the first scan. The first OCT scan can be a survey scan and the second scan can be a measurement scan. In one embodiment, the method further includes the step of iteratively performing survey optical coherence tomographic scans of the first sample region prior to performing the measurement optical coherence tomographic scan.

In still another aspect, the invention relates to a method of evaluating optical coherence tomography (OCT) data obtained from a sample having a landmark. The method includes the steps of performing a first OCT scan of a location on the sample to generate a first survey data set, the first survey data set comprising first OCT scan positional information about the landmark, and performing a second OCT scan using the first OCT positional information from the first OCT scan. In one embodiment, the method further includes the step of performing a third OCT scan of the sample to generate a second survey data set, the second survey data set comprising second OCT positional information about the landmark, and comparing the first OCT scan positional information and the second OCT scan positional information to determine an amount of change in landmark position, the amount of change in landmark position indicative of an error level. The amount of change in landmark position can be used to determine if an additional measurement OCT data acquisition scan is necessary. In one embodiment, the method further includes the step of performing a fourth OCT scan if the error level exceeds a predetermined threshold.

In another aspect, the invention relates to a method of processing optical coherence tomography (OCT) data obtained for a sample. The method includes the steps of performing a survey scan to obtain survey scan data, performing an optical coherence tomography scan to obtain sample data, analyzing the survey scan data to identify landmark region data, and processing the sample data in response to the landmark region data. In one embodiment, the method further includes the step of selecting a subset of data from the sample data for processing in response to the landmark region data. The method can further include the step of generating an image using the sample data. In one embodiment, the method further includes the step of generating numerical measurements regarding portions of elements in the sample using the sample data. The elements can be constituents of a human eye. In one embodiment, the method further includes the step of correcting for movement artifacts using the survey scan data.

In another aspect, the invention relates to a method of monitoring disease progression in a human eye. The method includes the steps of performing a survey scan to obtain survey scan data, analyzing the survey scan data to identify a landmark region in the eye, registering a portion of a region of affected tissue in the eye relative to the landmark region, and monitoring changes to the region of affected tissue at different points in time. In one embodiment, the region of affected tissue can include, but is not limited to corneal tissue, retinal tissue (nerve fiber layer, photoreceptors, retinal pigment epithelium, ganglion cell layer, nuclear layers, plexiform layers), cardiac tissue, and components thereof. The points in time can correspond to a plurality of eye exams.

In another aspect, the invention relates to an optical coherence tomographic device for obtaining optical coherence tomographic data of a sample location. The device can include means for performing a first optical coherence tomographic scan of a first sample location to obtain first optical coherence tomographic data, means for defining a fiducial position relative to the first sample location in response to the first optical coherence tomographic data obtained from the first optical coherence tomographic scan, and automated means for performing a second optical coherence tomographic scan to obtain second optical coherence tomographic data from the first sample location in response to the fiducial position from the first sample location. In one embodiment, the device further includes means for performing a supplemental measurement scan in response to changes in the fiducial position.

In another aspect, the invention relates to an optical coherence tomographic device. The device includes an opto-mechanical system adapted for beam steering and OCT scanning, and a controller in communication with the opto-mechanical system, wherein the controller causes the opto-mechanical system to perform a first optical coherence tomographic scan of a first sample location to obtain first optical coherence tomographic data, wherein the controller defines a fiducial position with respect to the first sample location in response to the first optical coherence tomographic data obtained from the survey optical coherence tomographic scan, and wherein the controller causes the OCT interferometer to perform a second optical coherence tomographic scan to obtain second optical coherence tomographic in response to the fiducial position in the first sample location.

Additionally, in one embodiment, the controller further tracks changes in the fiducial position in the first sample location. In one embodiment, the controller further causes the OCT interferometer to perform a supplemental measurement scan in response to changes in the fiducial position. The controller can cause the OCT interferometer to repeat the measurement OCT data acquisition scan if the quality of the measurement OCT data acquisition scan does not exceed a predetermined level of error. In one embodiment, the opto-mechanical system includes an interferometer sample arm such that a portion of the interferometer sample arm is handheld. A survey optical coherence tomographic scan location can be initiated by the controller. The device can further include an optical fiber such that optical coherence tomography beam positioning is performed by actuating the optical fiber. In one embodiment, the device is an ophthalmic device. A survey optical coherence tomographic scan location can be determined by using a subject's eye fixation.

It should be understood that the terms "a," "an," and "the" mean "one or more," unless expressly specified otherwise.

The foregoing, and other features and advantages of the invention, as well as the invention itself, will be more fully understood from the description, drawings, and claims which follow.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. The drawings associated with the disclosure are addressed on an individual basis within the disclosure as they are introduced.

FIG. 8b is a schematic diagram depicting an intelligent retinal screener according to an illustrative embodiment of the invention;

FIGS. 14A-14C are schematic diagrams depicting perpendicular linear features used to define a landmark according to an illustrative embodiment of the invention;

FIGS. 18A-18C are a set of schematic diagrams depicting intelligent OCT scanning used to acquire data in multiple regions with a registration accuracy check according to an illustrative embodiment of the invention;

FIGS. 33A-33B are schematic diagrams depicting the use of intelligent scanning in catheter-based OCT applications according to an illustrative embodiment of the invention.

The claimed invention will be more completely understood through the following detailed description, which should be read in conjunction with the attached drawings. In this description, like numbers refer to similar elements within various embodiments of the present invention.

DETAILED DESCRIPTION

Figure 1:
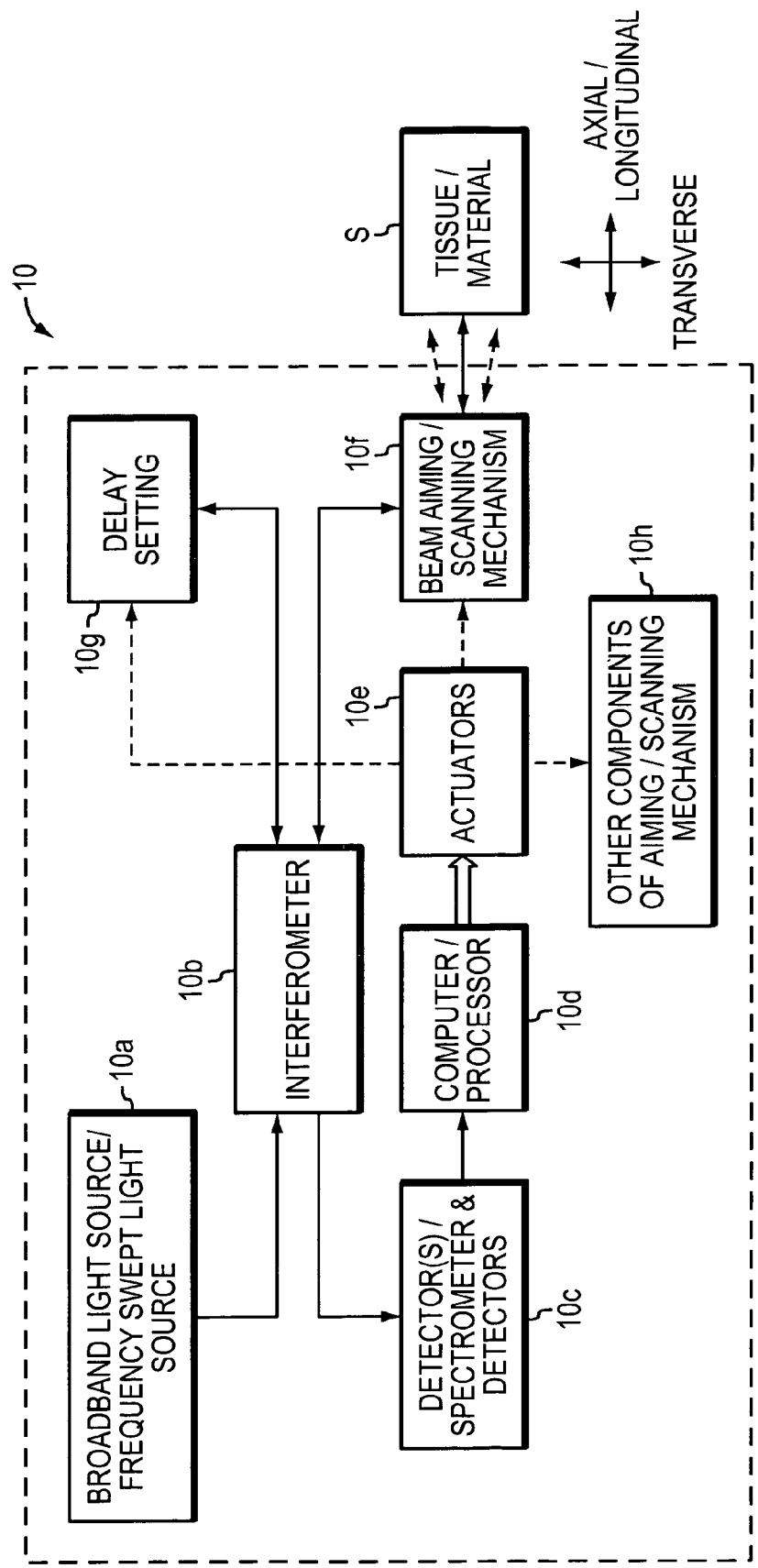
FIG. 1 is a block diagram depicting an apparatus for performing intelligent OCT scanning according to an illustrative embodiment of the invention.

The following description refers to the accompanying drawings that illustrate certain embodiments of the present invention. Other embodiments are possible and modifications may be made to the embodiments without departing from the spirit and scope of the invention. Therefore, the following detailed description is not meant to limit the present invention. Rather, the scope of the present invention is defined by the appended claims.

It should be understood that the order of the steps of the methods of the invention is immaterial so long as the invention remains operable. Moreover, two or more steps may be conducted simultaneously or in a different order than recited herein unless otherwise specified.

The invention disclosed herein improves the performance of OCT imaging or data acquisition. The improved OCT scanning approach includes multiple steps. In a preferred embodiment, these steps include scanning the OCT beam on a region of sample (generally a sample) having features or landmarks to acquire a survey/registration OCT scan, analyzing the survey/registration OCT scan by computer to extract features or landmarks from the sample and determine their location, and directing or aiming the OCT beam scanning using the location of the these features or landmarks to acquire OCT data registered with respect to the features or landmarks in the sample.

In another embodiment, the aforementioned procedure may be performed iteratively to test for the occurrence of excessive motion of the sample during the OCT data acquisition which introduces errors in OCT data registration. This enables the OCT data to be re-acquired correctly without motion error. In another embodiment, the aforementioned procedure may be performed iteratively to re-aim the OCT beam scanning during the acquisition of multiple sets or subsets of OCT data. This enables the acquisition of a larger OCT data set that includes multiple subsets which are individually registered to features or landmarks.

For example, a large region may be divided into multiple subsections, each of which is scanned separately. The OCT data sets from the subsections are individually registered to the same features or landmarks and may therefore be used to construct a larger OCT data set. In another embodiment, intelligent scanning can be performed by first performing survey/registration scans and OCT data scans. Given the resultant scan data, a processor then subsequently analyzes the survey/registration scan data to identify a landmark or fiducial point. The landmark or arbitrarily defined fiducial point is then used to direct data processing to select a subset of data from the OCT data scans which is registered with respect to the landmark.

Intelligent scanning can be performed on a large OCT data set by extracting a subset of the data to serve as registration/survey scans, analyzing the registration/survey scan data to extract features or landmarks and determining their location in the OCT data set. In turn, the location of features/landmarks is used to find a particular location associated with a portion of the larger data set to extract or identify a desired subset of the larger OCT dataset. This data is registered with respect to the features/landmarks in the sample.

The implementation of intelligent scanning requires sufficient data acquisition speed such that a large quantity of data can be acquired within a time window when motion of the sample is not appreciable. Recently, advances in OCT technology have enabled increases in acquisition speeds by factors of 10× to more than 100× faster than previously possible. This increase in OCT acquisition speed enables rapid acquisition and analysis of data. This acquisition and analysis may now be performed on a time scale that is fast enough to practice the techniques disclosed herein.

General Description of Method and Apparatus

A general apparatus 10 for intelligent OCT scanning is shown schematically in FIG. 1. As shown, the OCT apparatus directs and scans an optical OCT beam onto the tissue or material (generally a sample S) being imaged or measured. The apparatus includes a source 10a and an interferometer 10b that is in optical communication with one or more detectors 10c. The detectors capture the OCT scan data or precursor data that relates to it. The detectors are in electrical and/or optical communication with a processor 10d. The processor also controls suitable actuators 10e that control the OCT beam steering mechanism 10f. A delay setting 10g is used to regulate aspects of the interferometer 10b. In addition, other scanning components 10h may be present. In one embodiment, the actuator and beam scanning mechanism form an opto-mechanical system.

The apparatus 10 measures the magnitude and delay of backscattered or backreflected light from the sample by using interferometry. Measurements are performed by interfering the backscattered or backreflected light from the sample with light from a known reference path delay and electronically detecting the resulting optical interference signal. The OCT beam position, angle, and focus relative to the sample as well as the reference delay 10g are controlled by the processor 10d which provides control signals or waveforms to actuators 10e. The processor 10d includes specialized hardware or software that has the ability to perform feature/landmark analysis on OCT survey/registration data and direct or aim the OCT data acquisition scanning or subsequent OCT survey/registration scanning depending on this analysis. The OCT beam aiming/scanning mechanism 10f can scan the transverse position or angle of incidence of the OCT beam. The focus of the OCT beam may also be adjusted. It is also possible to translate or rotate the sample S directly or indirectly to change the position, angle of incidence, or focus of the OCT beam relative to the tissues or materials that constitute the sample.

Description of Methods of Intelligent OCT Scanning

Figure 2:
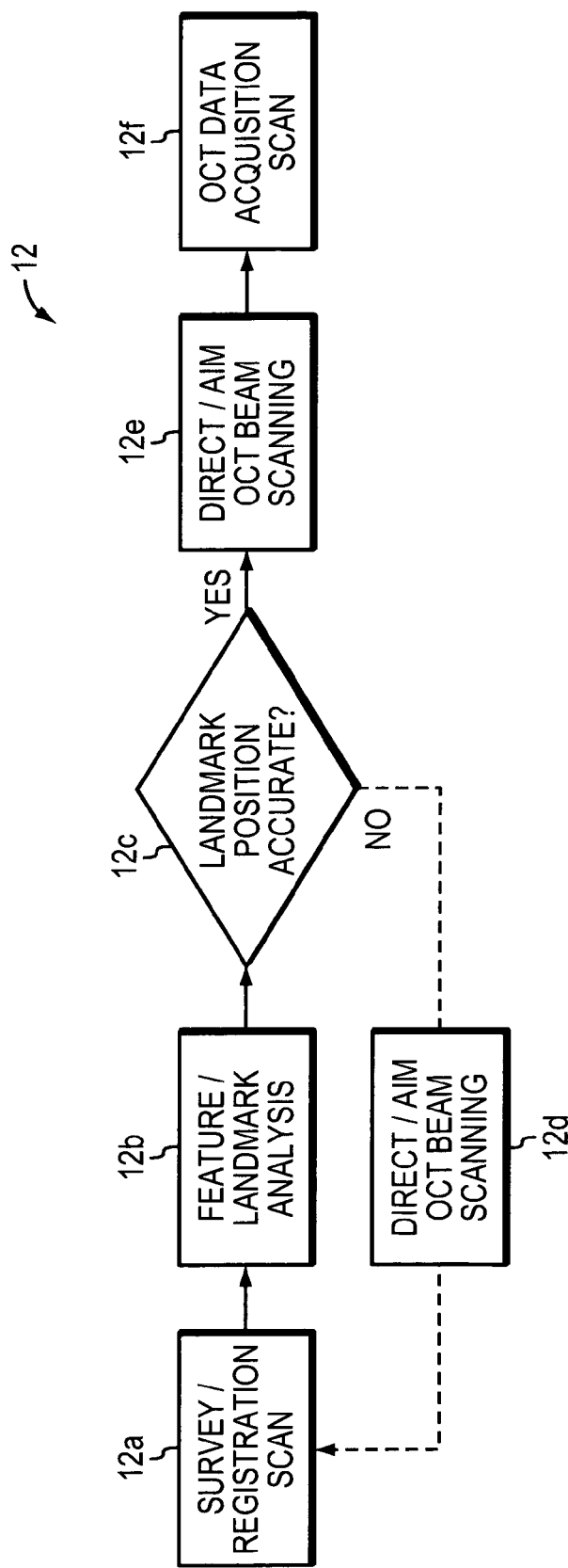
FIG. 2 is a flow diagram depicting a method of intelligent OCT scanning according to an illustrative embodiment of the invention.

A diagram outlining an exemplary method of intelligent OCT scanning 12 is shown in FIG. 2. The steps of the method 12 shown need not necessarily be performed serially, and may be performed in parallel when possible. A survey/registration OCT scan or set of scans 12a is performed by scanning the OCT beam and acquiring OCT data in the sample in a region containing a feature or landmark. The survey/registration OCT scan data can include a set of axial scans which are measurements performed as a function of depth at different transverse positions on or in the sample. The survey/registration scan pattern, or the scan pattern of the OCT beam on the sample during acquisition, is set by beam steering or positioning actuators which are driven by waveforms from a controller or computer. In general, a controller is any device that is suitable for causing an opto-mechanical system to perform an optical coherence tomographic scan. Suitable controllers include, but are not limited to a waveform generator, a processor, a DSP based controller, or a digital to analog converter.

Figure 3:
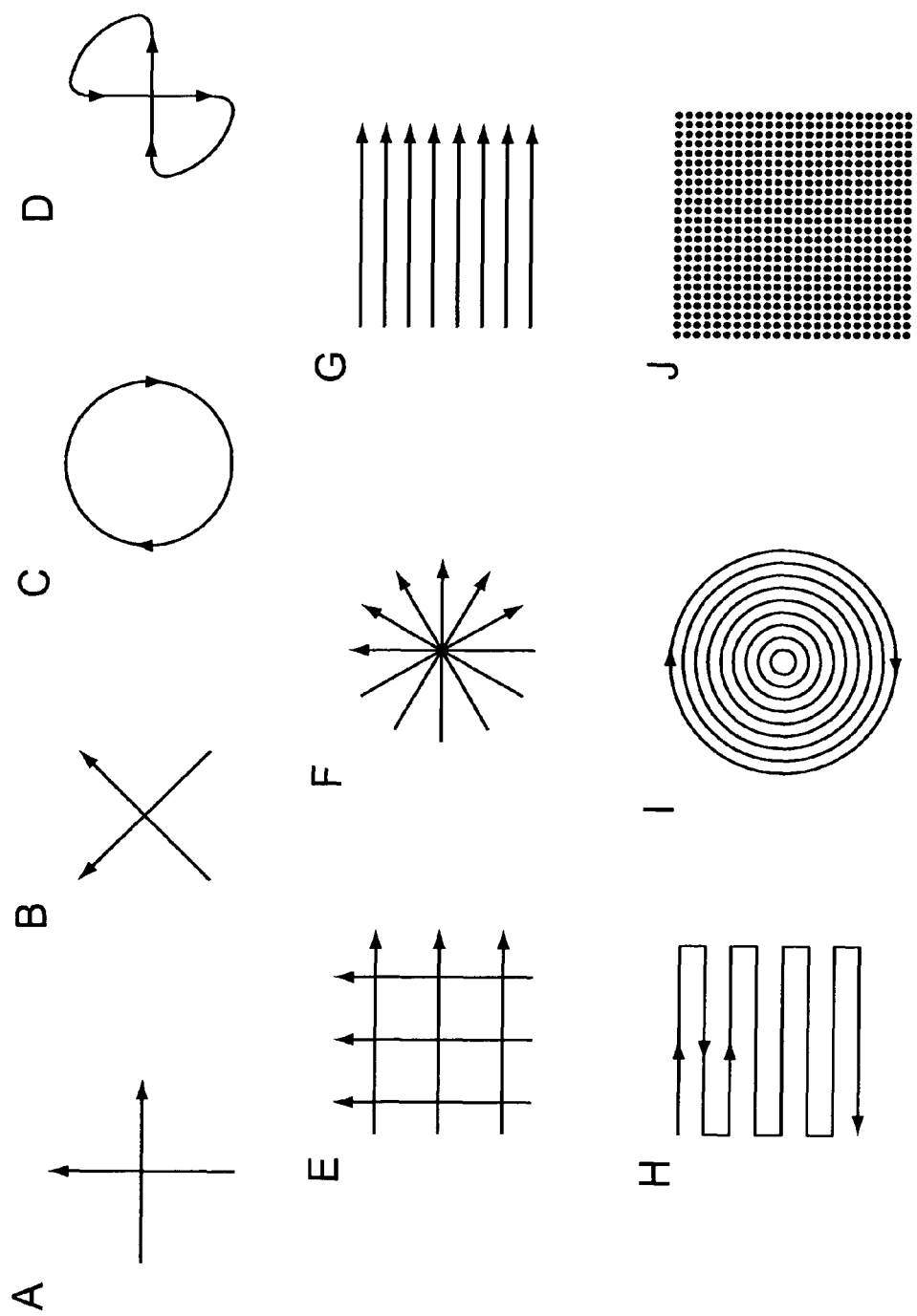
FIG. 3 is a set of ten schematic diagrams depicting scan patterns for survey/registration scans according to an illustrative embodiment of the invention.

To provide suitable feature or landmark information for directing or aiming the OCT beam scanning for data acquisition, the survey/registration scans are performed so that they measure different transverse cross sections in the sample, such that the scan positions in the transverse plane are not along a single line. Several possible survey/registration scan patterns labeled A-J are shown in FIG. 3. The survey/registration scan pattern may include two OCT scans performed along different directions (A, B) where the scans are either intersecting or not intersecting (not shown). The survey/registration scan may also be a single scan such as a circle (C) or continuous curve (D). The survey/registration scans may be a set of multiple lines with different positions (E) or orientations (F), a unidirectional raster scan (G), a bidirectional raster scan (H), or series of circular scans (I). Finally, the survey/registration scan pattern may include sets of axial scans measured at different transverse positions on the sample (J). Survey scans can be used to accurately determine the position of features or landmarks for the purpose of directing or aiming the OCT beam scanning so that the OCT data is accurately registered with respect to features or landmarks in the sample. Additionally, in some embodiments, survey scans are used to assess a large region of the sample to locate features or landmarks.

Fiducial Position/Landmark Analysis

Referring back to FIG. 2, the survey/registration OCT scan or scans are a set of axial scans, which represent measurements of the sample as a function of depth at different transverse positions. The survey/registration scans are performed in a location of the material or tissue which contains features or landmarks. In the case where the survey/registration scan pattern is a line or continuous curve, the set of axial scans represents a cross-sectional image through the sample. A computer or analyzer is used to analyze the survey/registration OCT scans to determine the position of features or landmarks in the survey/registration scans which correspond to the position of features or landmarks in the sample 12b. The landmarks need not be directly represented in the survey/registration scan data, but may be a landmark whose position is measurable or can be estimated from the data. Examples of survey/registration scans and feature/landmark analysis are presented in later sections. Once a landmark has been located additional analysis may be performed to verify its accuracy 12c. The location of the landmark (fiducial position) is used to aim the subsequent OCT beam scanning for OCT data acquisition. In other embodiments of intelligent scanning, the location of features or landmarks is used to identify a region of interest of the sample and to direct OCT beam scanning or to control the actuation of aiming and other operating parameters in the OCT instrument.

Iteration of Survey/Registration Scanning and Feature/Landmark Analysis

In some cases, where the features in the sample have a high degree of symmetry or are well defined, the position of the landmark can be established with sufficient accuracy using a single set of survey/registration scans. However, in many cases iteration of the survey/registration scanning and feature/landmark analysis is required. This is shown by the conditional branch in the flow chart of FIG. 2. The position of the landmark from the survey/registration scan or scans is used to aim the OCT beam 12d and acquire another set of survey/registration scan or scans which are better positioned to enable determination of the landmark with improved accuracy. This process can be iterated until it is determined that sequential survey/registration scans and landmark locations are within acceptable error bounds. An example of iterative survey/registration scanning and feature/landmark analysis is presented in later sections.

Directing/Aiming OCT Beam Scanning and OCT Data Acquisition

Figure 4:
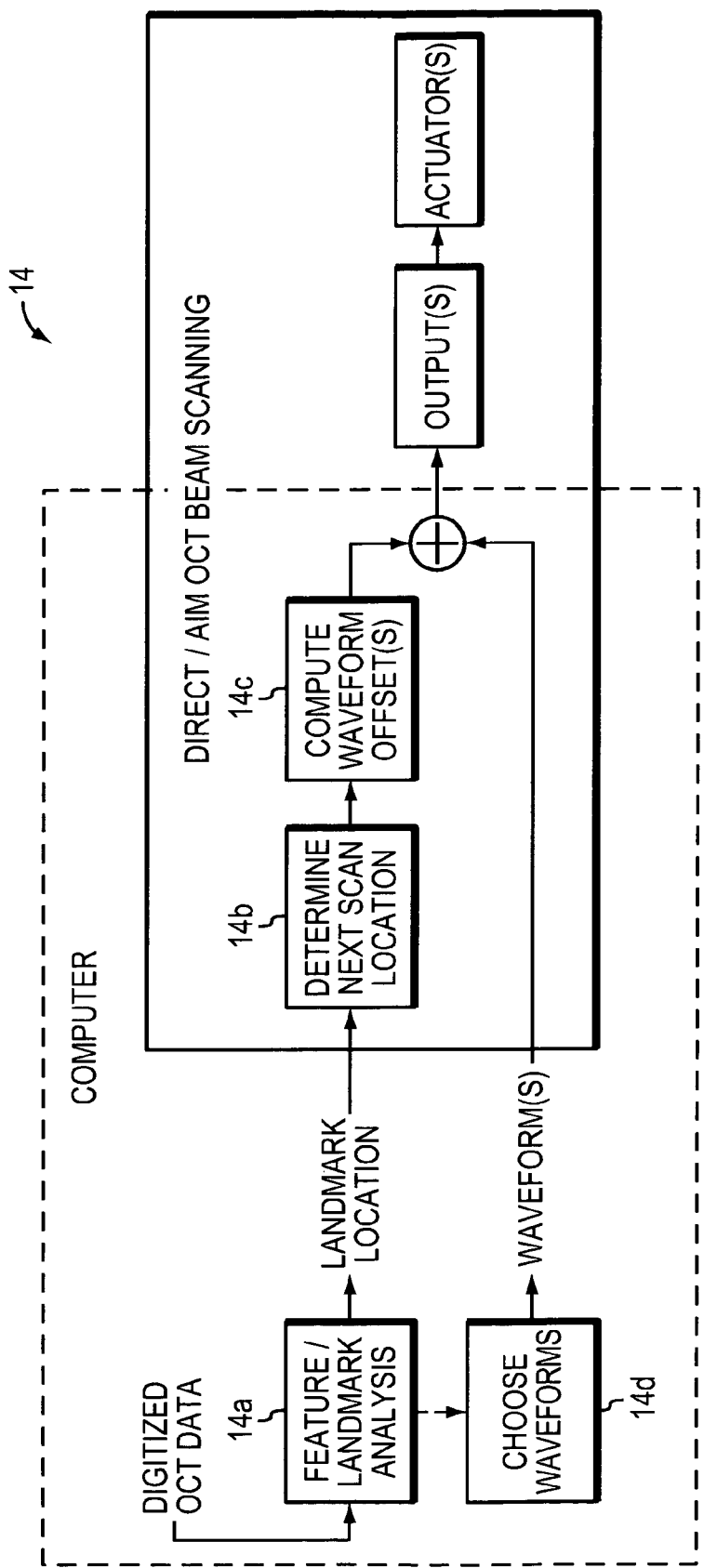
FIG. 4 is a flow diagram depicting data flow for feature/landmark analysis and aiming according to an illustrative embodiment of the invention.

The procedure of survey/registration scanning and feature/landmark analysis, or its iterative application, accurately determines the position of a landmark in the sample. The position of this landmark is then used to direct or aim the OCT beam scanning 12e. OCT beam scanning is performed by actuating mirrors or other beam scanning or positioning mechanisms using waveforms for OCT data acquisition 12f. FIG. 4 shows an example of a flow chart representing an exemplary method 14 for aiming the OCT beam scanning for OCT data acquisition. As part of the method digitized OCT data is used as part of the feature/landmark analysis process 14a discussed above. The position of the landmark in the sample is used to determine the location of the next OCT scan relative to the landmark 14b. The next OCT scan may be either a survey/registration scan, or an OCT data acquisition scan. The location for the next scan is then used to compute an offset 14c which is applied to choose suitable waveforms, typically using a controller, 14d which drives the OCT beam scanning mechanism. This results in registration of the OCT data with respect to the landmark in the sample. Thus, each axial scan in the OCT data set can be related or registered to a known transverse position of the OCT beam on the sample and therefore measures as a function of depth at a known transverse position on the sample. In other embodiments, a data acquisition scan is initially performed and if the data quality degrades or errors develop, a survey scan is performed to realign the OCT scans relative to a landmark or fiducial position.

Although this procedure of survey/registration scanning and feature/landmark analysis can be used for aiming of the OCT beam scanning and data acquisition, as shown in FIG. 4, the survey/registration scans and feature/landmark analysis can be used to direct the OCT data acquisition in other ways. For example, this procedure may be used to determine what type of OCT beam scan pattern should be subsequently performed. This procedure can also be used to set other parameters in the OCT apparatus, including but not limited to, position and angle of the OCT beam scanning (actuating four parameters), the position of the sample, the reference delay or axial measurement range, and/or the focus of the OCT beam. This procedure may also be used to direct or control the mode of operation of the OCT apparatus. For example, the mode of operation may be changed to "enhanced performance" mode based on the survey/registration scans and feature/landmark analysis.

Iteration of Scans and Analysis to Test Registration Accuracy of OCT Data

Figure 5:
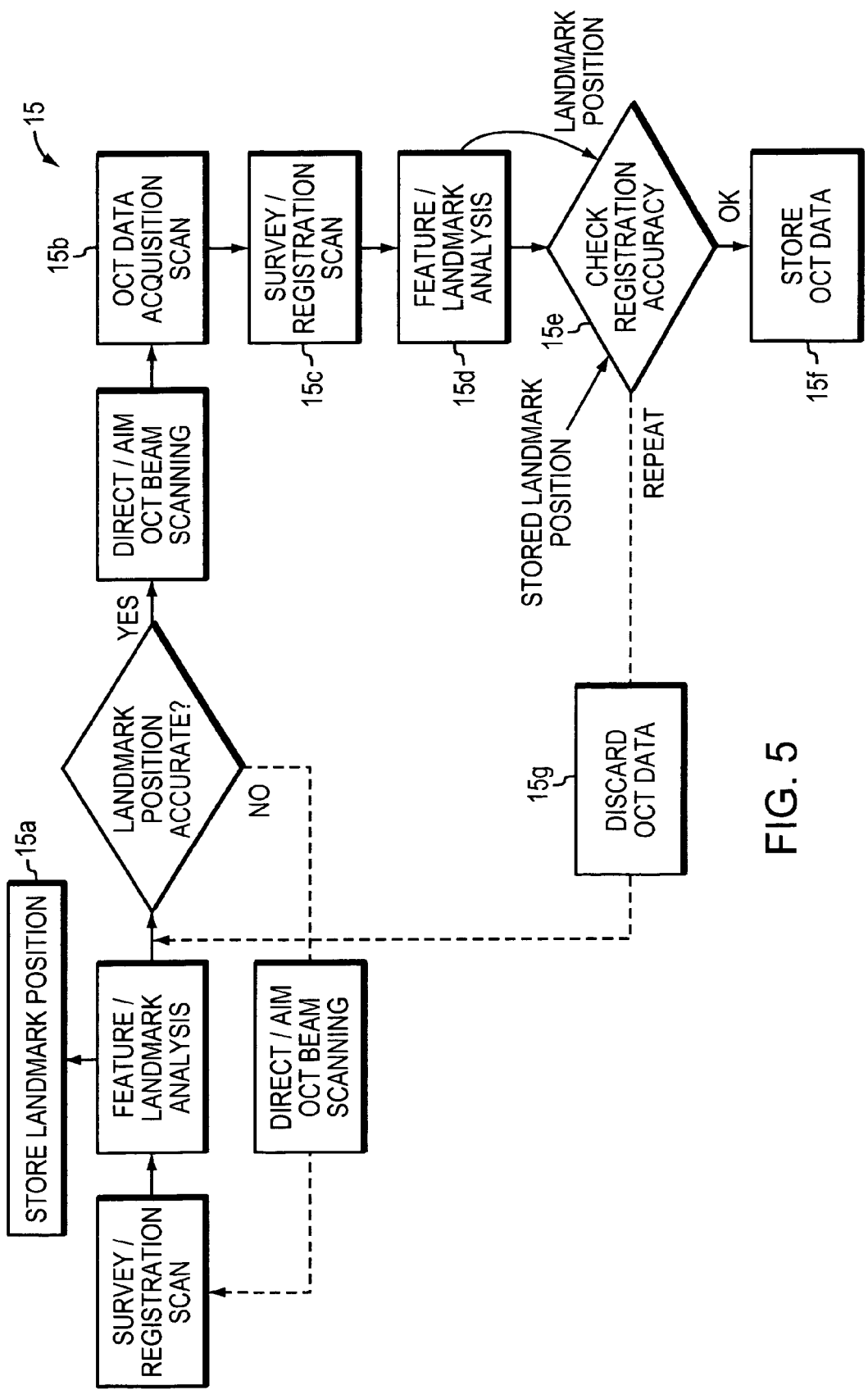
FIG. 5 is a flow diagram depicting a method for OCT intelligent scanning that verifies registration accuracy according to an illustrative embodiment of the invention.

In some applications it is desirable to test the registration accuracy of the OCT data with respect to the sample. If motion of the sample has occurred, then it may be desirable to re-scan the OCT data so that it is free from motion errors and registered to within a desired accuracy. This may be performed by iterating the procedure of survey/registration scanning and feature/landmark analysis, after the OCT data has been acquired as shown in FIG. 5. The location of the landmark, determined from the previous survey/registration scan which was performed before the OCT data scans, such as depicted in FIG. 2, is stored 15a.

After OCT data acquisition 15b, the process of registration/survey scans 15c and feature/landmark analysis 15d is repeated. The newly measured position of the landmark is compared to the previously stored position measured prior to the OCT data acquisition 15e. A change in the measured position of the landmark indicates that sample has moved with respect to the OCT apparatus. If the change in the measured landmark position is within acceptable error bounds, this indicates that the OCT data is registered to the landmark in the sample within the desired accuracy and OCT data is stored 15f. Conversely, if the change in the measured landmark position is too large, this indicates that there has been an unacceptable amount of relative motion of the sample with respect to the OCT instrument during the OCT data acquisition, and the OCT is not registered to the sample with the desired accuracy and has motion error. In this case, the OCT data is discarded 15g, and the new landmark position information is used to re-aim the OCT beam scanning for OCT data acquisition of a new data set.

In addition, it is possible to perform landmark analysis on data acquired during the data acquisition scan and use it to aim subsequent data acquisition. (i.e., to use data acquired during the data acquisition scan as the OCT data input to FIG. 4) Landmark analysis and aiming may be performed on this data.

OCT Intelligent Scanning Apparatus

OCT scanning is performed by scanning the OCT beam on the sample. Typically a controller/processor such as a computer outputs control signals or waveforms which drive actuators that scan the OCT beam. OCT beam scanning is usually performed using angle-actuated mirrors which vary the angle of the OCT beam, and thereby scan the transverse position of the OCT beam on the sample. However, other scanning methods are also possible. The OCT apparatus measures the magnitude and delay of backscattered or backreflected light from the sample. This data is called an axial scan or A-scan, and is a set of data points that carries information about the backscattered or backreflected light as a function of depth in the sample. Each axial scan measurement is performed when OCT beam is directed at a given transverse position on the sample. The reference delay may also be actuated. This reference delay setting determines the measurement range of OCT in the axial direction, along the axis of the OCT beam.

Figure 6A:
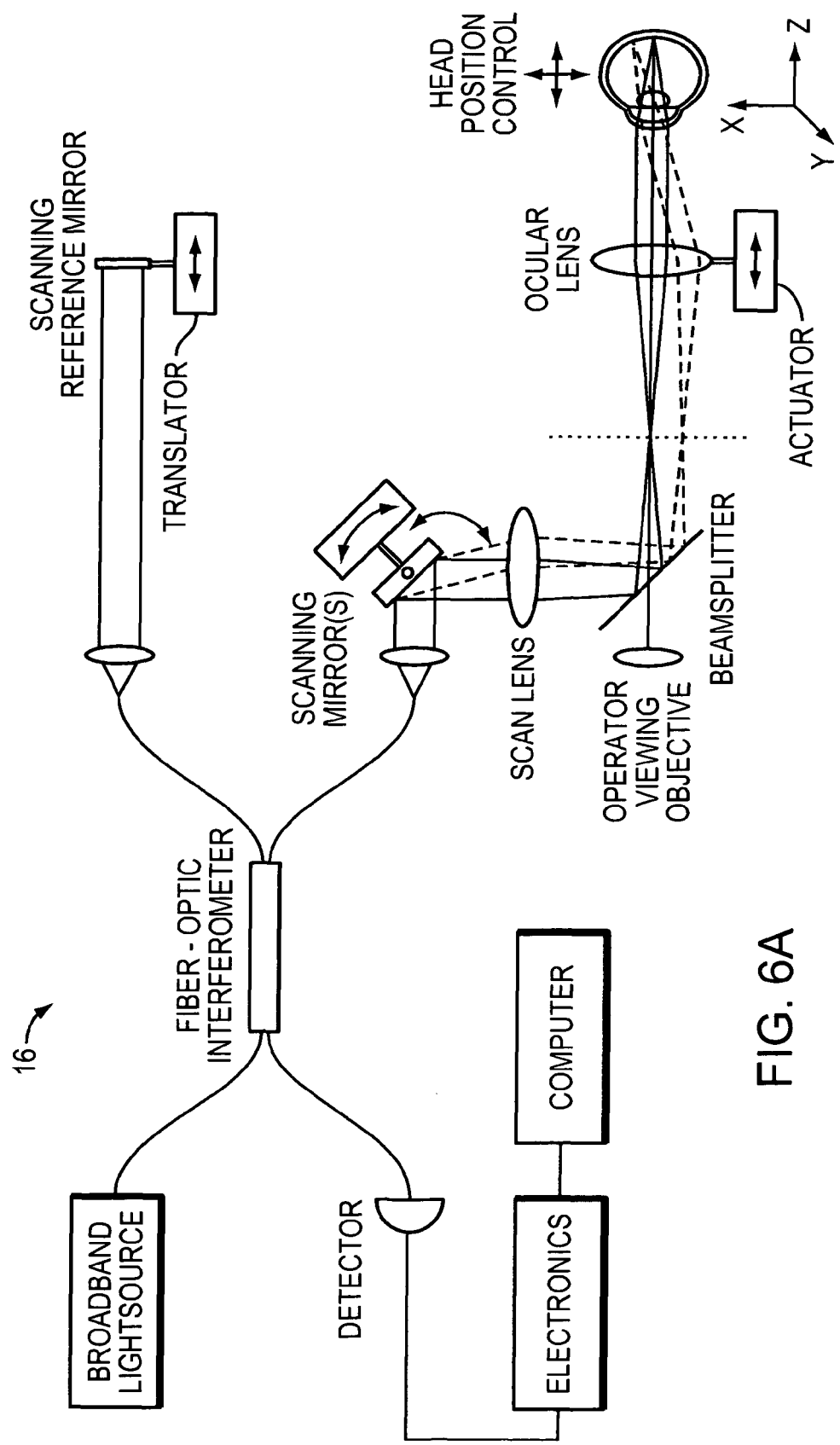
FIGS. 6a-6c are schematic diagrams depicting embodiments of an intelligent scanning OCT apparatus according to illustrative embodiments of the invention.
Figure 6B:
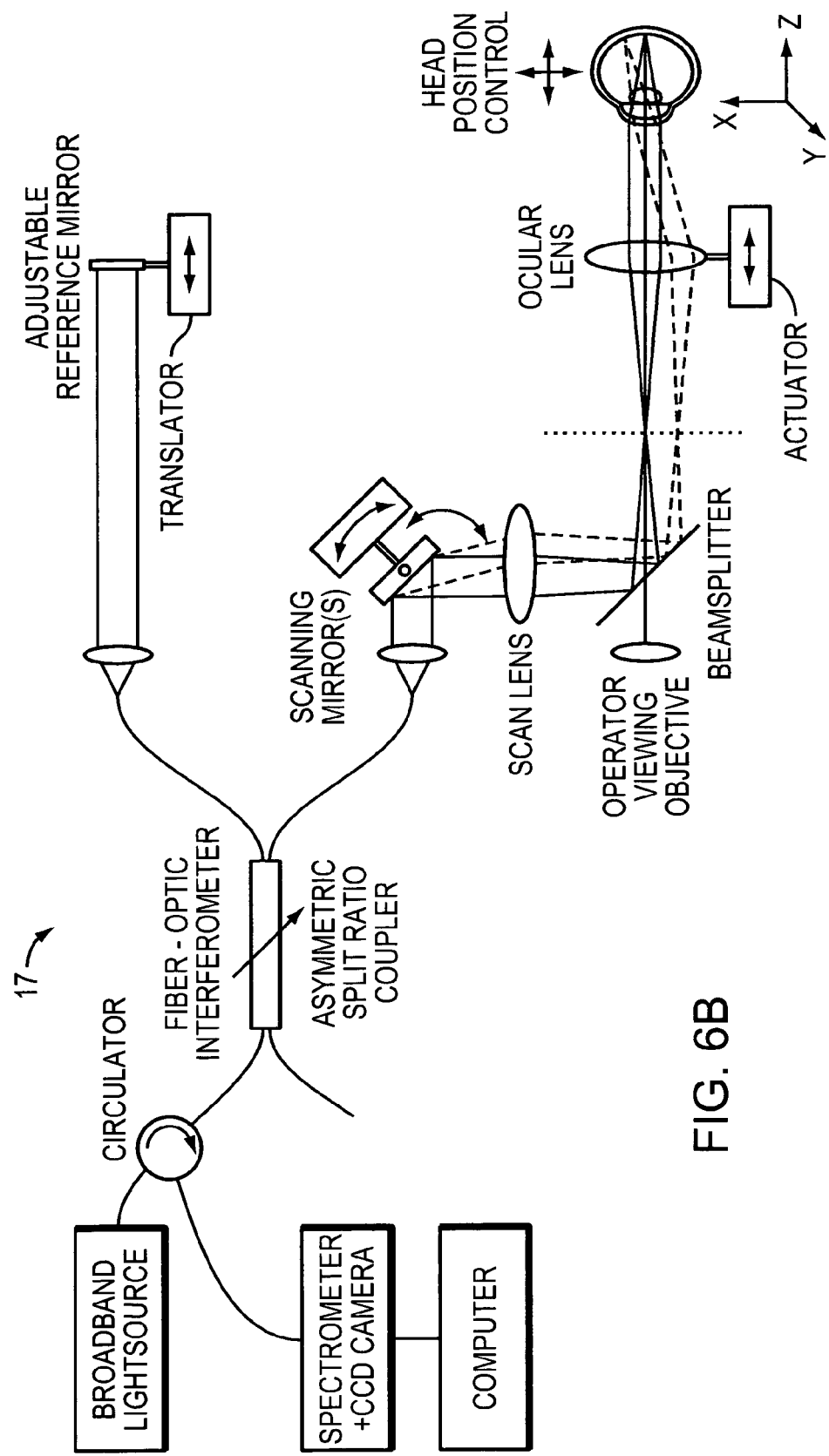

There are three general types of OCT detection systems. As shown in FIG. 6A, one system 16 uses an interferometer with a broadband light source with a scanning reference delay and a detector or set of detectors to detect interference of the backscattered or backreflected light from the sample with light from a scanned reference path. In FIG. 6B, another system 17 uses an interferometer with a broadband light source with adjustable reference delay, setting the range of depth measurement, and a spectrometer with a high-speed detector array to detect interference of light from the sample and reference paths. This is known as Fourier domain OCT, spectral domain OCT, spectral radar, or by other names in the art. Still another system 18, shown in FIG. 6C, uses an interferometer with a tunable, narrow band light source, with an adjustable reference delay, and a detector or set of detectors to detect interference of light from the sample and reference paths. This is known as Fourier domain OCT, swept source OCT, optical frequency domain imaging or by other names in the art.

Figure 6C:
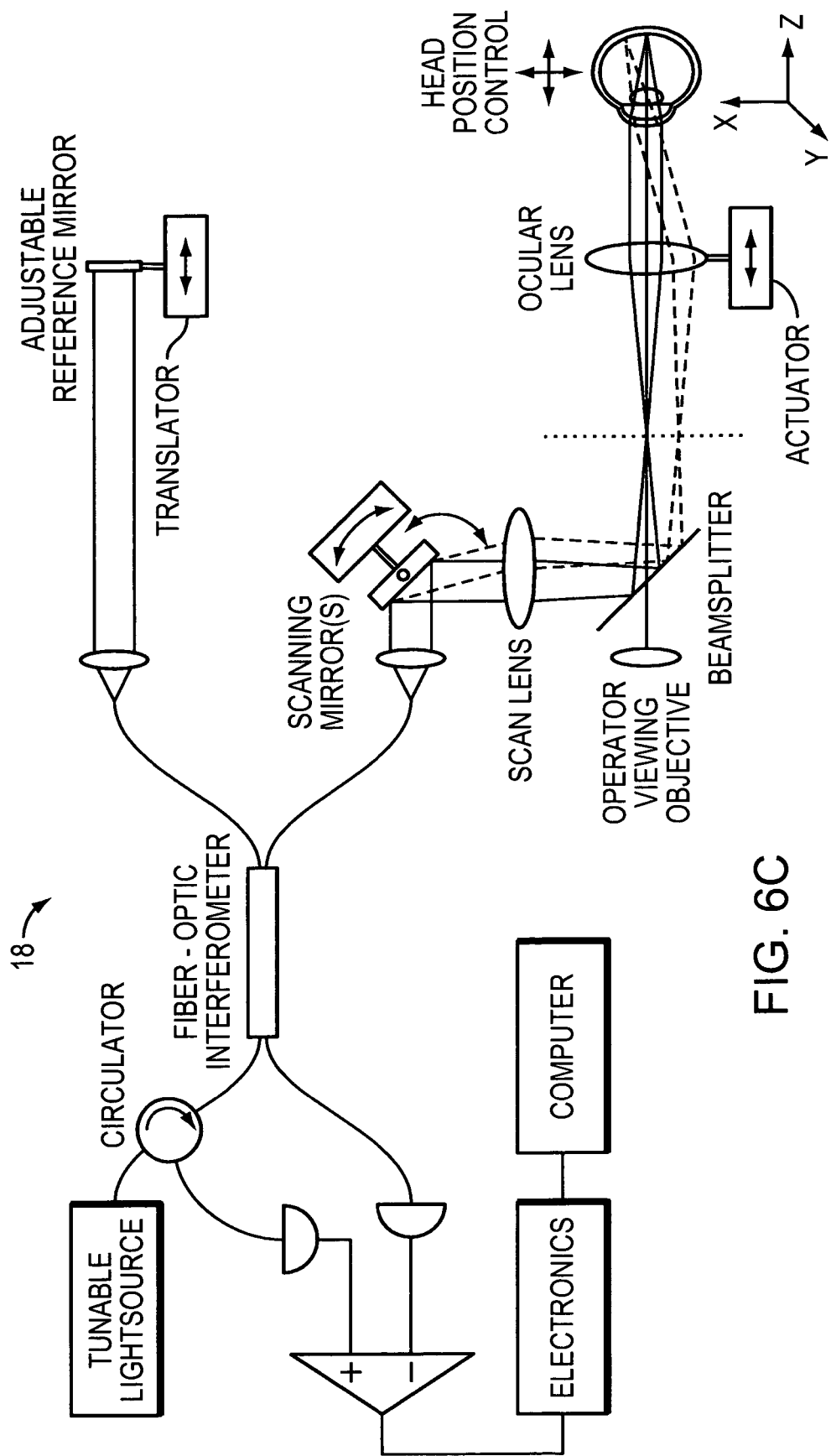

Many different interferometer configurations are possible, including those using multiple couplers, higher-order couplers, or circulators, as well as those using dual-balanced detection. FIG. 6a shows an interferometer with a single splitter. FIG. 6b shows an interferometer with a circulator which is used to improve the efficiency of power transmission from the light source and the detection efficiency. FIG. 6c shows an interferometer with a circulator which is used with dual detectors to cancel excess noise in the light source and improve efficiency. Other interferometer configurations may be used to practice the invention.

The scanning mirrors, ocular lens, and reference delay are actuated by actuators which are driven by control signals or waveforms generated under computer control. Actuation of additional parameters is possible. These include the positions and orientations of optical elements and assemblies of optical elements, the position and orientation of the sample, and the position and orientation of a fixation target which can direct the gaze of the subject in ophthalmic OCT. Fast actuation, such as through angle scanning mirrors, is typically used to scan the OCT beam for data acquisition.

However, slower actuation, such as actuation of the position of the sample, may be used to coarsely direct the OCT beam scanning onto a region of interest or to ensure that the sample is within the transverse and axial measurement range of the instrument. In general, intelligent scanning may be applied to control any parameter of the OCT system (a given OCT system typically includes the light source, optics, detection electronics and software, and processing software) using the methods described. While FIGS. 6a-6c show embodiments of intelligent scanning OCT systems in ophthalmology, the method described here is applicable to any OCT system apparatus.

Intelligent scanning may be applied to existing OCT systems, but may also be used in systems that perform automated functions which human operators cannot perform. This will enable novel OCT devices to be deployed in a wide range of new applications as well as enhance the capabilities of OCT in current applications. Examples of new devices include, but are not limited to: an intelligent OCT retinal screener, an intelligent hand-held OCT ophthalmoscope, and an intelligent OCT microscope.

Intelligent OCT scanning enables a handheld OCT ophthalmoscope because it aims the OCT data acquisition scan rapidly before appreciable subject motion has occurred. Without intelligent OCT scanning, it would be difficult to reliably aim and acquire data using a handheld device. Intelligent OCT scanning also enables the development of an intelligent OCT retinal screener where aiming, data acquisition, and assessment of data registration accuracy or motion error can be performed without the need for expert operator guidance. This enables new OCT instruments which can be used in screening applications and do not require highly trained personnel to operate the OCT-instrument.

Intelligent Hand-Held Ophthalmoscope

Figure 7A:
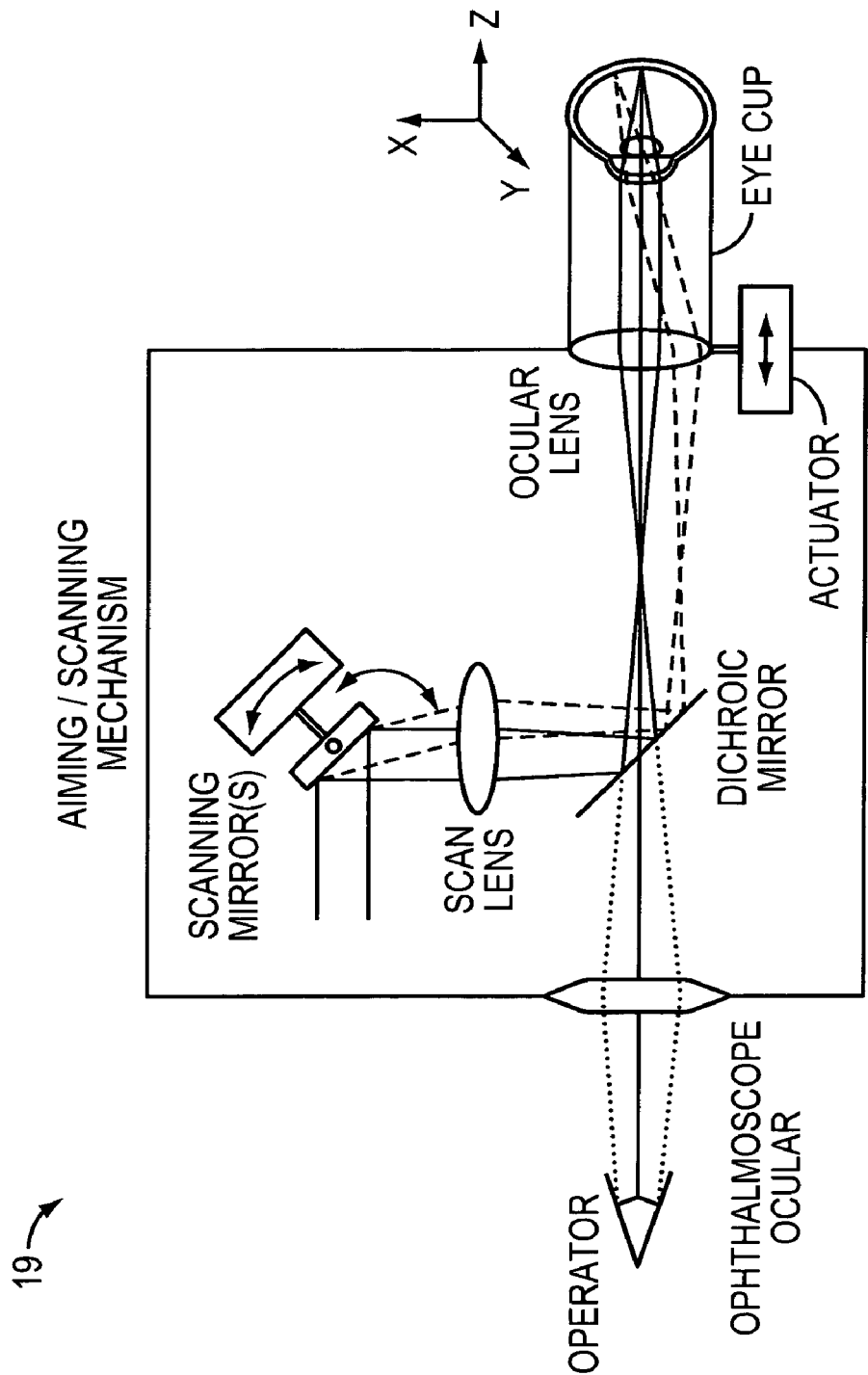
FIGS. 7a-7c are schematic diagrams depicting intelligent OCT handheld ophthalmoscopes according to illustrative embodiments of the invention.
Figure 7B:
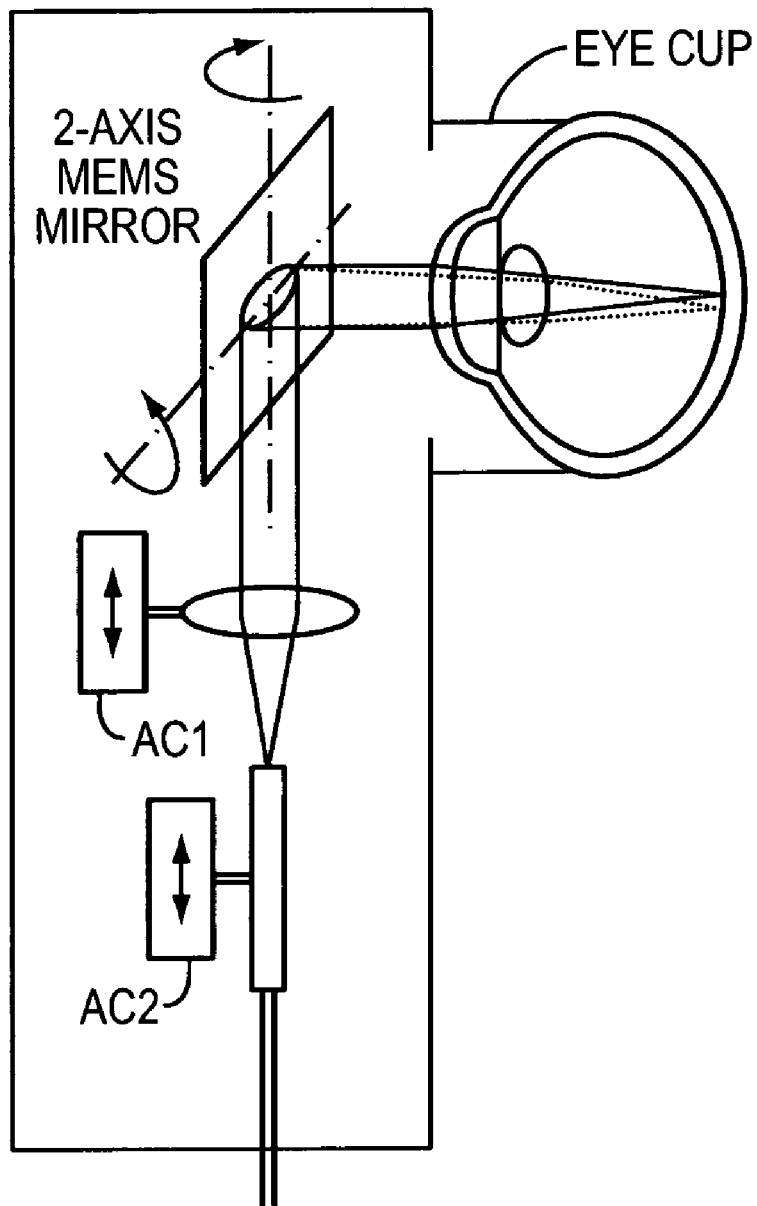

The intelligent hand-held OCT ophthalmoscope expands on the functions of a direct ophthalmoscope by enabling OCT data and image acquisition. The handheld instrument may be used to provide a standard ophthalmoscopic view of the retinal fundus. The instrument can be coarsely aimed by the operator with fine aiming using intelligent scanning; or aiming may be performed entirely using intelligent scanning. FIG. 7A depicts an aiming/scanning mechanism 19 for an intelligent hand-held OCT ophthalmoscope. FIG. 7B depicts a compact, side imaging ophthalmoscope 20 and FIG. 7C depicts a compact, forward imaging ophthalmoscope 21.

The aiming/scanning mechanism may include X-Y scanning mirrors and an ocular lens, which are actuated under computer control as shown in FIG. 7A. A collimated beam is incident on the scanning mirrors, which are angle actuated to deflect the beam and achieve beam scanning. The scanning mirrors are approximately imaged to the pupil plane of the eye, such that as the beam is scanned a collimated beam pivots on the pupil.

Figure 7C:
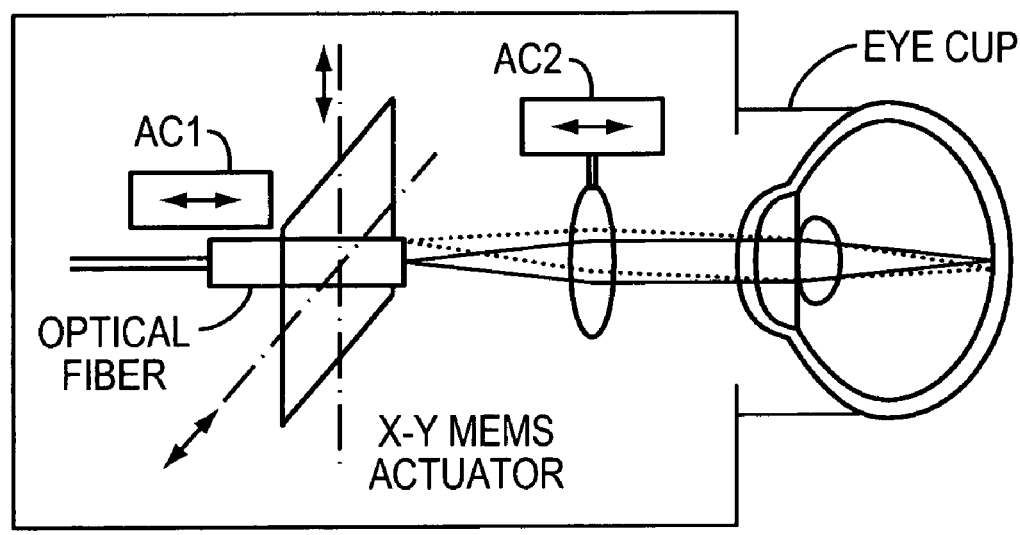

Two new embodiments using MEMS or other small mechanical devices are shown in FIGS. 7B and 7C. These designs have the advantage that they provide a compact beam delivery mechanism and minimize the number of optical components. In the side scanning hand-held OCT ophthalmoscope 20, shown in FIG. 7B, a collimated OCT beam is directed onto a MEMS mirror that scans two angle axes. The angle scanner is used proximate to the cornea to enable scanning of the OCT beam and minimal vignetting by the iris.

The instrument may have an eye cup or other device which contacts the patient around the subject's eye to determine the coarse alignment of the instrument and help to stabilize the position of the instrument relative to the eye. The focus of the OCT optical beam on the retina may be adjusted by actuating the fiber or collimating lens positions. The forward scanning hand-held OCT ophthalmoscope 21 shown in FIG. 7C actuates the light source position to control the angle of the OCT beam that is emitted from the lens. This results in a scanning of the transverse position of the beam on the retina. The device is used proximate to the cornea to minimize vignetting by the iris. The fiber or collimating lens positions may be actuated to control the focusing of the OCT beam on the retina.

Intelligent OCT scanning is used to determine the regions for OCT data acquisition and can automatically direct or aim the OCT beam scanning. Intelligent scanning may also be used to adjust the focus, and adjust the reference delay or axial measurement range. The intelligent hand-held OCT ophthalmoscope may also provide a simultaneous view of OCT images or processed data, enabling alignment of the instrument by the operator. Intelligent scanning may be used to compensate for eye motion during data acquisition. It is possible to use intelligent scanning to check the accuracy of the location of data/image acquisition, and repeat the process of data/image acquisition, if necessary.

Intelligent Retinal Screener

Figure 8A:
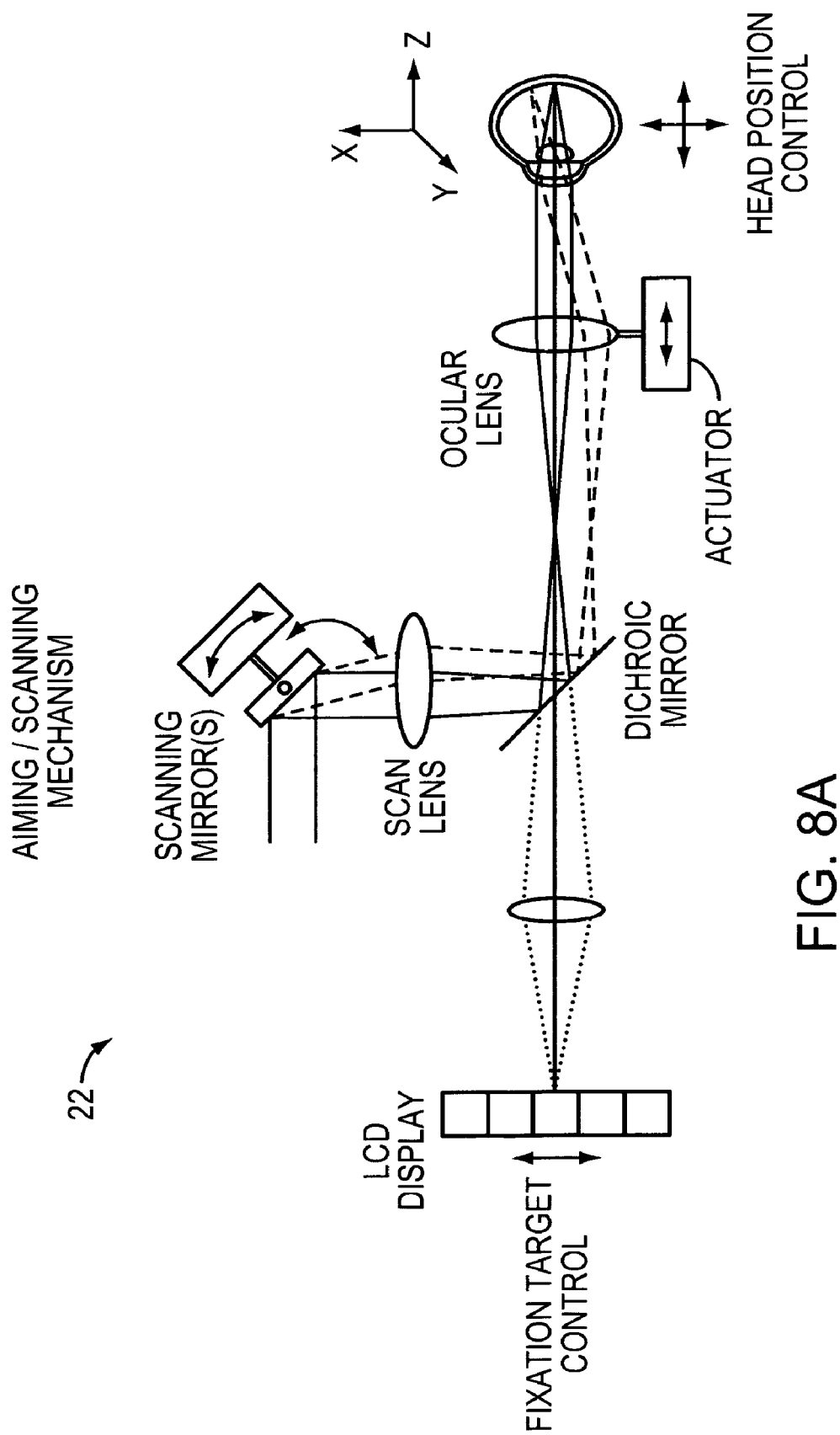
FIG. 8a is a schematic diagram depicting an intelligent OCT retinal screener according to an illustrative embodiment of the invention.

The intelligent OCT retinal screener device 22 in FIG. 8A enables OCT data or image acquisition to be performed with little or no supervision by a trained operator. This will enable screening applications of OCT and other applications outside of the clinical specialist environment. The OCT beam aiming/scanning mechanism may include angle-actuated, X-Y scanning mirrors as shown in FIG. 8A. Other known actuators and mechanisms may also be used for OCT beam scanning. The position of the ocular lens or other elements may be actuated to adjust the focus of the OCT beam on the retina.

Subject eye fixation control refers to directing the subject gaze to look in a particular direction, which may be required for OCT data acquisition. Subject eye fixation helps aim the OCT beam through the pupil of the eye and onto a desired region of the retina. An LED panel, LCD display or other display device may be used to direct the subject's gaze and to display instructions for the subject as shown in FIG. 8A. The position of a fixation target on the LCD display or LED panel may be directed under computer control. The use of a display has the advantage of flexibility; multiple targets or patterns of different colors and intensities may be imaged onto the eye. In addition, as shown by system 23 in FIG. 8B, an angle-actuated scanning mirror or mirrors may be used to change the position of a fixation target, thereby directing the subject's gaze. The OCT beam itself may also be used to direct the subject's gaze. By controlling the intensity and scanning pattern of the OCT beam, patterns, figures, or letters can be projected directly onto the subject's retina. Generating fixation targets with the OCT beam scanning has the advantage of ensuring alignment of the subject's pupil to the scanned OCT beam, since if the subject can see the OCT beam scan pattern, then the OCT beam is aligned to pass through the pupil.

Focusing of the retinal screener may be performed by the subject directly or automatically by assessing the sharpness or signal intensity in the OCT data. The retinal screener may be integrated with a fundus camera, and may enable the acquisition of fundus photographs in addition to OCT images or data. This device has the advantage that it may be used outside of a clinical specialist environment. One possible application of the retinal screener is in screening for diabetic retinopathy, where measurement and mapping of retinal macular thickness is an important diagnostic indicator.

Both the intelligent OCT retinal screener and the intelligent hand-held OCT ophthalmoscope offer the capability to automatically analyze acquired data and generate OCT images, maps, renderings, or other visualizations of OCT data. In addition, quantitative measures may be compared to normative databases and statistics may be automatically generated.

Beam Positioning and Scanning Apparatus Designs

FIGS. 9A-9D show examples of embodiments of apparatus designs for controlling positioning and scanning the OCT beam on the retina with intelligent OCT scanning. While the figures show control of one transverse axis, these designs may be trivially applied to two-axis beam positioning and scanning. The designs depicted here may be applied to any of the devices discussed in this disclosure or may be used in other devices.

A simple design, shown in FIGS. 7A and 8A, uses scanning mirrors to change the transverse position of the beam on the retina by angle scanning the beam about the iris, and translating the ocular lens to change the focusing. This configuration has the limitation that the pivot point of the scanned beam is set by position of the ocular lens. In this configuration, the pivot point is defined as the position where the scanning mirror is imaged. As the angle of the beam is changed by the scanning mirror, the beam remains centered on the pivot point. To minimize vignetting and aberrations, the pivot point should be in the pupil plane and centered on the pupil of the eye. In systems with two scanning mirrors, there are actually two pivot points separated by a distance proportional to the separation of the two scanning mirrors so it will not be possible to place both pivot points exactly in the pupil plane of the eye.

Vignetting occurs when the scanned beam is blocked by the iris of the eye and results in lower signal and worse transverse resolution for large scan angles. To the extent that the pivot point is poorly centered on the pupil in the pupil plane, the signal and transverse resolution will be degraded as the incident beam is scanned and becomes vignetted or aberrated. In the emmetropic eye, setting the ocular lens to collimate the incident beam at the cornea results in focusing at the retina. In eyes that are not emmetropic, the position of the ocular lens is adjusted to focus the beam on the retina. This can move the position of the pivot away from the pupil plane, making vignetting more severe.

These alignment and focusing issues are especially important in OCT applications such as the intelligent hand-held OCT ophthalmoscope and the intelligent OCT retinal screener. In applications requiring a high degree of automation, it is desirable to be able to automatically detect vignetting or suboptimal focusing at the retina, and to adjust instrument parameters to correct these events. In addition, it is desirable to control the beam pivot position and focus independently, so that the focus and pivot point may be set arbitrarily.

The problems discussed in the preceding paragraph may be solved by intelligent OCT scanning control of scanning parameters. The most general type of scanning achieves complete control over the transverse position, focus, and the direction of the OCT beam, enabling the position of the beam scanning pivot point and the beam focus to be independently controlled. FIGS. 9A-9D show designs for achieving independent control over the transverse position and direction of the OCT beam. In all cases shown in FIGS. 9A-9D, the focus may be set by changing the ocular lens position.

Figure 9A:
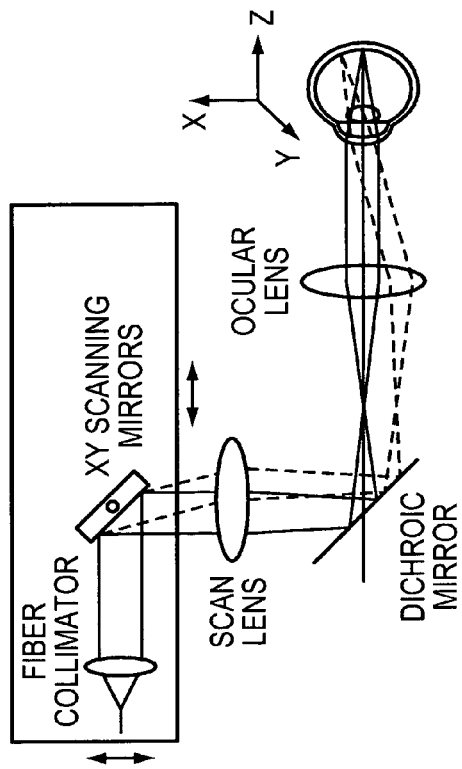
FIGS. 9A-9D are schematic diagrams depicting aiming/scanning mechanisms according to illustrative embodiments of the invention.
Figure 9B:
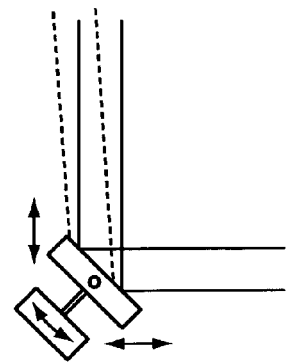
Figure 9C:
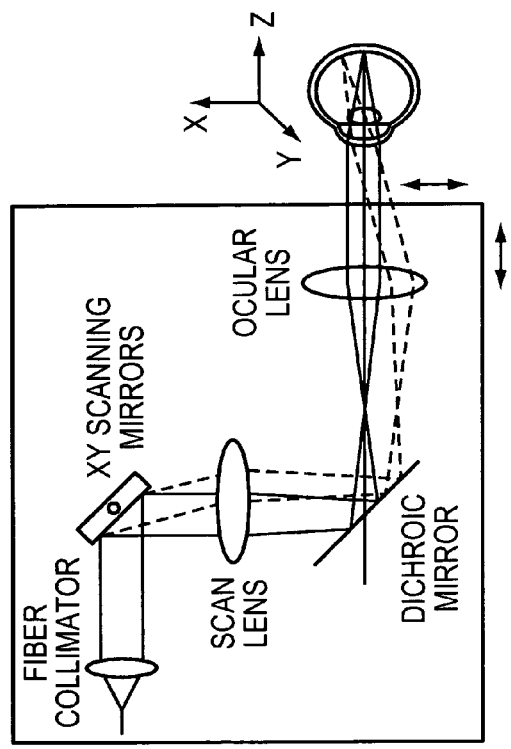
Figure 9D:
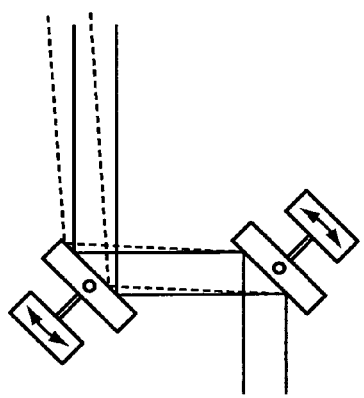

One way to set the pivot point of the scanned beam is to translate the complete optical assembly as shown in FIG. 9A. Another way to set the pivot point of the scanned beam is to translate the combination of the fiber, collimating lens, and X-Y scanning mirror assembly so that the position of the image of the scanning mirror (which determines the pivot point of the beam) is translated, as shown in FIG. 9B. Another design to achieve control over the position and direction of beam incident on the cornea, shown in FIG. 9C, uses two scanning mirrors for each transverse direction. For two-axis control (X and Y), a total of four scanning mirrors are required. Two dual-axis mirrors separated by some distance may be used to achieve the same effect. Another design shown in FIG. 9D uses one scanning mirror for each axis. The scanning mirror's position and deflection angle may be varied to achieve control over the location of the pivot point. For transverse scanning along two axes, two single-axis scanners may be used with actuators for translation of each scanner. It is also possible to perform beam scanning using methods other than angle controlled mirrors, such as by mechanically actuating an optical fiber or fiber-lens assembly. These designs, in conjunction with the translation of the ocular lens, allow setting the pivot point and focus of the scanning beam in three-dimensions. Some of the embodiments described above result in changes in the total path length as the beam is scanned. Therefore, adjustment of reference delay or measurement range may be required.

In addition to control of parameters of the optical beam delivery system, the aiming/scanning mechanism may directly or indirectly cause translation or rotation of the tissue/material. One example of this aiming or scanning mechanism in ophthalmology uses a fixation target to direct the gaze of the subject, thereby changing the position and/or angle of the sample. Yet another embodiment in ophthalmology translates the chin rest or otherwise translates/rotates the subject relative to the OCT beam.

With the ability to achieve an arbitrary angle of incidence and position of the optical beam on the cornea, it is possible to control the beam position so that it is always centered on the pupil during OCT scanning. Setting of the focus and beam pivot is achieved by co-actuation of the scanning mirror angles of the deflection and translation of elements in the system and may be guided by using intelligent scanning to analyze acquired OCT data. In one of embodiment, the focus position may be optimized by maximizing the OCT signal level or maximizing high transverse frequency or edge components in an OCT image. In another possible embodiment, the focus may be optimized by maximizing the light reflected back from the sample. The beam pivot position may be optimized by minimizing vignetting in an OCT data or image set. Vignetting may be detected by performing survey/registration scans or data acquisition scans and analyzing the scans for the loss of signal at certain deflection angles. The presence of this feature in the OCT data or images indicates that the OCT beam may be vignetting on the iris. With knowledge of the scanning pattern, it is possible to determine how to translate the pivot point to achieve alignment by analyzing signal loss as a function of scanning angle. Vignetting may also be detected by analyzing only the light reflected back from the sample as the beam is scanned, similar to a scanning laser ophthalmoscope. An alternate method of detecting vignetting is tracking the location of cornea through interference of the incident beam with a second reference delay, or by a second OCT beam in focus at the cornea.

Intelligent OCT Microscope

Figure 10A:
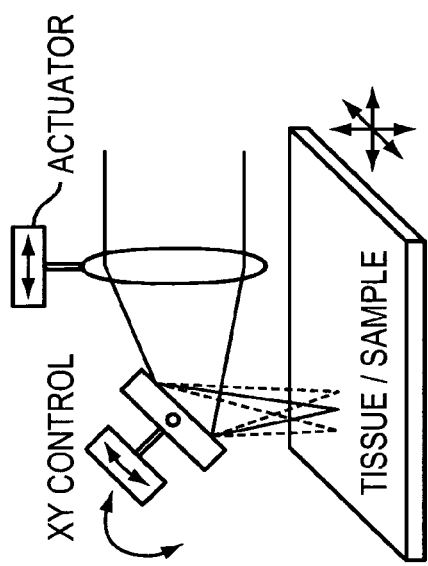
FIGS. 10A-10D are schematic diagrams depicting an OCT microscope and aiming/scanning mechanisms according to an illustrative embodiment of the invention.

One aspect of the invention relates to an OCT microscope that implements the method of intelligent scanning to direct data acquisition. Possible embodiments of the OCT beam aiming or scanning mechanism in an intelligent OCT microscope are shown in FIGS. 10A-10D. The aiming or scanning mechanism may include an objective lens position actuator, a beam deflection actuator mechanism, or a translation or rotation actuator for the sample. Transverse OCT beam scanning can be performed before or after the objective lens (pre- or post-objective) using angle actuation, or by translation of the sample. FIG. 10A shows a design for pre-objective beam scanning, where a collimated beam is deflected by angle-actuated scanning mirrors (not shown) to scan the OCT beam. The collimated beam is incident on an objective lens, which focuses the OCT beam on the sample at a transverse position that depends on the angle of the OCT beam.

Figure 10B:
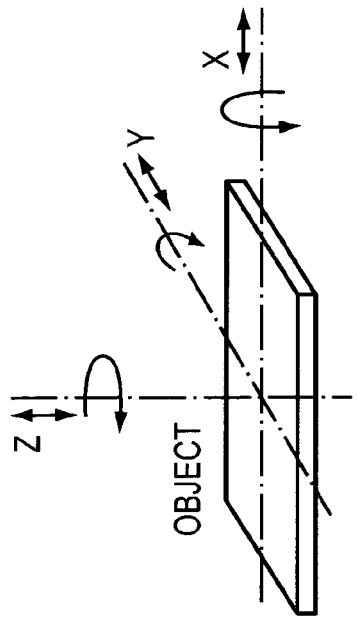
Figure 10C:
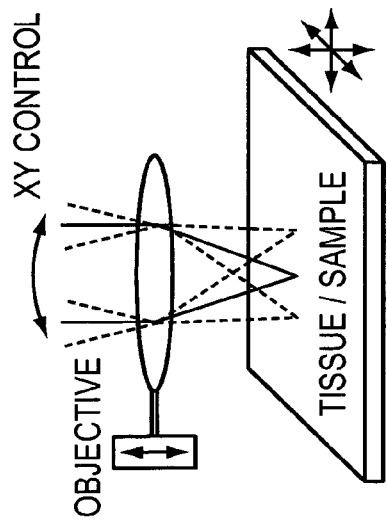
Figure 10D:
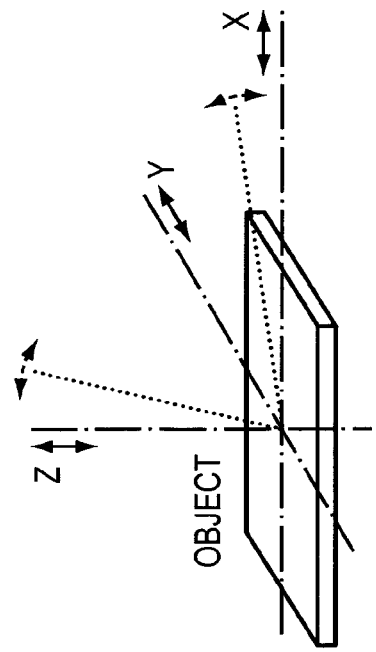

FIG. 10B shows a design for post-objective beam scanning, where the angle actuated, and scanning mirrors are placed after the objective lens in the optical path of the light incident on the sample. The angles of the scanning mirrors are actuated to deflect the OCT beam and control the transverse position on the sample. MEMS scanners may be used in either of these designs. The beam focus can be changed by translating the objective lens or by translating the sample. Other adjustments such as: translation of the optical assembly in the transverse or axial direction, rotation of the optical assembly, and translation or rotation of the sample may be used to optimize focusing and minimize unwanted reflections. In general, the sample may be actuated by varying the following parameters: the translation of the sample along three principal axes, as well as two angles describing the orientation, the angle of azimuth and the angle of elevation, as shown in FIG. 10C. In addition, rotation may be accomplished by rotating about two or more of the three principal axes, as shown in FIG. 10D. The optical delay between the sample and reference arms may also be changed by the aiming or scanning mechanism.

In addition to employing intelligent scanning to direct data acquisition, the intelligent OCT microscope may include additional features that enhance its imaging or measurement capabilities. In one embodiment, the focus position may be optimized by maximizing the OCT signal level or maximizing high transverse frequency or edge components in an OCT image. In another possible -embodiment, the focus may be optimized by maximizing the light reflected back from the sample. Focus tracking may be especially important in applications with high numerical aperture focusing where the depth of field is limited. The OCT microscope may be implemented as a hand-held device or as a tabletop instrument.

Detecting Disease, and Measuring and Monitoring Disease Progression

Using intelligent OCT scanning in the field of ophthalmology for glaucoma detection and monitoring is another aspect of the invention. In this application, it is desirable to quantitatively measure features in the retina which are indicators of the presence of disease and its progression. For example, OCT images of a cylindrical region around the optic nerve head are often acquired to measure the thickness of the retinal nerve fiber layer which emanates from the optic nerve head. The embodiment of the methods and apparatus described in this section have applications in ophthalmology, but are not limited to ophthalmology and apply to other clinical or material measurement situations as well. Additionally, the apparatus of the invention can be used to evaluate various tissues and other biological elements, suitable tissue or biological elements include, but are not limited to lens tissue, retinal tissue (nerve fiber layer, photoreceptors, retinal pigment epithelium, ganglion cell layer, nuclear layers, plexiform layers), gastrointestinal tissue (esophageal tissue, gastric tissue, colonic tissue), pulmonary tissue (bronchus, bronchioles) and cardiac tissue including vasculature.

In current OCT systems, aiming of the OCT beam scanning is performed by an operator who views the OCT beam as it is scanned on the retina. This method of directing or aiming the OCT beam scanning is subject to errors in the registration or positioning of the OCT beam scanning with respect to the exact position of the optic nerve head. As a result, there is an uncertainty or error in the position of the OCT data relative to the desired landmark or fiducial position on the retina. Since the features that are being analyzed in the resulting OCT images depend on the exact position of the OCT scan with respect to the optic nerve head, variations in the images and the measured features (for example nerve fiber layer thickness measurements) can result. These variations can be detrimental to the diagnostic and monitoring application. In diagnostic applications, OCT measurements are often compared between different subjects. For example, in glaucoma diagnosis, the thickness of the nerve fiber layer measured by OCT is compared to a database which represents the distribution of normal thicknesses in the population.

Furthermore, in applications such as glaucoma detection and monitoring, it is desirable to quantitatively track retinal changes over a period of time. Patients are measured on several independent visits to the clinic spanning a period of months or years. In this case, variations in the scan locations across multiple scan sessions decrease the reproducibility of quantitative measurements and therefore compromise the ability of OCT to detect and assess the progression of glaucoma or other diseases.

Intelligent OCT scanning addresses these problems by enabling precise and repeatable registration of OCT scans. OCT scans can be precisely registered with respect to landmarks on the retina, which can be chosen so this registration is reproducible over long periods of time. Examples of landmarks in the eye are discussed in more detail below with respect to FIGS. 11A-11B. In turn, exemplary embodiments for performing landmark analysis in the eye are shown in FIGS. 12A-12D.

Figure 12B:
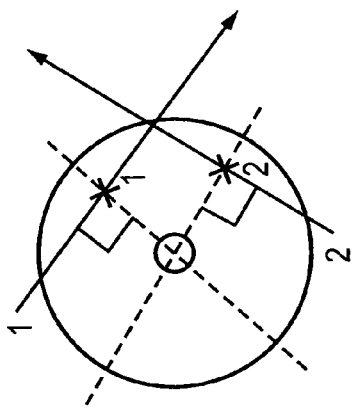
FIGS. 12A-12D are schematic diagrams depicting landmark analysis examples according to an illustrative embodiment of the invention.
Figure 12D:
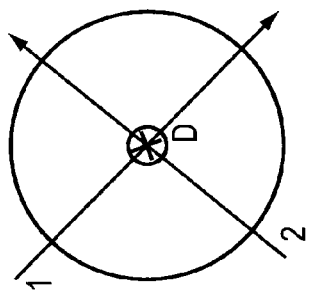
Figure 12A:
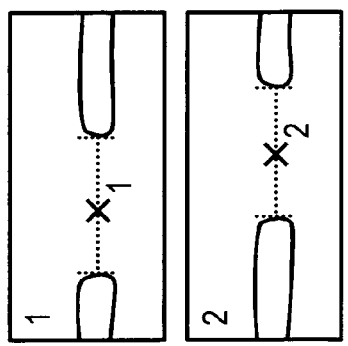
Figure 12C:
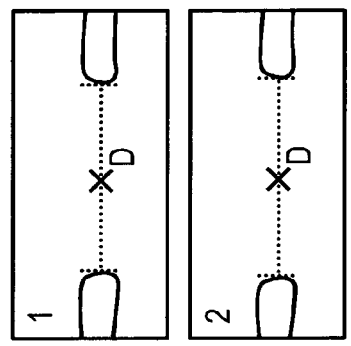

As described above, prior to landmark or fiducial position analysis, survey/registration scans are performed. The survey/registration scans are acquired and processed rapidly in comparison to any subject's motion. In the survey scan embodiments shown in FIGS. 12A-12D, the OCT beam is scanned across the optic nerve head to detect features which can establish the center of the optic nerve head as a landmark. FIGS. 12B and 12D correspond to the first and second scans that yield the corresponding cross-sectional views in FIGS. 12A and 12C, respectively. In one embodiment, survey/registration scans are performed by scanning the OCT beam to generate two distinct non-parallel OCT images as shown in FIGS. 12A and 12C. The initial positioning of the survey/registration OCT scans can be performed according to standard ophthalmic imaging protocols. The initial positioning of the OCT scans can be performed automatically by processing video images of the retina obtained from a fundus camera. To initially locate the optic nerve head, survey OCT scans which cover a wide field of view on the retina and intercept the optic nerve head can be performed. These survey OCT scans can be used to find the location of the optic nerve head to perform additional registration scans of the optic nerve head which can be analyzed to extract the position of one or more landmarks.

Feature/landmark analysis is performed on the survey/registration scan data. The survey/registration scan data is analyzed using computer image processing to extract features which determine the position of the center of the optic nerve head which will serve as a landmark for subsequent OCT data acquisition. In this example, the center of the optic nerve head, the position of the landmark, might be determined by detecting features such as the positions where the retinal pigment epithelium (RPE) or choroid terminate near the margin of the optic nerve head or optic disc.

Figure 11A:
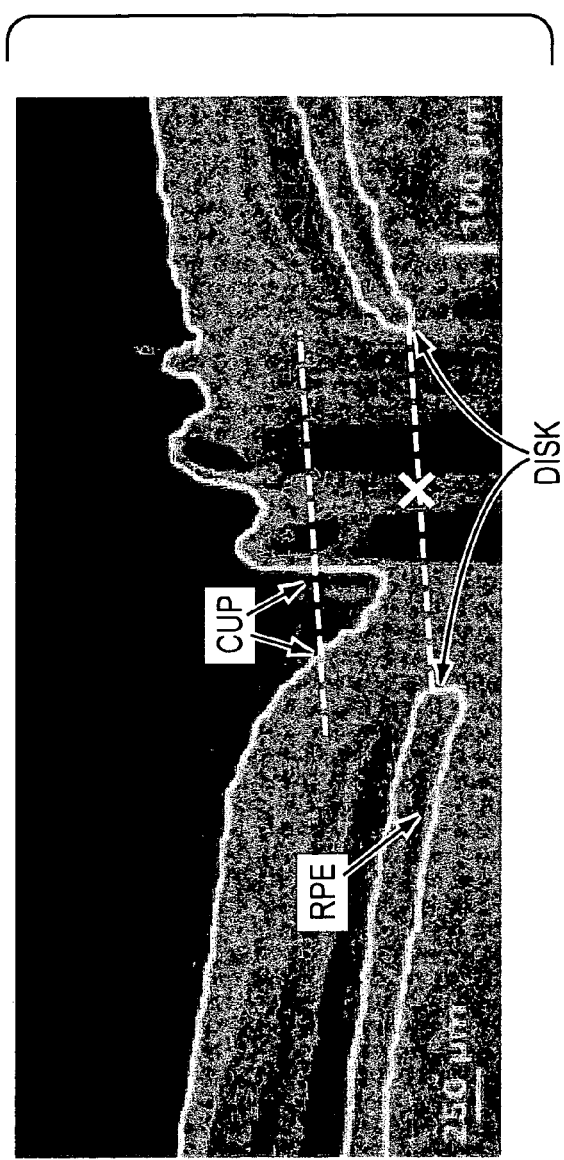
FIGS. 11A-11B are images depicting optic disk and cup identification according to an illustrative embodiment of the invention.
Figure 11B:
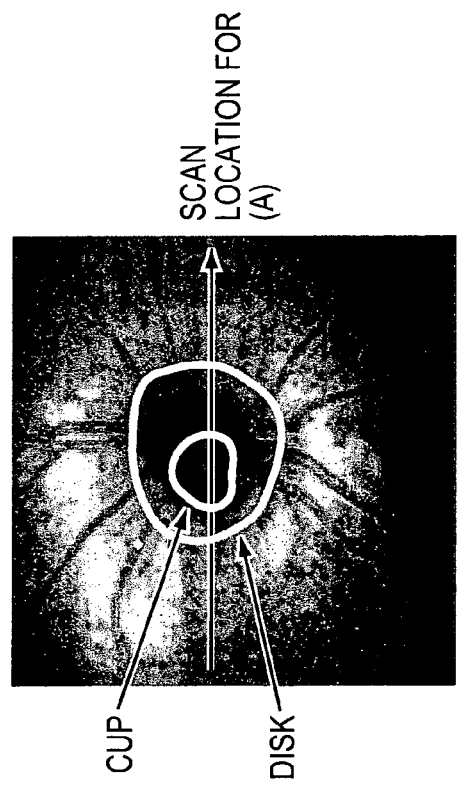

These features are shown in the OCT images of FIGS. 11A-11B. The edge of the optic disc is defined by the termination of the retinal pigment epithelium (RPE), as shown in FIG. 11A. Survey/registration scans should be performed which do not intersect blood vessels that may make recognition of landmarks difficult. In addition to the center of the optic nerve head, other topographic landmarks such as the bottom of the cup (see FIG. 11A) may also be determined by analyzing optic nerve head topography. In OCT imaging, the cup is often defined by drawing a line (see lower dotted line in FIG. 11A) between the two termination points of the RPE, and drawing a second, parallel line offset from the first line (see upper dotted line in FIG. 11A) by a predetermined distance. The intersection of the second line with the vitreoretinal interface defines the cup in each cross sectional image, as shown in FIG. 11A. The optic disk margin (outer ring) and the cup contour (inner ring) are shown on an OCT en face fundus image in 11B, along with the approximate location of the OCT image shown in FIG. 11A (the arrow shown in FIG. 11B).

As discussed above, FIGS. 12A-12D shows an embodiment of feature/landmark analysis in intelligent OCT scanning in ophthalmology. The termination of the retinal pigment epithelium (RPE) and choroid near the optic disk margin is detected by computer image analysis and used as a feature to define the optic disk perimeter. Two or more non-parallel cross-sectional OCT scans are used as survey/registration scans. In each of FIGS. 12A and 12C these two scans are shown.

These survey/registration scans may be used to determine the position of the center of the optic nerve head as the landmark. The procedure is described as follows: first the two termination points of the RPE and choroid at the perimeter of the optic nerve head (i.e., optic disc) are detected in each of the two OCT cross-sectional survey registration images using image analysis, as shown in FIG. 12A. For each survey/registration image, a line segment is drawn between the two features, the termination points of the RPE and choroid, and the midpoint of this line segment is determined. The midpoint of the line segment is marked with an "X" in each image (see points $X_1$ and $X_2$ in FIGS. 12A and 12B, X generally). FIG. 12B shows an en face view of the optic nerve head where the transverse position of the "X" is marked and shown with the two vectors (1, 2) defining the survey/registration scan pattern in FIG. 12B. Next, two lines, shown as dotted lines, are constructed which are perpendicular to the OCT scan lines and intersect the position "X" between the features. The transverse position which is the intersection of these two dotted lines is calculated and is an estimate of the center of the optic disc. The center of the optic disc serves as the landmark at position XD as shown in FIGS. 12C and 12D.

In situations where features and landmarks have a high degree of symmetry, it may be possible to establish the position of the landmark within sufficient accuracy using a single set of OCT survey/registration scans. However, in general, it will be necessary to iterate the procedure of survey/registration scanning and feature/landmark analysis. In this example, once an estimate of the position of the center of the optic disc, the position of the landmark, is obtained, the procedure of survey/registration scanning is repeated and using the estimate of the landmark position to aim the next survey/registration scans so that they intersect the landmark. Then feature/landmark analysis is performed on these new survey/registration scans to obtain a second measurement of the landmark position. If this second measurement of the landmark position agrees with the first estimate to within a given error, the process has determined the landmark position with the desired accuracy. If the second measurement is not within accepted limits, the process can be repeated or the survey/registration scan pattern changed and the process repeated to obtain a convergent measurement of the landmark position to within an acceptable error bound. An exemplary process for this method is discussed above with respect to FIG. 2.

When the landmark position is known, subsequent OCT data acquisition scans can be aimed and registered with respect to this landmark. Embodiments of the invention that use survey/registration scans to register the location of acquired data are possible as well. In addition, the survey/registration scans need not be distinct from the acquired data.

In general, the OCT beam scanning is aimed using the position of the landmark measured from the survey/registration scans and the feature/landmark analysis. Typically, in the case of glaucoma diagnosis, the center of the optic nerve head is used as the landmark. For glaucoma diagnosis, the OCT beam is often scanned in a circular pattern or set of circles to generate circumpapillary OCT data or images of the nerve fiber layer emanating from the optic nerve head. Since the thickness of the nerve fiber layer decreases with distance from the optic nerve head, it is desirable to perform the OCT beam scanning and acquire OCT data or images that are precisely and reproducibly registered with respect to the optic nerve head.

In intelligent scanning, the OCT beam scanning is aimed using the position of the landmark so that the scan pattern is centered on the optic nerve head. In this case, the OCT beam scanning is performed by driving OCT beam angle actuators with waveforms such that the OCT beam scans a circle of chosen diameter on the retina. The process of aiming is implemented by adding offsets to the waveforms so the circular scan pattern is centered on the landmark, the center of the optic nerve head as discussed above.

Although this example describes a circumpapillary OCT data scan, it is understood that other types of OCT data scans can be acquired as well, including but not limited to, multiple circumpapillary scans of identical or differing diameters, linear scans at different angles through the optic nerve head, raster scans, or others.

Iteration of survey/registration scanning and feature landmark analysis is performed to obtain accurately registered OCT data. After the beam scanning has been aimed and OCT data acquisition performed, the accuracy of the OCT data or image registration with respect to the landmark may be measured by iterating the intelligent scanning procedure.

If the data acquisition scans are acquired very rapidly after the initial survey/registration scans are performed, the relative motion, during the OCT data acquisition, of the tissue or sample to the position of the OCT beam is likely to be negligible and within acceptable error bounds. In this case, the OCT data acquisition scans are registered to the landmark to within the desired accuracy. However, different factors during OCT data acquisition such as limited acquisition speed, unstable patient fixation, and rapid eye movements (e.g. involuntary saccades) can all lead to an increase in the relative motion between the tissues or sample and the position of the OCT beam to beyond acceptable error bounds.

To address this possibility, an additional iteration of the survey/registration scans can be performed at the end of data acquisition scans to confirm the position registration of the OCT data to the landmark is within the desired accuracy. This post-acquisition iteration of the registration scans is similar to the initial pre-acquisition registration scans that were performed. For instance, two non-parallel registration scans which generate images though the optic nerve head can be performed. The position of the post-acquisition registration scans may be determined by using the registration information analyzed from the pre-acquisition registration scans.

Feature/landmark analysis is performed on the post-acquisition iteration of the registration scans to determine if the position of the landmark (i.e. optic nerve head) has moved outside of acceptable error bounds. If there is evidence of significant motion between the pre- and post-acquisition registration scans outside of the acceptable error bounds, then the acquired OCT data is not validly registered to the established landmark and will be discarded. The post-acquisition registration scan will then serve as a new survey/registration scan that will direct and aim the OCT beam back onto the landmark in an iterative fashion. The process of survey/registration scans, landmark analysis, and OCT data acquisition scans will then be repeated until the position difference in the landmark location between the pre- and post-acquisition registration scans are within acceptable bounds. The post-acquisition registration scans allow the determination of the validity and integrity of the acquired data so that it is substantially free from motion errors and registered to the landmark to within the desired accuracy. Incorrect registration with respect to the landmark can reduce the diagnostic accuracy or longitudinal tracking capability of OCT.

In some cases the landmark analysis might not yield the desired information about the position of landmarks. For example, in the case of locating the optic nerve head, this could occur if some of the OCT scans happened to overlap blood vessels which emanate from the optic nerve head. In this case, alternate registration scans can be chosen and performed. The position of the optic nerve head can be determined by scanning along any two or more nonparallel axes across the optic nerve head. The position of the optic nerve head can also be determined from OCT scan information that is not in the form of an image. Alternatively, the registration scans can include a grid of measurements at different transverse points which cover the optic nerve head. FIG. 3 shows a set of examples of possible survey/registration scans. Other scan patterns are also possible.

Since current high-speed OCT systems can acquire many images in a fraction of a second, performing registration scans, landmark analysis, image acquisition scans, and repeating the registration scans and landmark analysis for confirmation can be performed very rapidly. In a real-time application such as ophthalmic imaging, intelligent scanning methods need to be performed within a time window when motion of the tissue is not appreciable. The different processes of intelligent scanning are performed before any appreciable motion has occurred that would cause an unacceptable error in the position registration of the different OCT scans to the landmark. Therefore, the recent advances in OCT technology that increased the acquisition speeds by factors of 10× or 100× enable the application of intelligent OCT scanning.

OCT Scanning of the Macula

Another embodiment of intelligent OCT scanning relates to measuring the macula (region of the retina near the fovea). This measurement would typically be used in conjunction with the previously described apparatus embodiments for the intelligent hand-held OCT ophthalmoscope and the intelligent OCT retinal screener, as well as with other OCT ophthalmic devices. Intelligent scanning enables directing or aiming OCT beam scanning and OCT data acquisition in ophthalmic OCT imaging instruments when a view of the retina is either unavailable or insufficient to enable accurate aiming the OCT scanning by the operator. Intelligent scanning enables OCT data or images to be acquired from a desired region of the retina. In addition, by iterating the procedure it is possible to detect changes in eye position and avoid motion error in OCT data.

An outline of a method for measuring the macula follows: first, survey/registration scans covering the available field of view are performed to intercept the macular region. These scans can be a series of horizontal or vertical lines which are offset, although many other patterns are also possible. The survey/registration scans are analyzed by computer or other processor to detect the presence and location of features which can be used to determine the location of the macula or fovea. Since OCT survey/registration scans measure cross sectional structure rather than only an en face view, several possible features can be used to determine the position of the fovea.

Figure 13B:
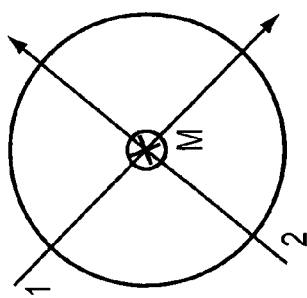
FIGS. 13A-13D are schematic diagrams depicting landmark analysis examples according to an illustrative embodiment of the invention.
Figure 13A:
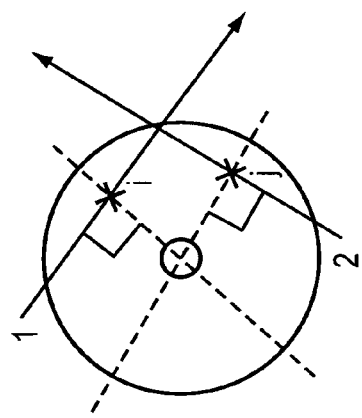

FIGS. 13A-13D shows one embodiment of feature/landmark analysis for intelligent scanning of the macula. In applications such as imaging the macula or optic disk in ophthalmology, the OCT cross-sectional image of the tissue has a cup-like contour. The center or minimum of the contour may be used as a landmark. In this example, two or more non-parallel OCT scans are performed and used as survey/registration scans. The survey/registration scans are analyzed to detect the contour or topography and determine a feature, the "valley" of the contour in each image, as shown in FIG. 13A. In this case, the feature, the minimum of the contour is marked with an "X" (See points $X_i$ and $X_j$ in FIGS. 13A-13B) which is analogous to the "X" shown in FIGS. 12A-12D.

Figure 13D:
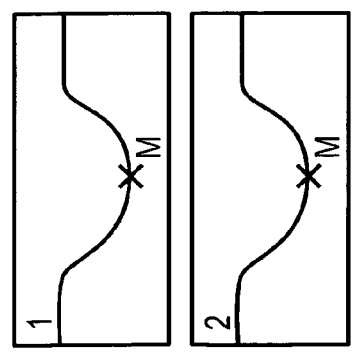
Figure 13C:
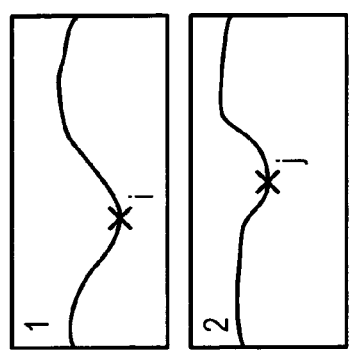

FIG. 13B shows an en face view of the retina in the macula or optic nerve head region where the transverse position of $X_i$ and $X_j$ are marked and shown along with the two vectors defining the survey/registration scan pattern. By constructing two lines that perpendicularly intersect the scan pattern vectors at the locations marked by $X_i$ and $X_j$, shown as dotted lines in FIG. 13B, it is possible to estimate the position of the center of the contour in two dimensions, which serves as a landmark. The position of the landmark, the center of the macula or the optic nerve head is estimated using the intersection of the dotted lines. The position of this landmark is marked by a circle in the figures. FIGS. 13C and 13D show that the procedure of survey/registration scanning and feature/landmark analysis may be iterated to measure the position of the landmark XM to within an acceptable error bound.

While this example shows the use of the contour of the macula, other sample features, not only those limited to the eye, can be used as features or landmarks in survey/registration scans. For example the position of the center of the macula, the landmark position, can be determined by measuring the thickness of the retina (which is minimum at the center of the normal macula) or individual layers such as the outer nuclear layer (which is maximum at the center of the normal macula).

In patients with severe macular edema, layers in the retina may be elevated near the fovea, obscuring the foveal pit. This necessitates the use of other landmarks, such as the optic disc, to perform registration. In the majority of patients, the optic disc is located at a given distance from the macular or fovea. The position of the macula or fovea can be determined using the optic disc (i.e., optic nerve head) as a landmark. Retinal blood vessels which are visible in Doppler OCT images or an OCT en face image or an en face reconstruction of three-dimensional OCT data can also be used as landmarks. Finally, in cases such as macular thickness mapping where the imaging/scanning pattern is designed to intersect the fovea, the OCT acquisition images themselves may also be used for survey/registration scans and feature/landmark analysis.

After the location of the fovea has been determined, the OCT beam scanning can be directed or aimed so that OCT data/image scans are registered with respect to the fovea. In this example, it is desirable to perform the OCT data scans covering the foveal or macular region. These scans may include, but are not limited to: three-dimensional imaging, macular thickness mapping, photoreceptor mapping, retinal pigment epithelium analysis, intraretinal layer mapping, Doppler imaging, and high transverse pixel density imaging. For measuring macular thickness, the imaging pattern may include a radial spoke pattern designed to maximize sampling density in the fovea. In other applications such as photoreceptor mapping, a pattern of dense sampling in the fovea designed to improve visualization of small abnormalities or disruptions may be used. In both these examples, aiming of the scan pattern on the macula or fovea is typically performed.

For applications involving comparative studies over time, precise and reproducible registration of OCT data/images is required.

An iteration of the survey/registration scanning and feature/landmark analysis may be performed after data acquisition to assess possible registration errors in the OCT data and confirm that the image or data is still centered on the macula/fovea to within an acceptable error bound. Changes in the measured landmark position are also used indicate motion which produces registration error in the OCT data.

Description of Alternate Survey/Registration Scan Patterns

The previous examples of feature/landmark determination have used features/landmarks in the sample which have a high degree of symmetry. In addition to features previously described, it is also possible to use other features such as blood vessels to define landmarks that may be used for intelligent OCT scanning. The use of blood vessel features has applications in macula, optic nerve head, and circumpapillary OCT imaging and data acquisition. The method of feature/landmark analysis described here would also be applicable for analyzing other types of features such as thin linear structures.

Figure 14C:
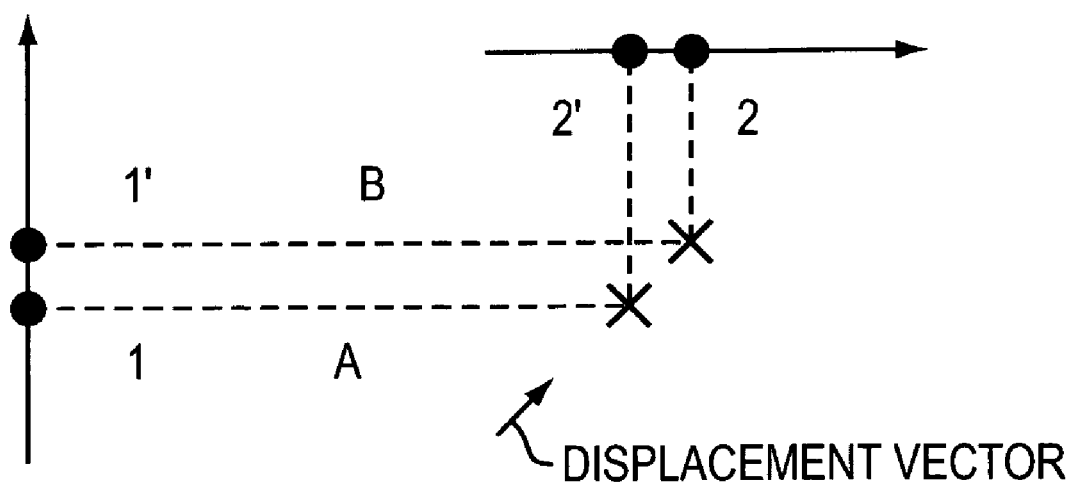

When scanning blood vessels as candidate landmarks and other like sample features, it is desirable to perform survey/registration scans on a region of the sample having two nearly perpendicular transverse features that are substantially constant over a given region. These two features may be used to define a landmark, or a unique transverse position in the tissue/material. FIGS. 14A-14C shows schematically how registration scans and feature/landmark analysis can be performed for this case.

FIGS. 14A-14C do not show the cross sectional OCT registration images, but instead show the positions of the scans in an en face view of the sample. Linear registration scans are performed in directions that are nearly perpendicular to the features. The initial aiming of these registration scans can be performed by the operator or by using survey scans which cover a larger region and can be analyzed to detect the presence of the desired features.

The location of the landmark can be determined by finding the feature in the OCT registration scans (shown by a black dot in FIGS. 14A-14C), calculating the lines which are perpendicular to these features (shown as dashed lines in FIGS. 14A-14C), and determining the point of intersection of the two perpendicular lines (shown as an X in FIGS. 14A-14C). Because the linear features were selected to be nearly perpendicular and are scanned nearly perpendicularly, this landmark has a unique and well-defined position.

The procedure of performing survey/registration scans and feature/landmark analysis may be repeated and used to determine the relative motion between the tissue/material and the OCT apparatus. In the example shown, one feature is horizontal and intersected by a vertical registration scan (scan 1 in FIG. 14A), while the other feature is vertical and intersected by a horizontal registration scan (scan 2 in FIG. 14A). In this example as shown in FIG. 14B, the horizontal registration scan through the vertical feature may be used to detect motion in the horizontal direction, while the vertical registration scan through the horizontal feature may be used to detect motion in the vertical direction. This method works best when the features are nearly straight and nearly perpendicular and when the registration scans are performed nearly perpendicular to the features.

If a second set of survey/registration scans is performed at a later time, the landmark position may be determined as described previously. As shown in the FIG. 14B, because the relative transverse position of the OCT apparatus and the tissue/material may have changed during the time between the two scans, the landmark position determined from the second set of survey/registration scans (scans 1' and 2') may differ from the first shown in FIG. 14A. As shown in FIG. 14C, the difference between the two determined landmark positions (from scans 1, 2 to scans 1', 2') gives the relative transverse motion between the tissue/material and the OCT apparatus between the two sets of survey/registration scans. This can be used to assess the registration error in the OCT data by generating a displacement vector as well as for motion tracking. Changes in the axial as well as the transverse position of the material/tissue can also be assessed using this method.

In addition to using isolated features such as blood vessels, multiple linear features visible in cross sectional OCT registration images can be used to assess motion of the sample by cross correlating registration images. For example, if the registration scans are nearly perpendicular and intersect sets of features that are nearly linear and perpendicular to the scans, then motion of the material/tissue in the plane of the scan might be detected by cross-correlating subsequent registration scans. If there is no motion, then the cross-correlation of the registration scans is sharply peaked about zero. However, if there is motion, then the cross-correlation peak is shifted by the amount of the motion. Motion which occurs perpendicular to the plane of the registration scan results in reduced cross-correlation function, however, if there are sets of features in the image which are substantially perpendicular to the scan plane, then correlation is still maintained and this method can be used to measure the motion.

Figure 15B:
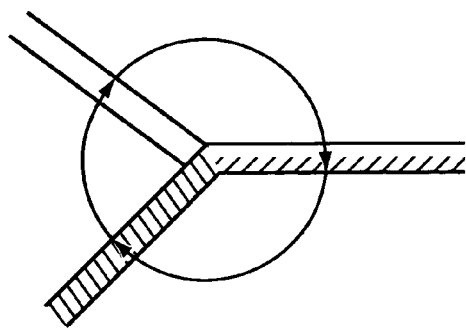
FIGS. 15A-15C are schematic diagrams depicting alternate survey/registration scans according to an illustrative embodiment of the invention.
Figure 15C:
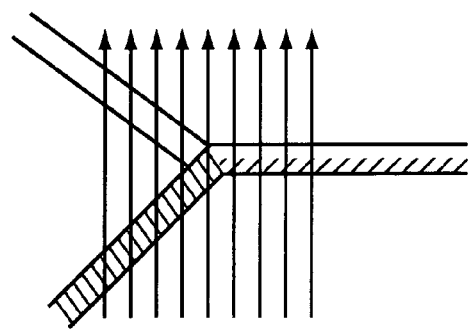
Figure 15A:
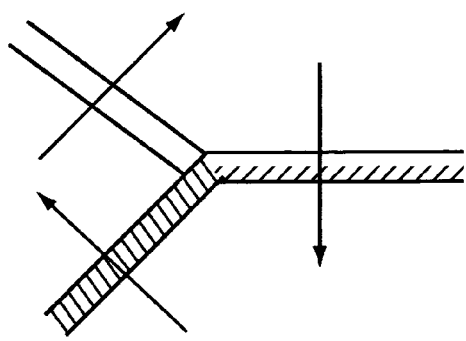

Numerous other survey/registration scan patterns are possible. One example uses survey/registration scans that intersect more than two non-parallel linear features. This is shown in FIG. 15A wherein a set of three scans are centered on a blood vessel bifurcation. The landmark defined by the three branches in this case is the point of bifurcation. Because the three vessel branches nearly perpendicularly intersect the three linear survey/registration scans, it is possible to calculate the landmark position by generating a perpendicular line intersecting each linear scan at the point of intersection between the linear scan and the blood vessel. These three lines are then substantially parallel to the blood vessel branches, and therefore would intersect at or near the point of bifurcation which can serve as a landmark.

Another possible survey/registration scan pattern is a circular scan centered on a region with sufficiently distinctive features along the scan. For example, the circular scan pattern may be centered on the position of a blood vessel bifurcation, as shown in FIG. 15B. Because each branch is substantially perpendicular to the registration scan pattern at the point of intersection, the method discussed above may be used to determine the blood vessel bifurcation. In addition, the circular registration scan has the advantage that it can be performed more rapidly than two linear scans or other discontinuous scan patterns.

In another embodiment, a dense raster scan may be used as the survey/registration scans. The survey/registration scans should be performed in a region of the material/tissue having suitable features/landmarks such as at the position of a vessel bifurcation or another region with distinctive features, as shown in FIG. 15C. Each set of survey/registration scans produce a three-dimensional data set. This survey/registration data set may be directly analyzed to determine the positions of landmarks, as discussed previously. In another embodiment, the three-dimensional data sets from successive sets of survey/registration scans may be correlated using correlation algorithms. The result of the correlation analysis is a measurement of the three-dimensional displacement between the two data sets. The data sets may be processed or filtered before correlation to remove speckle or other noise if needed. In another embodiment, the OCT data from each set of survey/registration scans may be reduced to a two-dimensional image by summation of the data along the axial direction. Any correlation algorithm may be used to determine the transverse displacement between two scans. Correlation of two images or data sets may also be used to determine their relative orientation in addition to their relative displacement.

Data Acquisition with Periodic Aiming to Track Motion

Intelligent OCT scanning can be used to acquire a series of OCT data acquisition scans, where each series in the OCT data set is registered to the tissue/material. In addition, intelligent scanning can also be used to track the motion of tissue/material by periodically re-aiming the OCT data acquisition scanning. These functions can be implemented by repeating or iterating the procedure of survey/registration scans, feature/landmark analysis, directing/aiming the OCT beam scanning, and OCT data acquisition scans. This is shown in the process flow 36 depicted in FIG. 16. As shown, the steps discussed above with respect to FIG. 2 are performed. After data acquisition 36*a*, the data is stored 36*b* and survey/registration scans and feature/landmark analysis is repeated to re-direct or re-aim the data acquisition 36*c*. If there is sample motion, which occurs slowly compared to the time required to iterate the procedure and the motion is not too large compared to the desired registration accuracy, then the storing of the OCT and repeating landmark analysis to control scanning beam positioning can be used to track any sample motion.

The scanning pattern for data acquisition may be changed by changing the waveforms which drive the OCT beam scanning mechanism (see FIG. 4). In one embodiment, a predetermined sequence of waveforms specifying a sequence of data acquisition scanning patterns may be used on successive repetitions of the loop. For example, the sequence of scanning patterns may acquire data from different regions of the tissue/material. On each repetition, intelligent scanning is employed to aim the data acquisition scan based on features/landmarks in the material/tissue.

Figure 16:
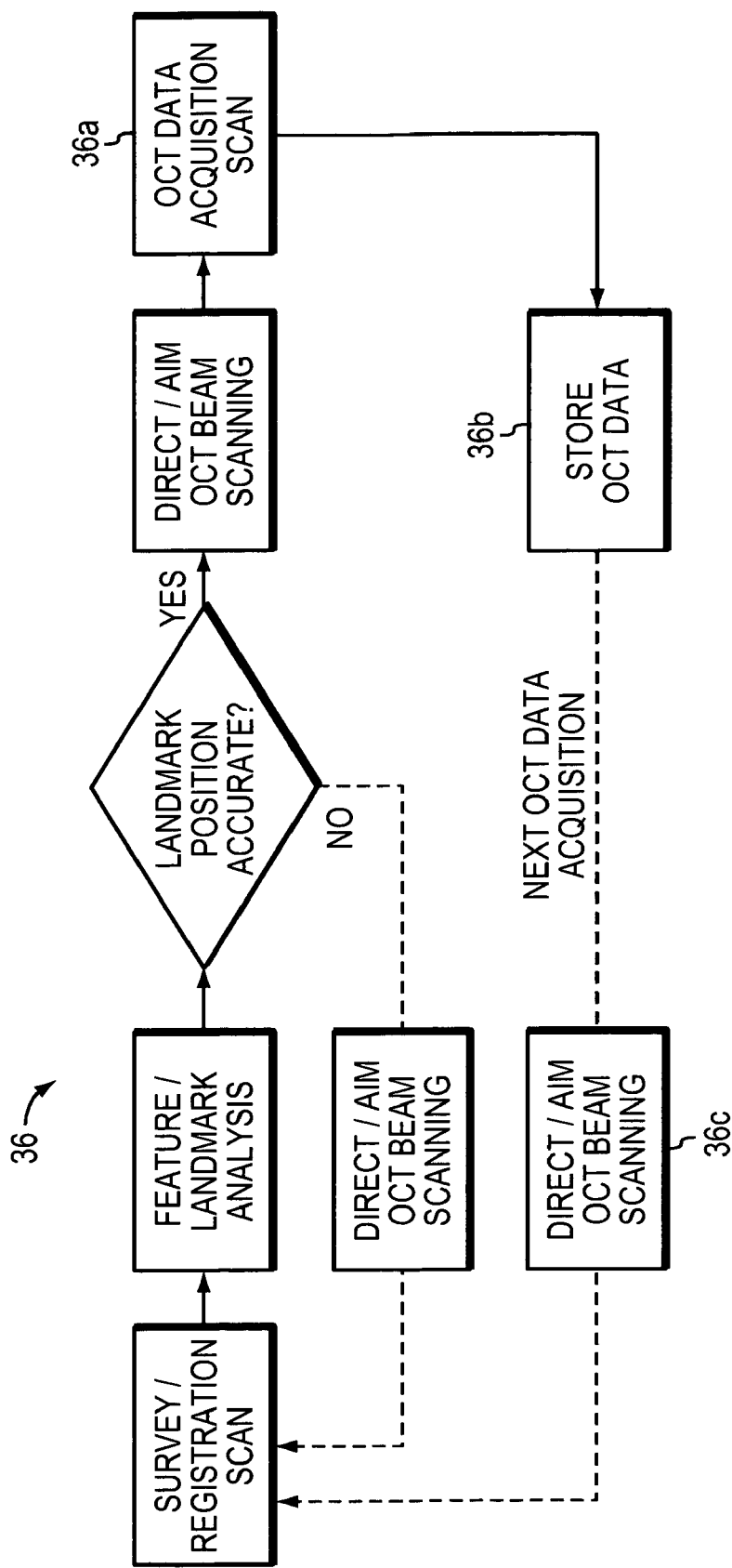
FIG. 16 is a flow diagram depicting a method for intelligent OCT scanning with repeated data acquisition according to an illustrative embodiment of the invention.

In other embodiments, the same data acquisition scan may be performed on successive repetitions of the loop in FIG. 16, in which case the OCT beam scanning tracks material/tissue motion. This feature allows successive OCT scans to be obtained which are precisely registered to the sample.

Intelligent Scanning to Acquire Subsections of a Large OCT Data Set

The aforementioned procedures work in situations when the motion of the material/specimen is slow compared to the time between subsequent iterations which periodically re-aim the OCT beam scanning and data acquisition; and when the motion is small compared to the desired registration accuracy. However in many cases, motion of the sample can be larger and occur more rapidly. In these cases, it is possible to use a variation of the aforementioned intelligent scanning procedure to obtain large data sets which are registered to the sample.

One example of this type of application is three dimensional OCT data acquisition. With recent advances in OCT acquisition speed, it has become possible to acquire three-dimensional OCT data such as raster scans or a dense array of points which measure a volume of sample. However, in many imaging applications, imaging speeds are still not sufficient to acquire large amounts of data over a large region of the tissue without motion error. For example, to assess fine structure in intraretinal layers, detailed (high pixel density) OCT images of the retina are required. Unfortunately, for some applications, the imaging time is still limited by subject motion and imaging cannot be performed over the entire region of interest without motion errors. Intelligent OCT scanning enables the separate acquisition of a series of OCT data scans which are all registered to the same landmark and therefore registered with respect to each other. This enables the acquisition of large OCT data sets without motion errors. Thus, multiple scans at different points in time can be related to combine a plurality of smaller data sets into a larger data set.

Figure 17:
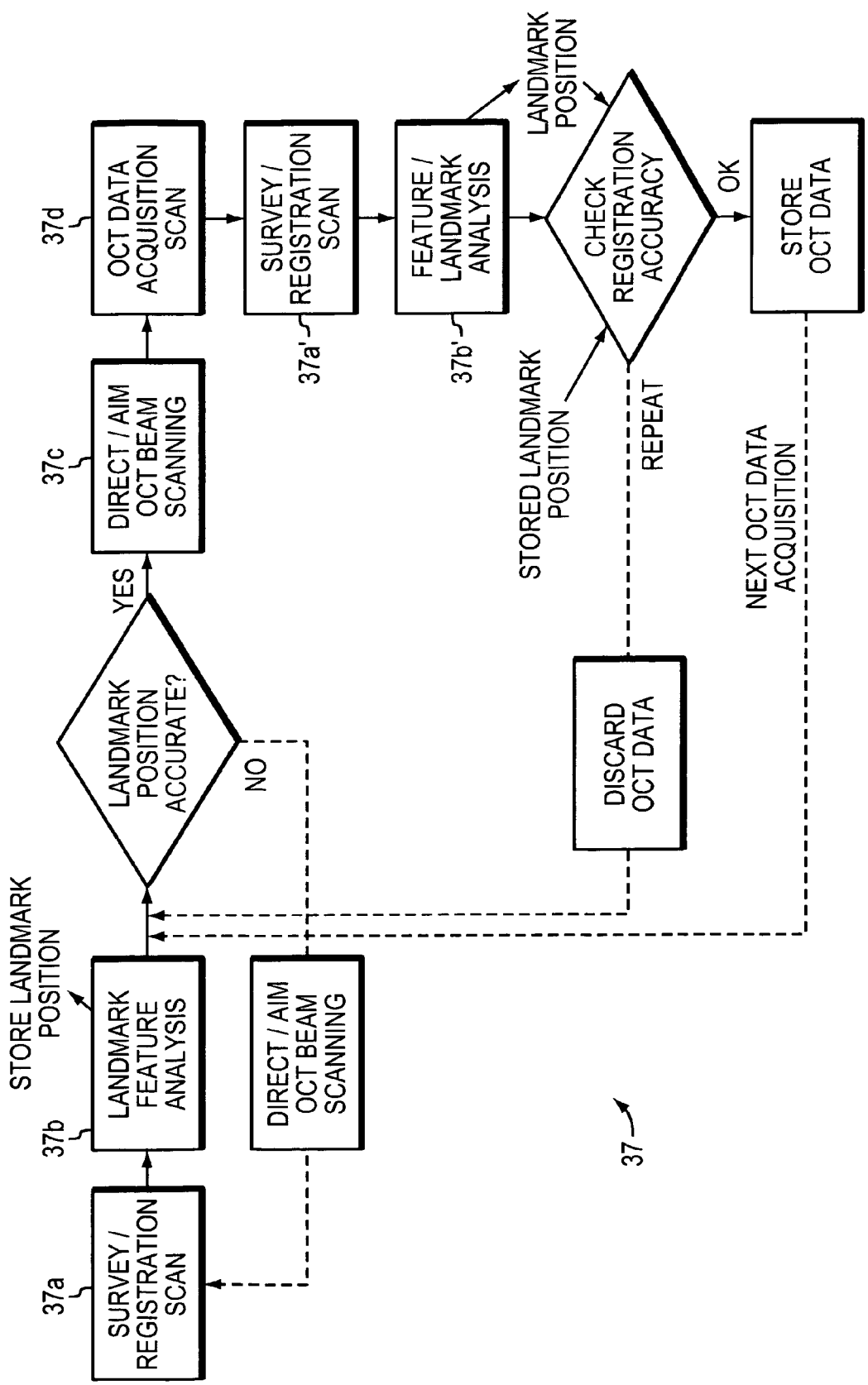
FIG. 17 is a flow diagram depicting a method for intelligent OCT scanning with a registration accuracy check and repeated data acquisition according to an illustrative embodiment of the invention.
Figure 18C:
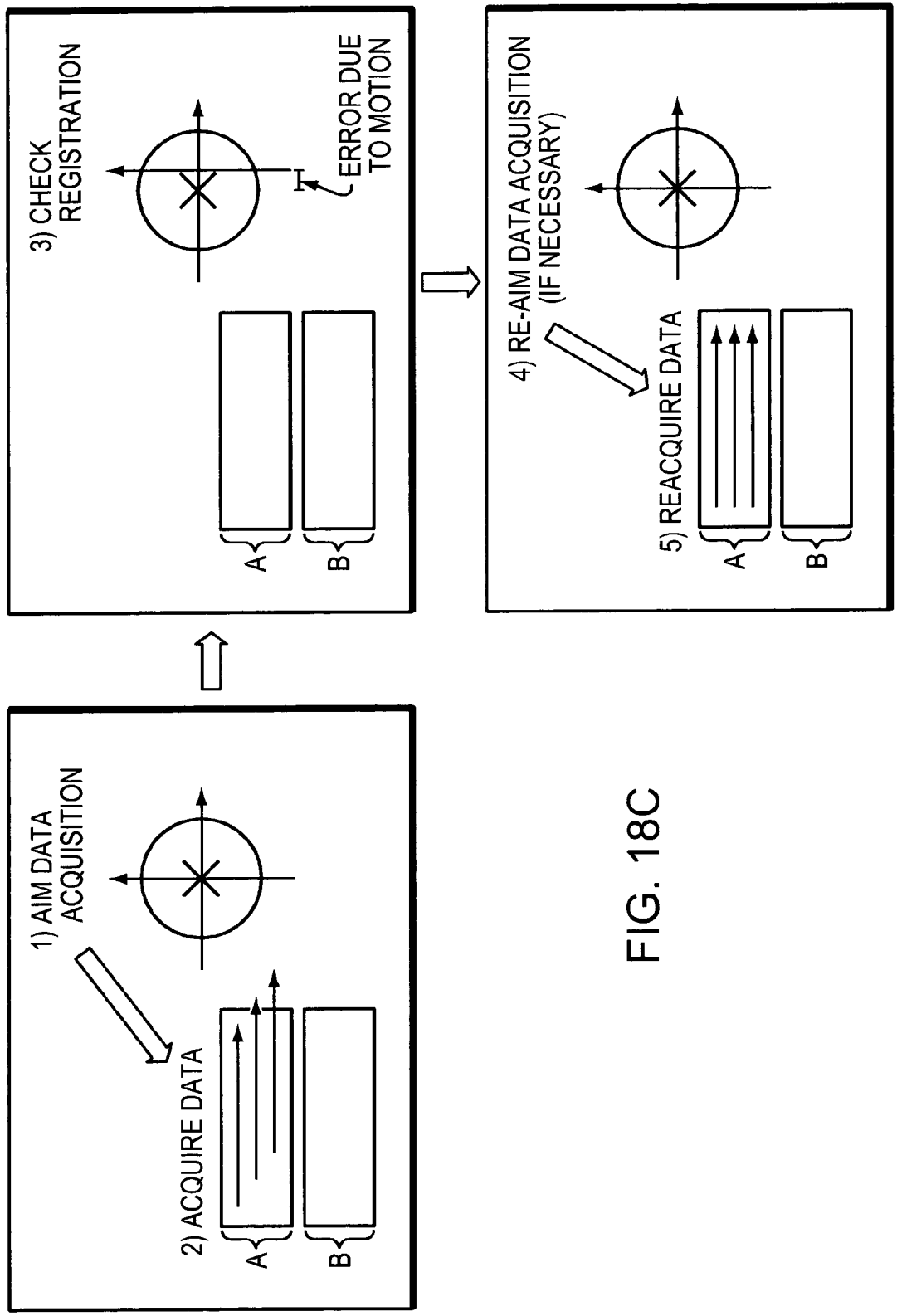

FIG. 17 shows a process flow 37 for intelligent scanning that enables the acquisition of large data sets without motion errors. Examples of survey/registration scans and OCT data scans suitable for compiling large data sets are shown in FIGS. 18A-18C. As portions of the process flow depicted in FIG. 17 have already been introduced with respect to FIG. 5, only the additional steps are discussed in more detail.

Returning to FIG. 17, first, survey/registration scans 37a are performed over a region of the sample with suitable features or landmarks. Then, feature/landmark analysis is performed 37b on the scans to determine the position of the desired landmark. This is used to direct/aim OCT beam scanning 37c and OCT data acquisition of a block of OCT data 37d in a desired subsection of the total region. These steps correspond to the depiction shown in FIG. 18A. After the OCT data is acquired, the procedure is repeated or iterated (See process stages 37a' and 37b'). New survey/registration scans and feature/landmark analysis are performed (not shown) and the new position of the landmark determined and compared to the previous position by checking the registration accuracy. Furthermore, this part of the procedure is similar to the one shown in FIG. 16.

If the registration error from possible relative motion between the sample and the OCT system is small and within acceptable error limits, then the current OCT data is stored. The OCT beam scanning is then directed/aimed to the next subsection of the total region and the data acquisition is performed. These steps are also depicted in FIG. 18B. The branch of the flow chart is labeled "next OCT data acquisition" in FIG. 17.

Conversely, if the registration error from motion is larger than acceptable error limits, then the current data is discarded. The process is iterated and the landmark position is used to re-aim the OCT beam scanning and perform survey/registration scans. Feature/landmark analysis is used to determine the new position of the landmark. When registration of the landmark position is re-established, the OCT beam scanning will be re-aimed and repeated on the first subsection of the total region. These steps are shown in FIG. 18C. Using this method of intelligent scanning, data from each of the subsections of total region is tested for motion error and re-acquired if necessary.

These procedures are repeated until all of the subsections have been acquired with an acceptably small amount of motion error. The OCT data acquisition scans from each of the multiple subsections of the total region are then registered to the landmark and therefore registered with respect to each other. Finally although the described approach emphasizes transverse registration, a similar method can be used to register the data in the axial direction. Registration in the axial direction can be performed either by actuating the delay in the OCT interferometer which establishes where the data occurs within the measurement range. Alternately, axial motion error is usually corrected by processing and translating the OCT data in the axial direction to maintain registration in that direction.

Intelligent Scanning to Acquire and Superimpose Large Field of View Data

Figure 19B:
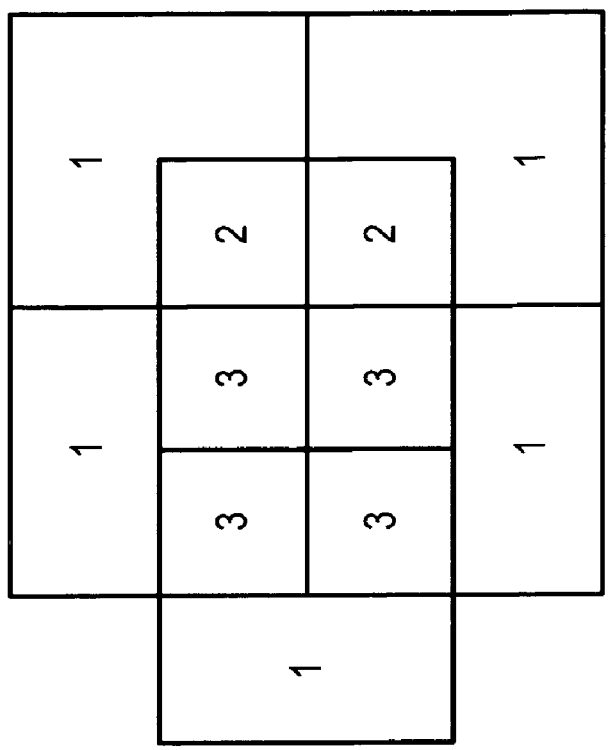
FIGS. 19A-19B are schematic diagrams depicting an example of separately scanning seven overlapping regions according to an illustrative embodiment of the invention.
Figure 19A:
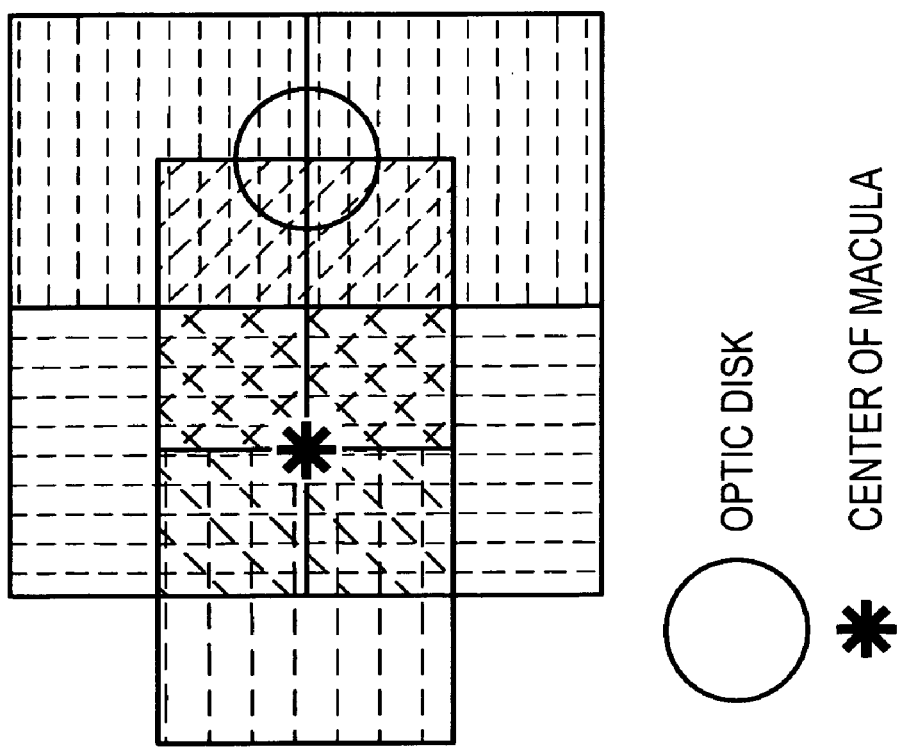

Intelligent scanning methods allow the data acquired from multiple sections of the total scan field to be superimposed or combined to create a large data set that represents the OCT data from the entire scan field of the tissue. This results because all the different sections of the total scan field are precisely registered to a known landmark in the tissue. This aspect of the invention is applicable to OCT data acquisition/imaging of the optic disk as well as other OCT applications outside of ophthalmology. In optic disk imaging applications, it is possible to divide a field of view into multiple overlapping regions as shown in FIG. 19A. Intelligent scanning can be used to aim data acquisition scans from the multiple overlapping regions of the fundus in a manner similar to stereoscopic 7-standard field fundus photography used to assess diabetic retinopathy.

Survey/registration scans are performed before acquisition of each of the seven different regions shown in FIG. 19A. The landmark(s) used for registration may include the foveal pit, the optic disk contour, blood vessel features, the optic disk cup, or other features. After data acquisition, the individual data sections are registered to the landmark and can then be combined to reconstruct the complete large scan field. Because the individual scan sections are overlapping, registration may be also be achieved or confirmed by correlation of the overlapping portions of the different scan regions. In addition, the overlapping sections can also be designed so that clinically important regions, such as the macula, will have more than one overlap and higher transverse density scanning can be achieved. As shown in FIG. 19B, five of the seven regions are scanned once, one region is scanned three time and one region is scanned twice.

Figure 20:
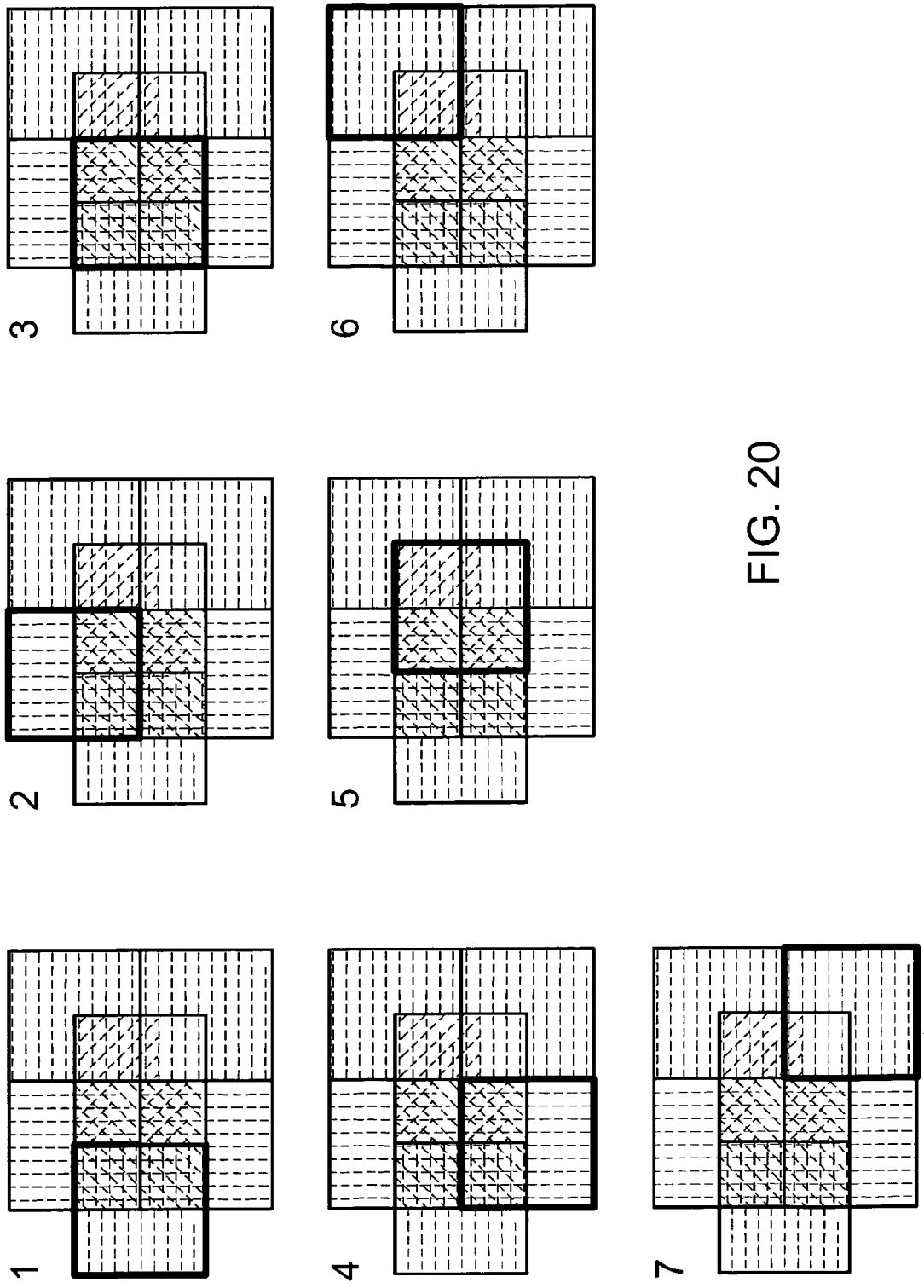
FIG. 20 is a schematic diagram depicting a sequence of scans according to an illustrative embodiment of the invention.

FIG. 20 shows that each separate region, shown by the darkened rectangular border, is scanned separately, while positioning is corrected and/or verified between scans with successive survey/registration scans and feature/landmark analysis. This enables the successive data/images acquired in the separately scanned regions to be registered with respect to the retina and with respect to each other. This method can then be used to construct a larger, integrated data/image set and to ensure that data/images over a large area can be systematically acquired.

Figure 21:
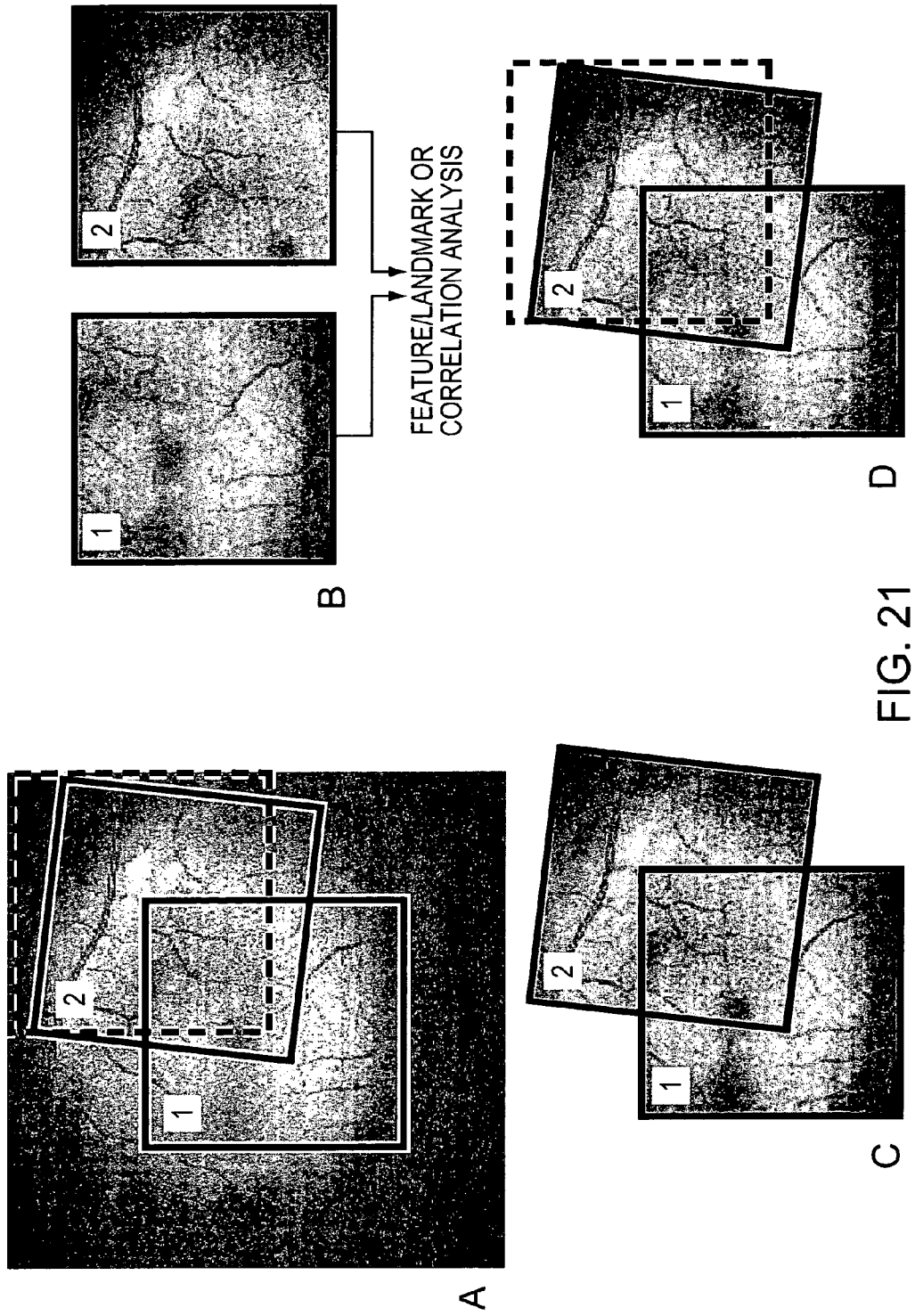
FIG. 21 depicts a set of images that demonstrate correlating two data sets according to an illustrative embodiment of the invention.

Four sets of images A-D are shown in FIG. 21. These images show the en face image data that can be used, in the absence of landmark registration, to correlate the acquired data from different overlapping regions in the tissue or sample. Image A shows two overlapping scan regions 1 and 2. In this retinal imaging example, two regions of the retina near the fovea were acquired so that the data acquired from region 1 overlaps the data acquired from region 2, similar to ETDRS stereoscopic 7-standard field fundus photography. After the data is acquired from the different regions, the acquired data in region 2 can be registered to region 1 by comparing the en face fundus image information (e.g. blood vessel presence and distribution) between the two regions to detect and correct any relative translational or rotational motion and registration error (see images C-D). The dotted lines indicate the correct position that the results when OCT scan 2 will be translated to properly register the two scans. By acquiring data from different sections of the total scan field with sufficient overlap with each other, en face image information can ensure that different data subsets can be registered to each other as shown in image D wherein an image correlation has been performed. In this manner, an OCT data set of the total large scan field can be constructed even in the absence of precise position registration to a landmark.

While some of the figures discussed above pertain to ophthalmology, the method and apparatus of intelligent scanning may be applied as described to any OCT system to acquire registered data over a large scan field. In addition, different survey/registration and data acquisition scan patterns may also be used to achieve the same result.

Reduction of Scan Data to Two dimensions for Landmark Analysis

Figure 22:
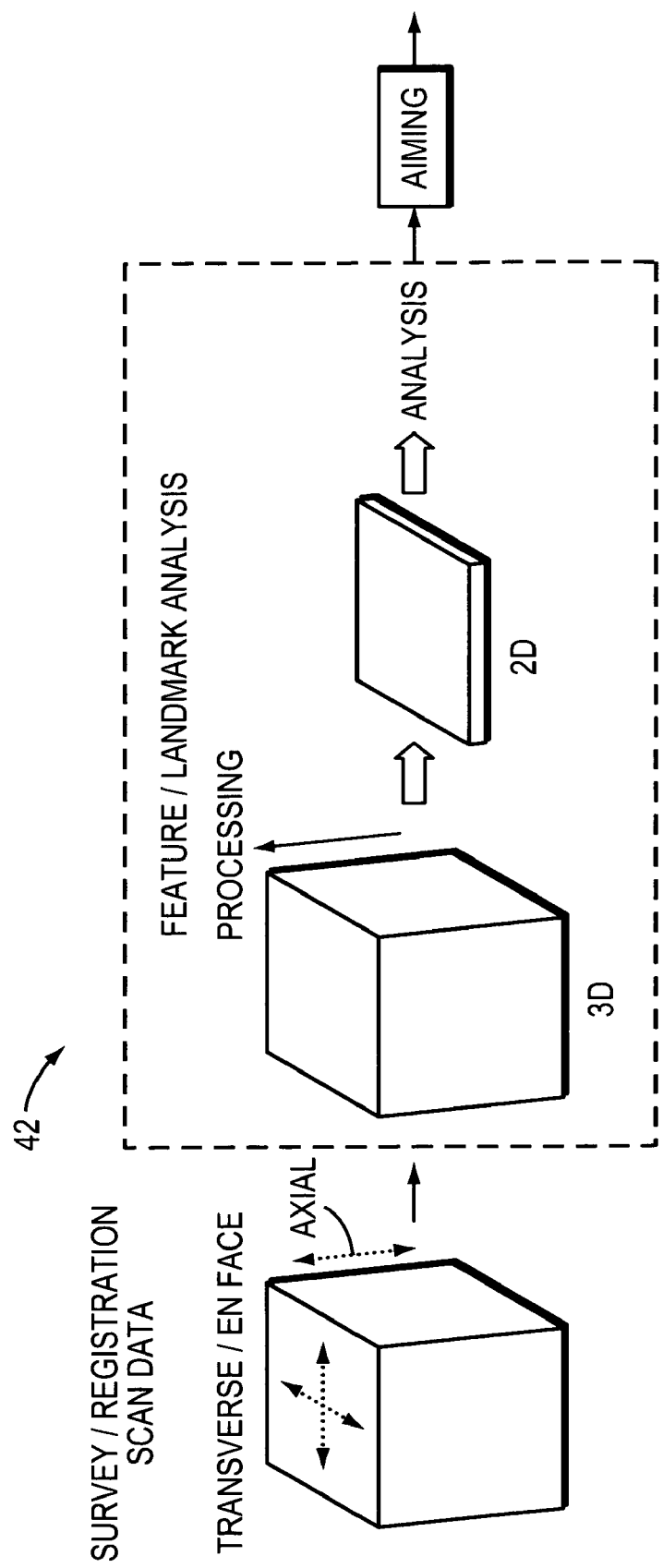
FIG. 22 is a flow diagram depicting reduction of survey/registration data to two dimensions according to an illustrative embodiment of the invention.

In the previous embodiment, en face image information was used to correlate different scan regions in the absence of landmark registration. In this embodiment, the landmark analysis stage uses a reduction of survey/registration data to two dimensions to examine en face features/information or transverse variations in sample or tissue structure. The general procedure 42 for reducing a three dimensional data set to two dimensions is shown in FIG. 22. As shown, the landmark analysis step reduces the dimensionality of the data (3D) by processing along the axial direction to yield 2D data. This processing may include, among other things, segmentation and mapping to generate intraretinal layer maps or total macular thickness maps, summation of data to generate a fundus image, or image analysis to map some other parameter.

Further analysis of the dimensionally reduced map/image/data set helps to locate landmarks or features that can be used for aiming and registration of subsequent scans. This can also entail mapping some quantitative measures obtained from cross-sectional information and using the quantitative map to determine the location of subsequent scan locations. Landmark analysis may be used to precisely locate the same position across multiple OCT imaging sessions by comparing features such as the presence and distribution of blood vessels.

With the reduction of survey/registration data to two dimensions, it is possible to rapidly perform a set of survey/registration scans on the optic disk to generate an OCT fundus image by axial summation of the OCT data or three-dimensional data. The resulting two-dimensional data set can then be analyzed to identify landmarks such as blood vessels for position registration. Thus, this aspect of the invention can use the fundus image, blood vessels, or other landmarks contained in the reduced OCT data set to determine and register the location of subsequent OCT data acquisition or survey scans. In addition to this embodiment of two-dimensional feature/landmark analysis, it is also possible to identify the positions of blood vessels by using standard OCT data/images or functional Doppler OCT data/images for landmark analysis.

To contrast this aspect of the invention with tracking-assisted OCT, since the OCT images provide a cross-sectional view, the landmark analysis can use features inside the retina which are not visible in a simple external, en face view such as would be provided with a fundus camera or a scanning laser ophthalmoscope. In addition, this invention processes OCT data to determine the positions of features or landmarks, and does not require a separate beam for tracking. Thus, an enhanced level of data registration is possible.

Figure 23:
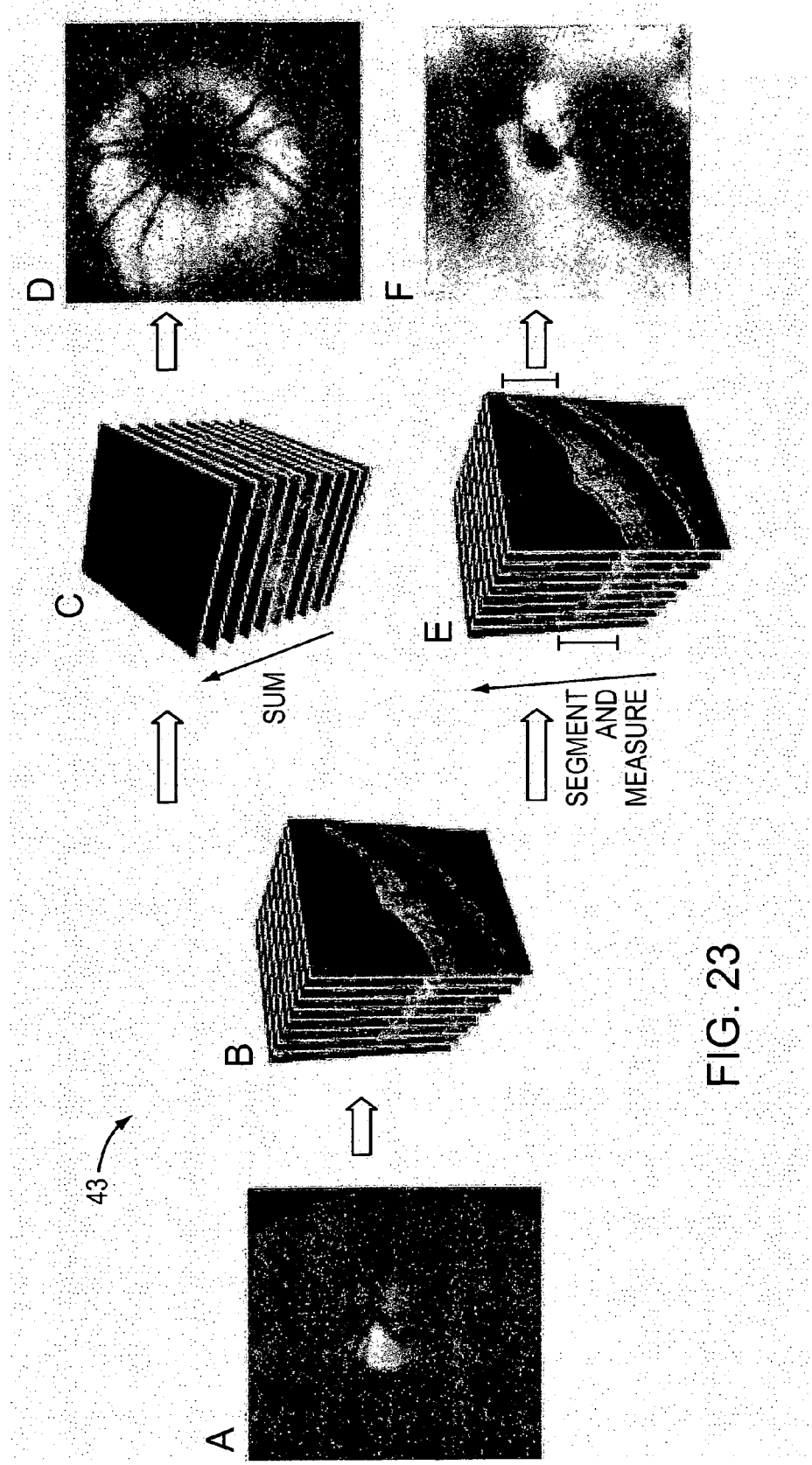
FIG. 23 is a flow diagram depicting reduction of data to two dimensions for feature/landmark analysis according to an illustrative embodiment of the invention.

An example of this dimensionality reducing method for optic disk imaging 43 is shown in FIG. 23. FIG. 23 includes process stages labeled A-F. First the survey/registration scans are performed (stage A) and data is acquired (stage B). One possible survey scan protocol is a raster scan. In one embodiment, the data is summed along the axial direction (stage C) to generate an en face image (stage D). This fundus image clearly shows bifurcations in blood vessels and other features which may be used as landmarks. Secondly, it is possible to generate maps of intraretinal layer thickness, macular thickness, or other parameters from survey scans and analyze the results to determine the locations for subsequent data acquisition. The generation of an optic disk topographic map from segmented cross-sectional data is shown in stage E and F of the method 42. Cross-sectional data is segmented along the axial direction, and the topography is measured (stage E) and mapped (stage F). This example shows an ophthalmic application, but similar procedures can be applied to other applications.

Figure 24B:
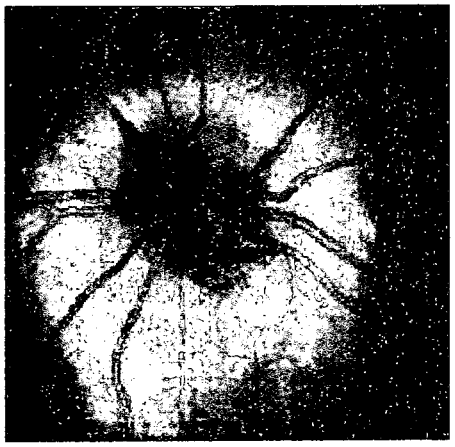
FIGS. 24A-24D are a set of en face images and maps for feature/landmark analysis according to an illustrative embodiment of the invention.
Figure 24D:
Figure 24A:
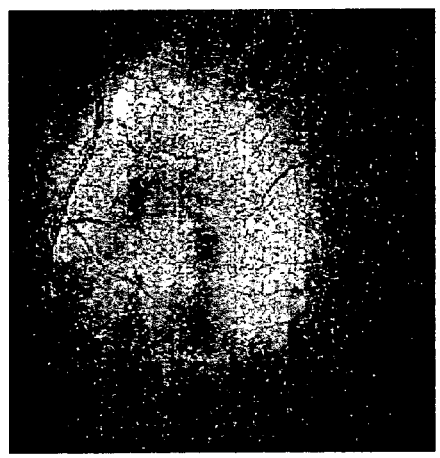

FIGS. 24-24D shows en face fundus images as well as total retinal thickness maps in both the macula and the optic disk. Applications include macular imaging (FIG. 24A), and optic disk/circumpapillary imaging (FIG. 24B), where it is possible to generate a fundus reconstruction by summation that can be used to locate landmarks such as blood vessel patterns. The landmark analysis stage may entail comparison of features in survey/registration scan data such as a fundus reconstruction to features in previously acquired survey/registration scan data from a previous data acquisition session.

Figure 24C:
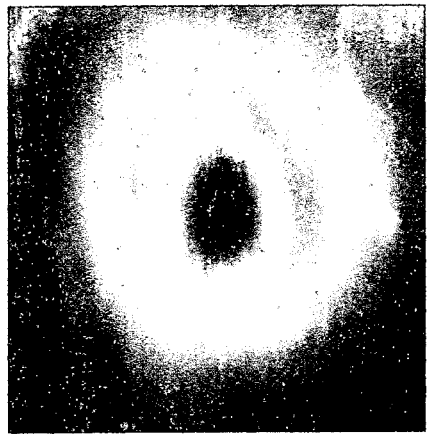

In addition, it is possible to use automatically generated quantitative maps to locate pathologies/abnormalities, or regions of interest for subsequent data acquisition. For example, macular thickness maps may be used to locate the fovea in subjects with a normal foveal contour, or alternatively can be used to locate areas of edema for further investigation with high performance scanning (FIG. 24C). Optic disk topography may also be used to define quantitative landmarks (FIG. 24D). Many other metrics may be used in intelligent scanning. The use of OCT images and data provides information from internal microstructure of sample that is not available in standard en face images. Therefore, more landmarks or quantititative measures may be used.

OCT Data Processing to Obtain Registered OCT Images or Data

In another embodiment of the invention registered OCT images or data may be generated by: performing registration/survey scans and OCT data scans, performing post-acquisition analysis of the registration/survey scans to identify features/landmarks, and directing/aiming the processing of OCT data using the location of features/landmarks to obtain registered OCT images or data. This embodiment may be desirable in some applications because it does not require rapid feature/landmark analysis and the real-time directing/aiming of the OCT beam scanning using the feature/landmark information. In this embodiment, survey/registration scans and OCT data are acquired first, resulting in a survey/registration data set and an OCT data acquisition set. Subsequent steps are performed in post processing. The two data sets may not necessarily be distinct from each other, and a subset of the OCT acquisition data set can function as the survey/registration data set, or vice versa.

If the survey/registration data set and the OCT acquisition data set are acquired rapidly in sequence, then there should be very little relative motion of the sample during the data acquisition time and the two data sets will be registered with respect to each other within a desired accuracy. Feature/landmark analysis is performed on the survey/registration data set to direct or aim data processing on the OCT data acquisition set to obtain OCT data that is registered to the landmark.

Figure 25:
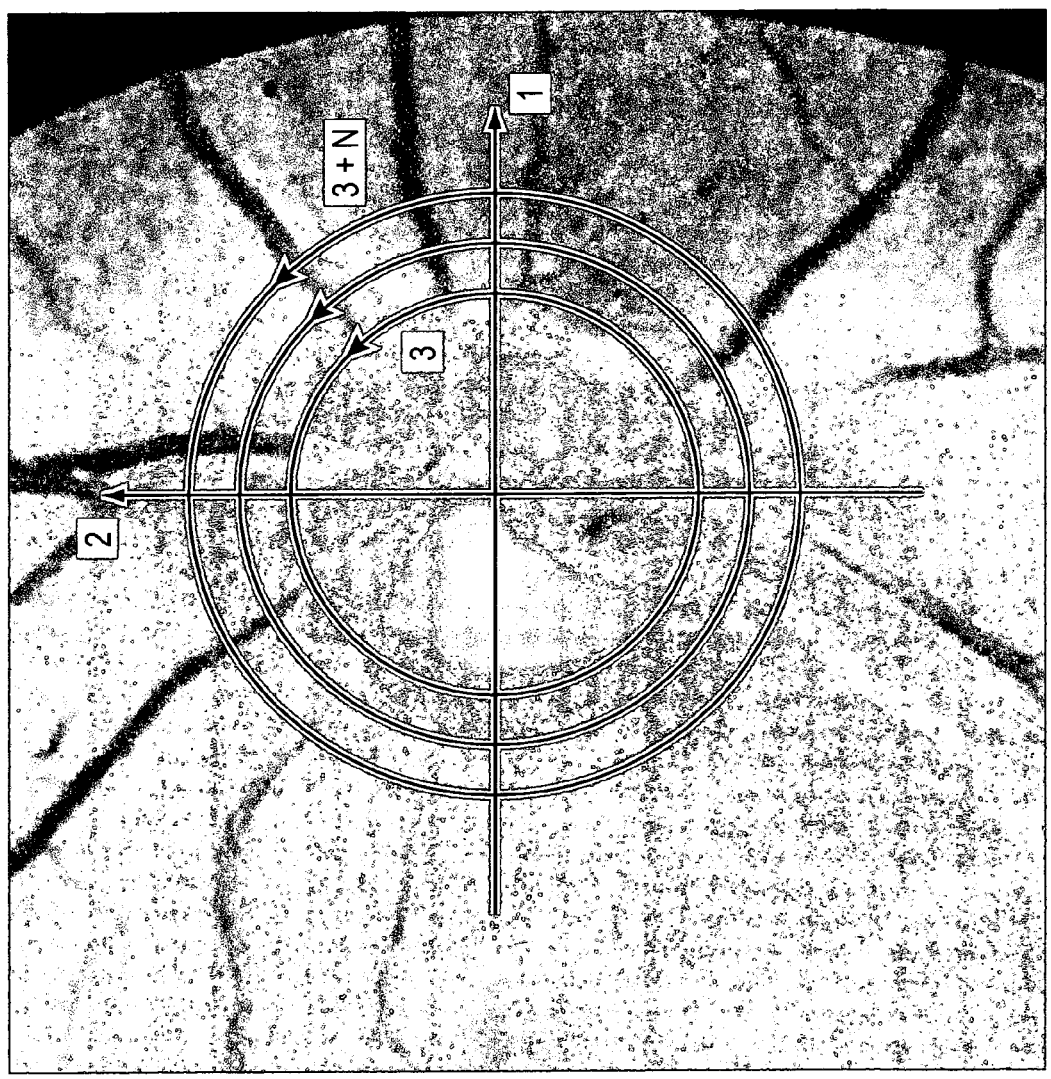
FIG. 25 is an image depicting an example of a survey/registration scan and a data acquisition scan according to an illustrative embodiment of the invention.

FIG. 25 shows an example of imaging and measuring the nerve fiber layer around the optic nerve head in glaucoma diagnosis. In this example, the objective is to obtain a cylindrical (circumpapillary) OCT image or OCT data along a circle which is precisely registered with respect to the center of the optic nerve head. This information is used to quantitatively measure the nerve fiber layer thickness around the optic nerve head and aids in glaucoma diagnosis.

The procedure for generating a precisely registered OCT image or data is as follows: survey/registration scans, shown in FIG. 25 as 1 and 2, are performed, followed by a series of circular OCT data acquisition scans of different diameters, 3 to N. After the survey/landmark and OCT data scans are acquired, feature/landmark analysis is performed on the survey/registration scans using the methods previously described, to determine the location of the center of the optic nerve head which serves as a landmark.

Figure 26A:
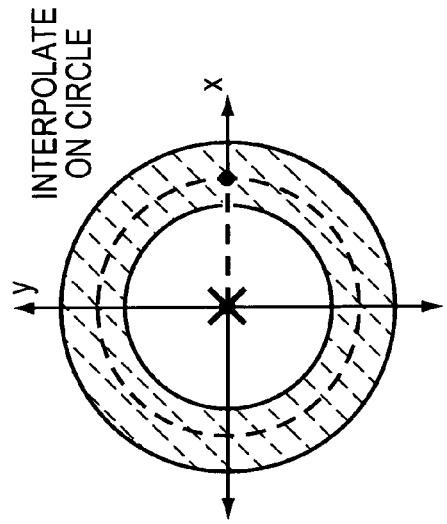
FIGS. 26A-26D are a set of graphs depicting an example of interpolation based on survey/registration data according to an illustrative embodiment of the invention.

The circular OCT data scans can be processed to align the scans in the axial direction using known methods, and a three dimensional OCT data set is obtained. This OCT data set contains three-dimensional information in an annular shaped volume region around the optic nerve head. If the OCT beam scanning was aimed precisely on the center of the optic nerve head, as shown in FIG. 26A, when the data was acquired, the landmark position will then coincide with the center of the annular three-dimensional OCT data set.

Figure 26B:
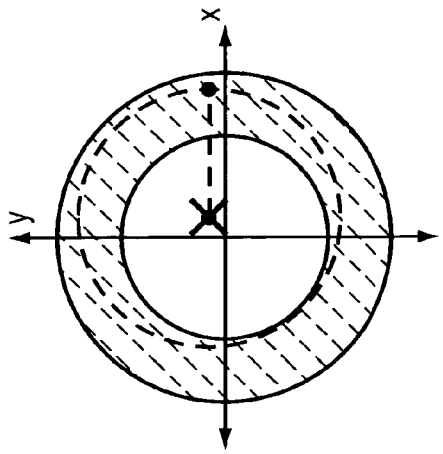
Figure 26C:
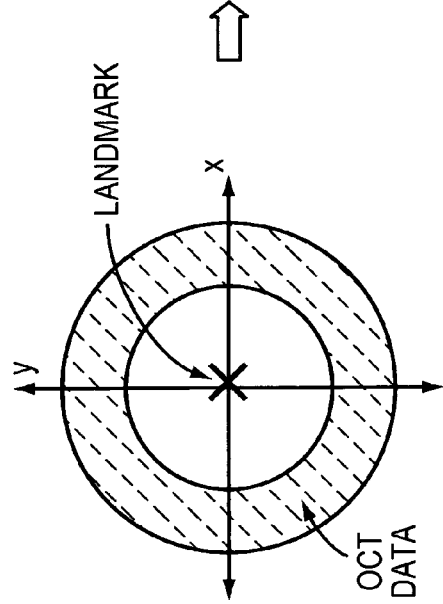
Figure 26D:
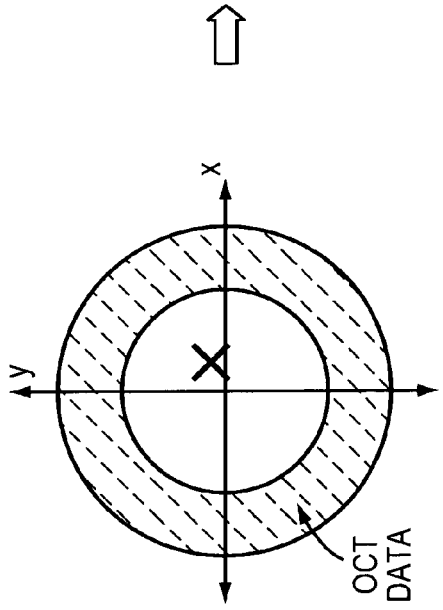

However, in general, the OCT beam scanning will not have been aimed precisely with respect to the center of the optic disc and the landmark position determined from the survey/registration scans will not coincide with the center of the annular three dimensional OCT data set, as shown in FIG. 26C. The region of the annulus of OCT data is shown shaded in FIG. 26. The position of the landmark is used to direct/aim the processing of the three dimensional OCT data set. The three dimensional OCT data is interpolated and processed to generate a cylindrical OCT image or data set, which is precisely registered with respect to the landmark. This is shown schematically as the dashed line in FIG. 26B and FIG. 26D. In FIGS. 26A-B, the annular volume is centered on the optic nerve head. In FIGS. 26C-D, the annular volume region is displaced from the optic nerve head. The interpolation and processing of three dimensional OCT data to extract and generate "virtual" two dimensional OCT images or data can be performed using known algorithms. The resulting cylindrical OCT image or data is precisely registered with respect to the center of the optic nerve head and gives the same information as a circular, circumpapillary OCT scan which is precisely registered with respect to the center of the optic nerve head.

This example was presented describing OCT images, but it is recognized that the method can be applied to other types of OCT data. In the above example, the circular OCT images can be processed to segment and measure the thickness of the nerve fiber layer and to generate a two dimensional map of the nerve fiber layer thickness in the aforementioned annular region around the optic nerve head. This may be performed using well known algorithms used for OCT image and data analysis. The landmark information obtained from the survey/registration scans can be used to determine a circle centered on the optic nerve head and the values of the nerve fiber layer thickness at points on this circle can be determined. This would yield a measurement of the nerve fiber layer thickness along the circle. Finally, it is recognized that although this embodiment was described using an application in ophthalmology, the method applies to many other OCT imaging applications.

In another embodiment of this invention, it is possible to perform additional registration scans for landmark analysis that can direct and improve the future analysis of OCT data. In FIGS. 18A-18C, it was shown that an OCT dataset over a large field of view can be acquired with intelligent scanning by acquiring smaller sections of the total scan field. Since the individual sections are all registered to a specific landmark in the tissue, it is possible to superpose the acquired data from the separate sections to generate a complete dataset that covers the entire scan field. Even though this method permits the registration of the different data sections to a specific landmark in the transverse direction, relative motions in the axial or longitudinal direction can still exist within the different sections of the total scan field. This is especially true if acquisition scans had to be repeated to achieve precise transverse registration to the landmark.

Figure 27:
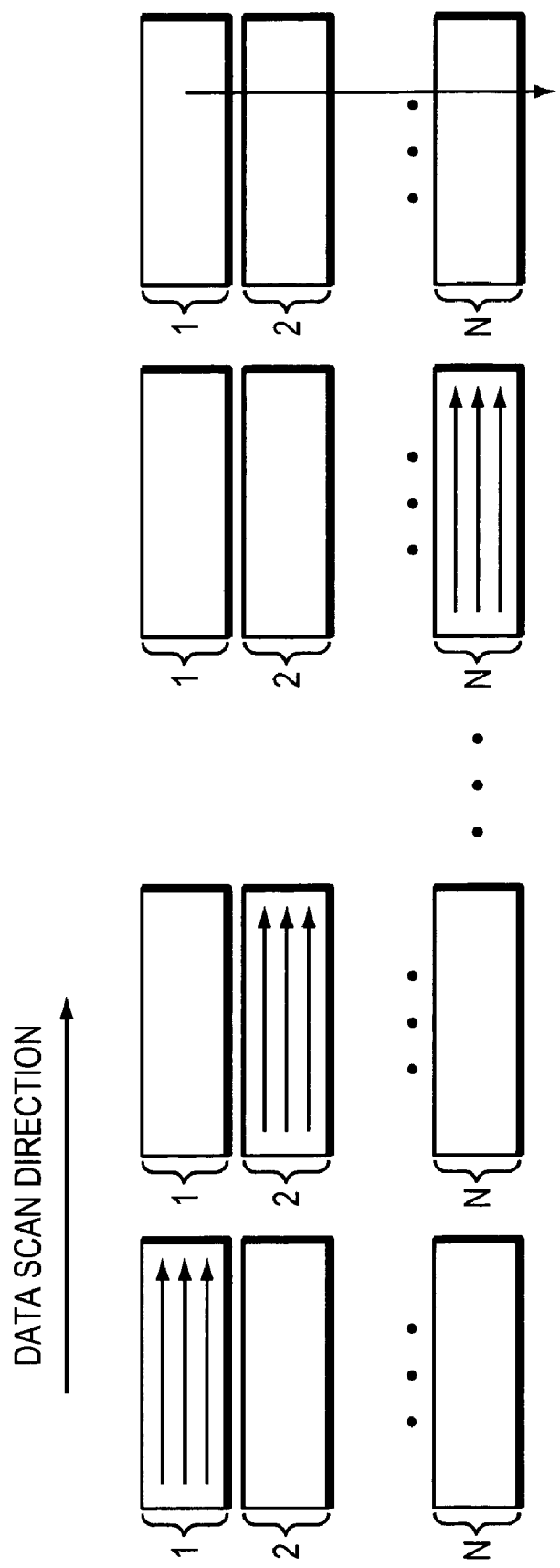
FIG. 27 is a schematic diagram depicting an example of a survey/registration scan for axial correction of data sets from multiple regions according to an illustrative embodiment of the invention.

In another embodiment depicted in FIG. 27, the acquisition of an additional "axial registration scan" perpendicular to the direction of the data acquisition scans will allow the registration of different sections in the total scan field in both the transverse direction (to the landmark of acquisition) and the axial direction (to the landmark of the "axial registration scan"). The landmark analysis performed on the "axial registration scan" can simply be to identify the vitreo-retinal interface or the position of the retinal pigment epithelium layer. If the "axial registration scan" is acquired so that it is also registered to the identified landmark, every acquisition image in the different data sections will have an axial scan (A-scan) that exactly corresponds to an A-scan in the "axial registration scan."

The example demonstrated in FIG. 27 shows that the "axial registration scan" is performed in the direction that is perpendicular to the acquisition direction of the different data regions and intersects them, typically bisecting them. In this example, the particular A-scan at the center of each OCT acquisition image will have a corresponding A-scan in "axial registration scan," that exactly represents the magnitude and time delay of backscattered or backreflected light from that position. The axial position of each separate data section can then all be correlated to the information contained in the single "axial registration scan." In this manner, OCT data from different data sections can be registered, in the axial direction, to each other by registering the axial position of the OCT images to the identified landmark in the "axial registration scan."

OCT Data Processing

Figure 28:
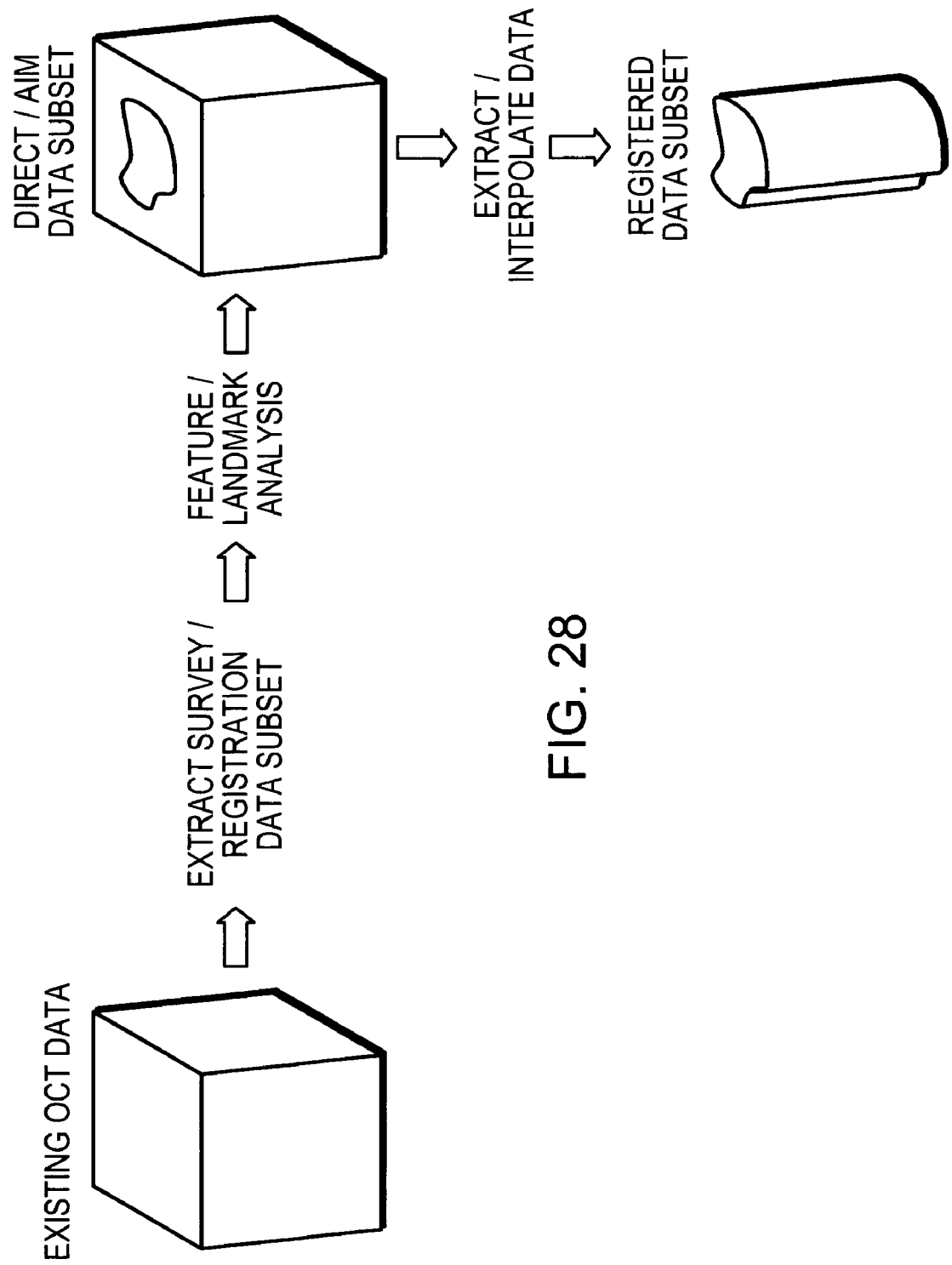
FIG. 28 is a flow diagram depicting intelligent scanning used in data processing according to an illustrative embodiment of the invention.

Intelligent scanning is not limited to directing/aiming OCT data acquisition, but can be used to direct/aim OCT processing. In this embodiment, registered OCT images or data may be generated starting from a large OCT data set by: extracting registration/survey scan information from the data set, analyzing the registration/survey scan data to identify features/landmarks, directing/aiming the processing of large OCT data using the location of features/landmarks, and generating a subset of the large OCT data set which is precisely registered to the feature/landmark positions. A schematic of this method is shown in FIG. 28. This embodiment can be used to simplify the analysis of large OCT data sets, including three dimensional OCT data sets which represent measurements performed over volumes of the sample. Although these large data sets provide detailed volumetric information, they can be difficult to analyze because of their size and complexity.

Figure 29:
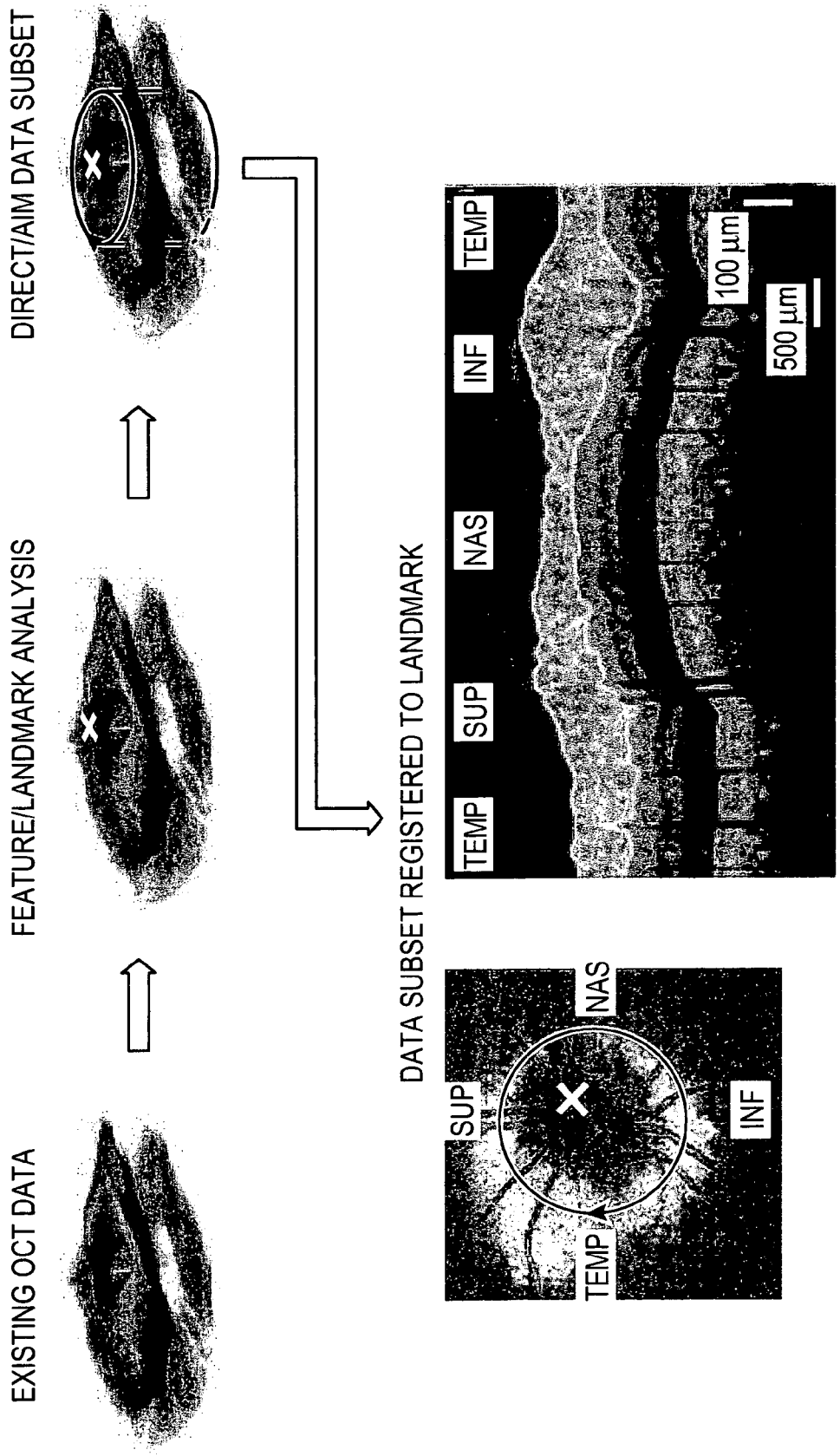
FIG. 29 is a flow diagram depicting an example of intelligent scanning for use in data processing according to an illustrative embodiment of the invention.

FIG. 29 shows an example of imaging and measuring the nerve fiber layer around the optic nerve head in glaucoma diagnosis. In this example, the objective is to obtain a cylindrical (circumpapillary) OCT image or OCT data along a circle which is precisely registered with respect to the center of the optic nerve head. Survey/registration scans are extracted from the large data set and analyzed to determine the location of a landmark, the center of the optic nerve head. In many applications, it may be necessary to evaluate the accuracy of the landmark position and to repeat the survey/registration scan extraction and feature/landmark analysis to achieve the desired accuracy.

This process is similar to that described in FIG. 2, except that the OCT data is obtained by extracting subsets of a larger OCT data set rather than by acquiring OCT data using an apparatus. The position of the landmark, the center of the optic nerve head is shown by an X in FIG. 29. Using the position of the landmark, a cylindrical (circumpapillary) OCT image is obtained from the larger OCT data set. This cylindrical OCT image is precisely registered with respect to the landmark. Using this method, it is possible to precisely and repeatedly obtain OCT images or data from larger OCT data sets which are precisely registered to features or landmarks in the data set. This can simplify the analysis of large data sets in addition to reducing data storage requirements.

Directing/Aiming OCT Beam Scanning

In many OCT applications, it is desirable to direct or aim the OCT beam scanning so that a region of interest of the sample is within the field of view or measurement range of the OCT data acquisition. Intelligent scanning may be used to direct or aim the OCT beam scanning so that OCT images or data are obtained from a desired region of interest. In this embodiment of intelligent scanning this function is performed by: performing survey/registration scans, analyzing the registration/survey scan data to identify features/landmarks, directing/aiming the OCT beam scanning using feature/landmark information such that desired features/landmarks are within the OCT data acquisition field of view or measurement range, and performing OCT data acquisition. The method is different from the previously described method for precise registration of OCT images or data in that the functions of directing or aiming the OCT beam scanning can be performed with less precise control.

This process can be performed to align the OCT instrument or performed iteratively to compensate for motion. Also, this process may be performed repeatedly to maintain the region of interest within the field of view or measurement range on subsequent OCT data acquisitions. This results in a type of motion tracking. The method described here is applicable to track transverse motion as well as axial motion, thereby keeping the three-dimensional region of interest within the three-dimensional scan field or field of view.

Figure 30B:
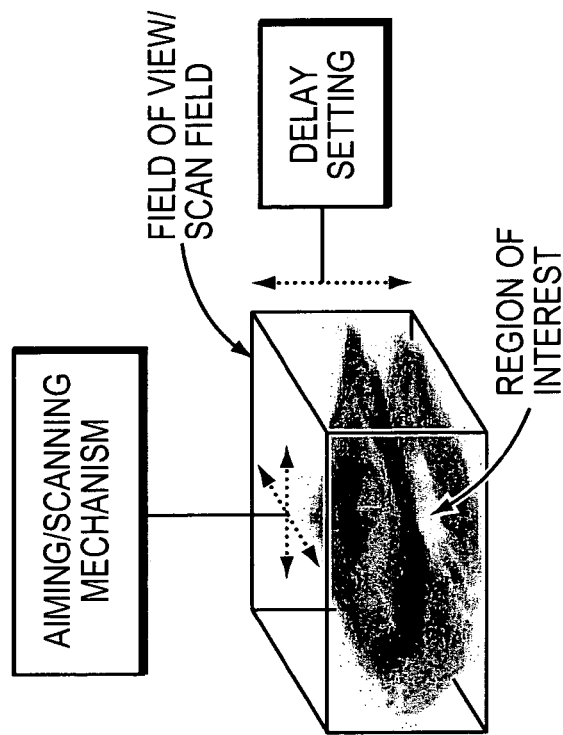
FIGS. 30A-30B are schematic diagrams depicting an example of field of view tracking according to an illustrative embodiment of the invention.
Figure 30A:
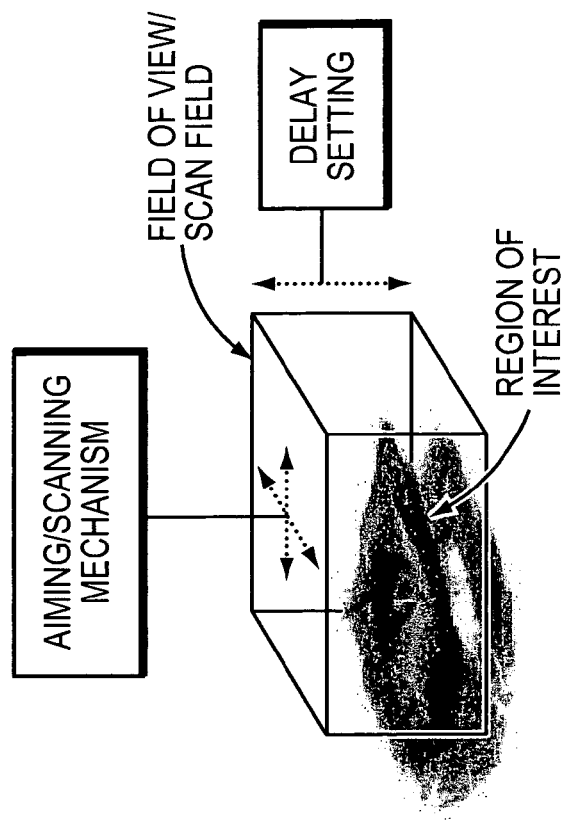

FIGS. 30A-30B shows an example of this embodiment for ophthalmic imaging where it is desired to maintain the macula or fovea of the retina within the field of view or measurement range of the OCT data acquisition. Survey/registration scans are performed and features/landmarks are determined by analyzing these scans. These features or landmarks are used to determine how to translate or align the-scan field or field of view so that the region of interest is within the field of view or measurement range.

Initially, the field of view or measurement range might be misaligned with the region of interest (in this case, the macula of the eye), as shown in FIG. 30A. Survey/registration OCT scans can be analyzed to determine the position of features in the axial direction. The delay setting can be changed to translate the measurement range to span the region of interest in the axial direction as shown in FIG. 30B. Survey/registration scans can be analyzed to locate the region of interest in the transverse direction. As a result, the OCT beam scanning can be directed or aimed in the transverse direction so the field of view in the transverse direction spans the region of interest. Survey/registration scans can be analyzed to determine the presence and location of possible vignetting or mis-alignment and the OCT beam scanning re-directed or re-aimed to reduce this effect. Although this example is presented for ophthalmology, it is recognized that this applies to a wide range of applications.

As noted previously, the OCT beam scanning can be directed or aimed using several approaches which include but are not limited to: actuating the position of the OCT beam scanning apparatus, actuation the position of the instrument, actuating the position of the sample, actuation the position of the patient's head, directing the patient to gaze in a particular direction using a fixation target or display. Finally, the focus of the OCT beam may also be evaluated by analyzing survey/registration OCT scans to determine signal level, sharpness of edge features, or other features. Focus may be adjusted by several methods including, but not limited to: actuating the position of lenses, actuation the position of optical fibers or light sources. Some examples of apparatus which perform these functions are presented in FIGS. 6A to 10D.

Transverse beam positioning may be adjusted by landmark analysis using features such as blood vessels, blood vessel bifurcations or any other landmarks having a fixed position on the retina. In addition, in contrast to scanning laser ophthalmoscopy and fundus photography, OCT provides high resolution cross-sectional images, making it possible to use axial image/scan information in conjunction with blood vessel landmarks or other transverse features.

Intelligent Scanning for Directing/Aiming Enhanced Performance Scanning

Intelligent scanning can also be used for directing/aiming OCT scanning or controlling the operating mode of the OCT instrument so that regions of interest in a sample are scanned with "enhanced performance." Some examples of enhanced performance OCT scanning include, but are not limited to: high transverse pixel density imaging where axial scans are acquired with small transverse spacing between scans; three dimensional imaging, where a dense transverse scan pattern is used to generate three dimensional OCT information; Doppler imaging, where repeated axial scans are used to measure Doppler flow or to detect the presence or density of blood vessels; birefringence sensitive imaging, where axial scans using different polarizations of light are used to measure birefringence properties of sample structures; or functional imaging, where small changes in optical properties of tissue due to functional changes are detected.

However, many of these modes trade performance for imaging speed. Therefore it is often not possible to acquire data from a large region or field of view with enhanced performance. Intelligent scanning can be used in these "enhanced performance" OCT applications to order to direct or aim the OCT beam scanning as well as to control the mode of operation of the OCT imaging instrument to switch between standard OCT imaging mode and "enhanced performance" mode, to optimize performance and acquisition time.

Figure 31:
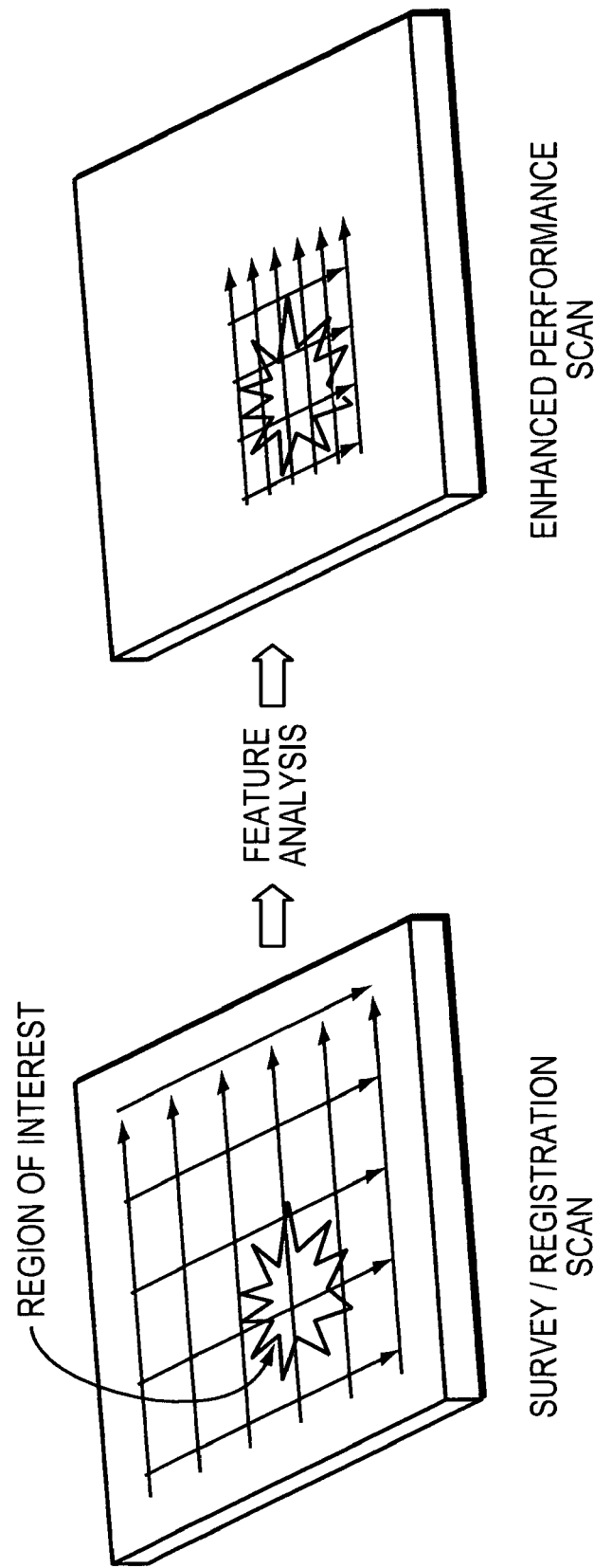
FIG. 31 is a flow diagram depicting intelligent scanning applications in microscopy, endoscopy, and colposcopy according to an illustrative embodiment of the invention.

This embodiment is shown schematically in FIG. 31. As shown, survey scans are performed over a large region of a sample. The survey scans are analyzed using imaging processing to identify the presence and location of regions of interest. In many cases, the regions of interest correspond to abnormalities in a sample that can be detected in the OCT images. Then the mode of the OCT instrument is changed to "enhanced performance" scanning. The OCT beam scanning is aimed so that encompasses the smaller region of the sample which is the region of interest. Then enhanced performance data is acquired from the region of interest.

Figures 32A, 32B:
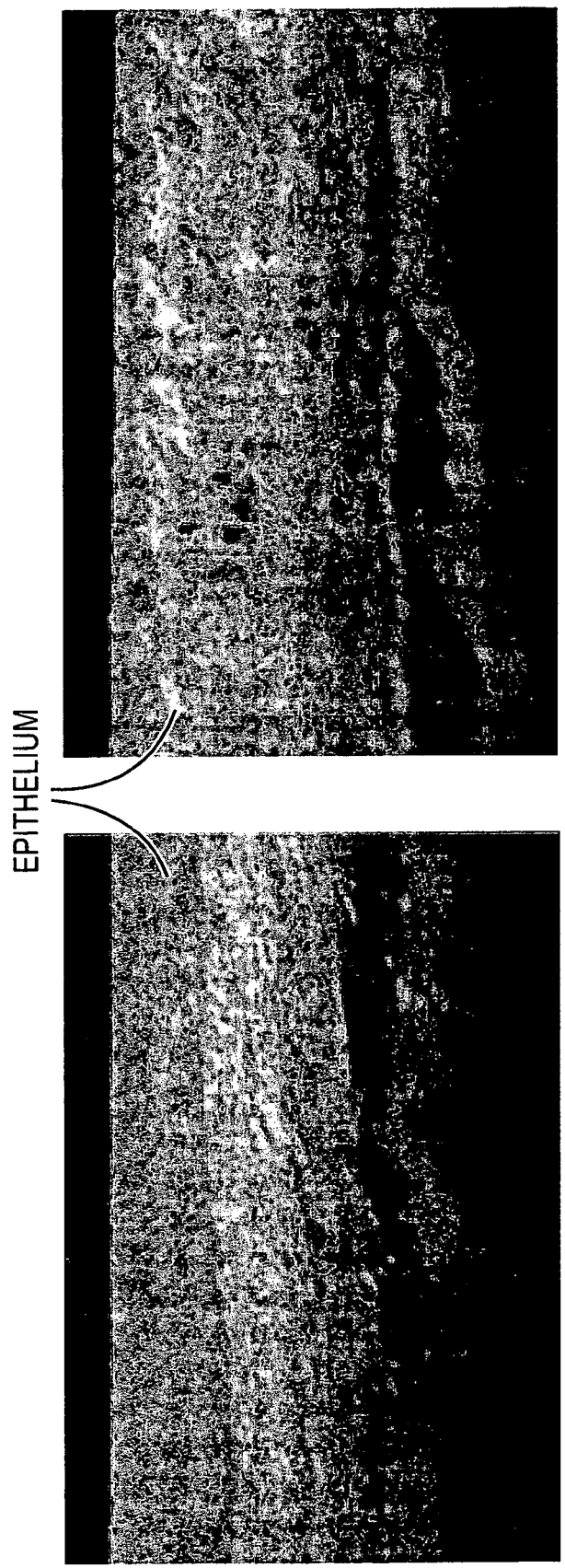
FIGS. 32A-32B are images depicting OCT endoscopy scans to detect areas of pathology or abnormality according to an illustrative embodiment of the invention.

As noted, regions of interest can be, but are not limited to regions which have abnormalities. FIGS. 32A-32B shows an example of OCT images of the esophagus which have normal structure (FIG. 32A) versus early neoplastic changes (FIG. 32B). The presence of normal esophagus is characterized by organized layered structure while early neoplastic change is characterized by loss of layered organization, increased disorganization and the presence of small glands (seen as void like structures on the OCT image).

These changes can be detected using image processing and analysis algorithms. The definition of region of interest will be dependent upon the application. In endoscopic imaging, image features which might indicate a region of interest include, but are not limited to: disruption of normal tissue architecture, disruption of epithelium, disruption of crypts, variations in crypt sizes. In intravascular imaging, image features which might indicate a region of interest include, but are not limited to: atherosclerotic plaque, vulnerable plaque, intravascular stents, macrophages and intimal hyperplasia.

An important example of intelligent scanning for directing enhanced performance OCT scanning occurs in intravascular imaging or intraluminal imaging in general. FIG. 33A shows a schematic of an OCT catheter inserted into a lumen. In one embodiment of intelligent scanning, areas of pathology or abnormality are the regions of interest and are automatically detected from survey/registration scan data acquired as the catheter is pulled back or translated. This embodiment uses an OCT imaging catheter, guidewire, or similar device where OCT scanning and mapping is performed using a pull-back method. The pull-back method is known in intravascular ultrasound imaging and entails changing the longitudinal position of the imaging catheter, guidewire, or similar device by pulling or pushing while transverse scanning is performed by rapidly rotating the angular position of the OCT beam.

For many applications, it is desirable to perform imaging over a large length of a blood vessel or lumen as rapidly as possible to survey or map the three dimensional luminal structure. For example, survey imaging may be performed with a pull-back method and survey images analyzed for the presence of pathology or other abnormalities. When a region of interest is detected, the rate of pullback is reduced to yield higher pixel density or enhanced performance imaging data in the region of pathology. This is shown schematically in FIG. 33B. In this application, the scan pattern is controlled in a parametric fashion. That is, the speed of the pullback is reduced to generate a denser scan pattern with high axial density images and more data in the region of interest. There are other embodiments where the scanning and image or data acquisition can be controlled parametrically to adjust the acquisition parameters for a region of interest. While this example describes changing the rate of pullback, it is understood that other parameters or the mode of the OCT imaging apparatus may also be controlled.

It should be appreciated that various aspects of the claimed invention are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Accordingly, what is desired to be secured by Letters Patent is the invention as defined and differentiated in the following claims, including all equivalents.

What is claimed is:

1. A method of processing optical coherence tomography (OCT) data obtained from a sample, the method comprising:
   analyzing at least a first subset of an OCT data set to identify landmark region data;
   placing the OCT data set in correspondence with the landmark region data; and
   processing at least a second subset of the OCT data set based on the correspondence of the OCT data set to the landmark region data, the OCT data set being derived from measurements of backscattering or back-reflection as a function of optical depth within the sample.

2. The method of claim 1 further comprising selecting another subset of data from the OCT data set for processing based on the correspondence of the OCT data set.

3. The method of claim 1 further comprising generating an image using the OCT data set.

4. The method of claim 3 wherein the image is an en face image.

5. The method of claim 1 further comprising generating numerical measurements regarding portions of elements in the sample using the OCT data set.

6. The method of claim 5 wherein the elements are constituents of a human eye.

7. The method of claim 1 further comprising correcting for motion error using the landmark region data.

8. The method of claim 1 wherein the sample is an eye, the second subset of data includes a circumpapillary scan, and the OCT data set includes data from a peripapillary region.

9. The method of claim 1 further comprising longitudinally monitoring changes in the second subset of data at different points in time.

10. The method of claim 9 further including monitoring a retinal nerve fiber layer thickness over time.

11. The method of claim 1 wherein at least a portion of the OCT data set is a three dimensional data set generated by a raster scan and analyzing at least the first subset of the OCT data includes transforming three dimensional OCT data to two dimensional data.

12. The method of claim 1 wherein the landmark region data includes a representation of an optic disc.

13. The method of claim 12 wherein processing includes measuring retinal nerve fiber layer thickness registered to a center of the optic disc.

14. The method of claim 1 wherein the landmark region data includes a representation of a macula.

15. The method of claim 14 wherein processing includes measuring retinal thickness registered to a center of the macula.

16. The method of claim 1 wherein the landmark region data includes a representation of a fovea.

17. The method of claim 1 wherein the first subset of the OCT data set includes data from the second subset of the OCT data set.

18. The method of claim 1 wherein the first subset of the OCT data set includes data other than data in the second subset of the OCT data set.

19. The method of claim 1 wherein the OCT data set is derived from Fourier domain measurements of backscattering or back-reflection.

20. A method of processing optical coherence tomography (OCT) data obtained from a sample, the method comprising:
analyzing at least a first subset of an OCT data set to identify landmark region data;
registering the OCT data set by aligning the OCT data set using the landmark region data; and
processing at least a second subset of the OCT data set in response to registration of the OCT data set, the OCT data set being derived from measurements of backscattering or back-reflection as a function of optical depth within the sample.

21. The method of claim 20 further comprising selecting another subset of data from the OCT data set for processing in response to the registration of the OCT data set.

22. The method of claim 20 further comprising generating an image using the OCT data set.

23. The method of claim 22 wherein the image is an en face image.

24. The method of claim 20 further comprising generating numerical measurements regarding portions of elements in the sample using the OCT data set.

25. The method of claim 24 wherein the elements are constituents of a human eye.

26. The method of claim 20 further comprising correcting for motion error using the landmark region data.

27. The method of claim 20 wherein the sample is an eye, the second subset of data includes a circumpapillary scan, and the OCT data set includes data from a peripapillary region.

28. The method of claim 20 further comprising longitudinally monitoring changes in the second subset of data at different points in time.

29. The method of claim 28 further including monitoring a retinal nerve fiber layer thickness over time.

30. The method of claim 20 wherein at least a portion of the OCT data set is a three dimensional data set generated by a raster scan and analyzing at least the first subset of the OCT data includes transforming three dimensional OCT data to two dimensional data.

31. The method of claim 20 wherein the landmark region data includes a representation of an optic disc.

32. The method of claim 31 wherein processing includes measuring retinal nerve fiber layer thickness registered to a center of the optic disc.

33. The method of claim 20 wherein the landmark region data includes a representation of a macula.

34. The method of claim 33 wherein processing includes measuring retinal thickness registered to a center of the macula.

35. The method of claim 20 wherein the landmark region data includes a representation of a fovea.

36. The method of claim 20 wherein the first subset of the OCT data set includes data from the second subset of the OCT data set.

37. The method of claim 20 wherein the first subset of the OCT data set includes data other than data in the second subset of the OCT data set.

38. The method of claim 20 wherein the OCT data set is derived from Fourier domain measurements of backscattering or back-reflection.

39. A method of processing optical coherence tomography (OCT) data obtained from a sample, the method comprising:
analyzing at least a first subset of an OCT data set to identify landmark region data;
registering the OCT data set by identifying a position of the OCT data set relative to a location of the landmark region data; and
processing at least a second subset of the OCT data set in response to registration of the OCT data set, the OCT data set being derived from Fourier-domain measurements of backscattering or back-reflection as a function of optical depth within the sample.

40. The method of claim 39 further comprising selecting another subset of data from the OCT data set for processing in response to the registration of the OCT data set.

41. The method of claim 39 further comprising generating an image using the OCT data set.

42. The method of claim 41 wherein the image is an en face image.

43. The method of claim 39 further comprising generating numerical measurements regarding portions of elements in the sample using the OCT data set.

44. The method of claim 43 wherein the elements are constituents of a human eye.

45. The method of claim 39 further comprising correcting for motion error using the landmark region data.

46. The method of claim 39 wherein the sample is an eye, the second subset of data includes a circumpapillary scan, and the OCT data set includes data from a peripapillary region.

47. The method of claim 39 further comprising longitudinally monitoring changes in the second subset of data at different points in time.

48. The method of claim 47 further including monitoring a retinal nerve fiber layer thickness over time.

49. The method of claim 39 wherein at least a portion of the OCT data set is a three dimensional data set generated by a raster scan and analyzing at least the first subset of the OCT data includes transforming three dimensional OCT data to two dimensional data.

50. The method of claim 39 wherein the landmark region data includes a representation of an optic disc.

51. The method of claim 50 wherein processing includes measuring retinal nerve fiber layer thickness registered to a center of the optic disc.

52. The method of claim 39 wherein the landmark region data includes a representation of a macula.

53. The method of claim 52 wherein processing includes measuring retinal thickness registered to a center of the macula.

54. The method of claim 39 wherein the landmark region data includes a representation of a fovea.

55. The method of claim 39 wherein the first subset of the OCT data set includes data in the second subset of the OCT data set.

56. The method of claim 39 wherein the first subset of the OCT data set includes data other than data in the second subset of the OCT data set.

57. A method of processing optical coherence tomography (OCT) data, the method comprising:
obtaining an OCT data set from a sample, at least a portion of the OCT data set being obtained by raster scanning the sample;
analyzing at least a first subset of the OCT data set to identify landmark region data;
registering the OCT data set by identifying a position of the OCT data set relative to a location of the landmark region data; and
processing at least a second subset of the OCT data set to obtain at least one measurement associated with a part of the sample whose location is determined with respect to the landmark region data, the OCT data set being derived from Fourier-domain measurements of backscattering or back-reflection as a function of optical depth within the sample.

58. The method of claim 57 wherein the first subset of the OCT data set includes data in the second subset of the OCT data set.

59. The method of claim 57 wherein the first subset of the OCT data set includes data other than data in the second subset of the OCT data set.

60. The method of claim 57 wherein the OCT data set includes three-dimensional data and wherein analyzing at least the first subset of the OCT data set includes transforming three-dimensional OCT data to two-dimensional data.

61. The method of claim 60 wherein the two-dimensional data includes an en face image.

62. The method of claim 57 wherein the OCT data set includes three-dimensional data and wherein registering the OCT data set includes transforming three-dimensional OCT data into two-dimensional data.

63. The method of claim 62 wherein the two-dimensional data includes an en face image.

* * * * *